US009574231B2

(12) United States Patent
Gilbert et al.

(10) Patent No.: US 9,574,231 B2
(45) Date of Patent: *Feb. 21, 2017

(54) METHOD FOR IDENTIFYING CELLS BASED ON DNA REPLICATION DOMAIN TIMING PROFILES

(71) Applicant: FLORIDA STATE UNIVERSITY RESEARCH FOUNDATION, Tallahassee, FL (US)

(72) Inventors: David M. Gilbert, Tallahassee, FL (US); Tyrone Ryba, Sarasota, FL (US); Ichiro Hiratani, Kobe (JP)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 90 days.

This patent is subject to a terminal disclaimer.

(21) Appl. No.: 14/267,953

(22) Filed: May 2, 2014

(65) Prior Publication Data
US 2014/0243221 A1   Aug. 28, 2014

Related U.S. Application Data

(62) Division of application No. 12/200,186, filed on Aug. 28, 2008, now Pat. No. 8,728,979.

(60) Provisional application No. 60/969,399, filed on Aug. 31, 2007.

(51) Int. Cl.
  *C12Q 1/68*   (2006.01)
  *G01N 33/50*  (2006.01)

(52) U.S. Cl.
  CPC ........... *C12Q 1/6837* (2013.01); *C12Q 1/6804* (2013.01); *C12Q 1/6806* (2013.01); *C12Q 1/6809* (2013.01); *G01N 33/5005* (2013.01)

(58) Field of Classification Search
  None
  See application file for complete search history.

(56) References Cited

PUBLICATIONS

Korbel et al (2007) "Paired-end mapping reveals extensive structural variation in the human genome." Science 318(5849):420-426.*
Leary et al. (2007) "Digital Karyotyping" Nature Protocols 2(8):1973-1986.*
Azuara et al., "Chromatin signatures of pluripotent cell lines," Nat. Cell Biol. 8:532-538 (2006).
Azuara et al., "Heritable gene silencing in lymphocytes delays chromatid resolution without affecting the timing of DNA replication," Nat. Cell Biol. 5(7):668-674 (2003).
Azuara V., "Profiling of DNA replication timing in unsynchronized cell populations," Nat. Protoc. 1(4):2171-2177 (2006).
Bolstad BM, "Quality Assessment of Affymetrix GeneChip Data," in: Gentleman et al., Bioinformatics and Computational Biology Solutions using R and Bioconductor (New York, NY, Springer, 2005, pp. 33-48).
Buck et al., "Detection of S-phase cell cycle progression using 5-ethynyl-2'-deoxyuridine incorporation with click chemistry, an alternative to using 5-bromo-2'-deoxyuridine antibodies." Biotechniques 44(7):927-9 (2008).
Costantini et al. "An isochore map of human chromosomes," Genome Res 16:536-541 (2006).
Freshney, R. I., "Culture of Animal Cells: A Manual of Basic Techniques," (4th Ed., 2000), Table of Contents only.
Gilbert DM, "Temporal order of replication of Xenopus laevis 5S ribosomal RNA genes in somatic cells," PNAS USA 83:2924-2928 (1986).
Gilbert et al., "Bovine papilloma virus plasmids replicate randomly in mouse fibroblasts throughout S phase of the cell cycle," Cell 50:59-68 (1987).
Gilbert et al., "Nuclear Structure and DNA Replication," in: DePamphilis ML, Editor DNA Replication and Human Disease (Cold Spring Harbor Press, Cold Spring Harbor, New York: 2006).
Grasser et al., "Replication timing-correlated spatial chromatin arrangements in cancer and in primate interphase nuclei," J. Cell Sci. 121(11):1876-86 (2008).
Hansen et al., "Association of fragile X syndrome with delayed replication of the FMR1 gene," Cell 73:1403-1409 (1993).
Hawkins et al., "Whole genome amplification—applications and advances," Current Opinion in Biotechnology 13(1):65-67 (2002).
Hiratani et al., "Differentiation-induced replication-timing changes are restricted to AT-rich/long interspersed nuclear element (LINE)-rich isochores," PNAS USA 101:16861-16866 (2004).
Hiratani et. al, "Global Re-organization of replication domains during embryonic stem cell differentiation." PlosBiology, in press (2008).
Hughes et al., "The use of whole genome amplification in the study of human disease," Progress in Biophys. and Mol. Biol. 88(1):173-189 (2005).
Innis, M. A. et al., "PCR Strategies," Academic Press (1995), Table of Contents only.

(Continued)

*Primary Examiner* — Karen S Weiler
(74) *Attorney, Agent, or Firm* — Fox Rothschild LLP

(57) ABSTRACT

Methods for identifying and/or distinguishing a homogeneous population of cells based on their replication domain timing profile using high resolution genomic arrays or sequencing procedures are provided. These methods may be used to compare the replication timing profile for a population of cells to another replication timing profile(s), a replication timing fingerprint, and/or one or more informative segments of a replication timing fingerprint, which may be simultaneously or previously determined and/or contained in a database, to determine whether there is a match between them. Based on such information, the identity of the population of cells may be determined, or the identity of the population of cells may be distinguished from other populations of cells or cell types. Methods for determining a replication timing fingerprint for particular cell types are also provided.

17 Claims, 42 Drawing Sheets

(56) References Cited

PUBLICATIONS

Jorgensen et al., "The impact of chromatin modifiers on the timing of locus replication in mouse embryonic stem cells," Genome Biol. 8:R169 (2007).
Kwoh et al., "Target amplification systems in nucleic acid-based diagnostic approaches," Am. Biotechnol. Lab. 8(13):14-25 (1990).
Lasken et al., "Whole genome amplification: abundant supplies of DNA from precious samples or clinical specimens," Trends in Biotechnology 21(12):531-535 (2003).
Lieu et al., "Development of a DNA-Labeling System for Array-based Comparative Genomic Hybridization," J. Biomol. Tech. 16(2):104-111 (2005).
MacAlpine et al., "Coordination of replication and transcription along a Drosophila chromosome," Genes. Dev. 18:3094-3105 (2004).
O'Geen et al., "Comparison of sample preparation methods for ChIP-chip assays," Biotechniques 41(5):577-580 (2006).
Oliver et al., J. Oral Pathol. Med. 29(9):426-431 (2000).
Olshen et al., "Circular binary segmentation for the analysis of array-based DNA copy number data," Biostatistics 5(4):557-72 (2004).
Perry et al., "A dynamic switch in the replication timing of key regulator genes in embryonic stem cells upon neural induction," Cell Cycle 3:1645-1650 (2004).
Sambrook J. et al., "Molecular Cloning: A Laboratory Manual," (3rd Ed., Cold Spring Harbor Laboratory Press, Cold Spring Harbor, N.Y., 2001), Table of Contents only.
Schmegner et al., "Isochores and replication time zones: a perfect match," Cytogenet. Genome Res. 116:167-172 (2007).
Schubeler et al., "Genome-wide DNA replication profile for Drosophila melanogaster: a link between transcription and replication timing," Nat. Genet. 32:438-442 (2002).
Sninsky, J.J. et al., "PCR Applications: Protocols for Functional Genomics," (Academic Press, 1999), Table of contents only.
Spector, D. L., Cells: "A Laboratory Manual, Culture and Biochemical Analysis of Cells," (Cold Spring Harbor Press, 1998), Table of Contents only.
Watanabe et al., "Chromosome-wide assessment of replication timing for human chromosomes 11q and 21q: disease related genes in timing-switch regions," Hum Mol Genet 11:13-21 (2002).
White et al., "DNA replication timing analysis of human chromosome 22 at high resolution and different developmental states." PNAS USA 101:17771-17776 (2004).
Woodfine et al., "Replication Timing of Human Chromosome 6," Cell Cycle 4:172-176 (2005).
Woodfine et al., "Replication timing of the human genome," Hum. Mol. Genet. 13:191-202 (2004).
Farkash-Ama, et al., "Global Organization of Replication Time Zones of the Mouse Genome," Genome Research, 18:1562-1570 (2008).
Schwaiger M., et al. "Chromatin State Marks Cell-Type and Gender Specific Replication of the *Drosophila* Genome," Genes & Development 23(5):589-601 (2009).
Woodfine, Human Molecular Genetics, Supplementary Material, pp. 1-6, vol. 13, pp. 191-202, (Nov. 25, 2003).
Hiratani, Proceedings of the National Academy of Sciences USA, vol. 101 pp. 1661-1666, (Nov. 19, 2004).
Woodfine, Cell Cycle, vol. 4, pp. 172-176, (Jan. 2005).
Meshorer, Developmental Cell vol. 10, pp. 105 to 116, (Jan. 9, 2006).
Gilbert, Cell, vol. 50, pp. 59-68, (Jul. 3, 1987).
Bolstad, Bioinformatics, vol. 19, pp. 185-193, (Jan. 22, 2003).
Fiegler, Genes Chromosomes and Cancer, vol. 36, pp. 361-374 (Jan. 30, 2003).
Meshoroer, Nature Reviews Molecular Cell Biology, vol. 7, pp. 540-546, (Jul. 2006).
Wu, Journal of Cell Biology, vol. 174, pp. 185 to 194, Jul. 10, 2006.
Attwood et al., CMLS 59:241-257 (2002), abstract only.
Ausubel, F. M., "Short Protocols in Molecular Biology: A Compendium of Methods from Current Protocols in Molecular Biology," (Wiley & Sons, 5th Ed., 2002), publication information only.
Beatty, B. et al., Editors, FISH: Practical Approach, (Oxford: Oxford Univ. Press. 2002), publication information only.
Bernardi G, "Isochores and the evolutionary genomics of vertebrates," Gene 241:3-17 (2000), abstract only.
Bernstein et al., "A bivalent chromatin structure marks key developmental genes in embryonic stem cells," Cell 125:315-326 (2006), abstract only.
Birney et al., "Identification and analysis of functional elements in 1% of the human genome by the ENCODE pilot project," Nature 447:799-816 (2007).
(NCBI annotation at http://www.ncbi.nlm.nih.gov/RefSeq/), web homepage Jan. 28, 2016.
Burton et al., Gene 293:21-31 (2002), abstract only.
Cimbora et al., "Long-Distance Control of Origin Choice and Replication Timing in the Human B-Globin Locus are Independent of the Locus Control Region," Mol. Cell Biol. 20:5581-5591 (2000).
Costantini et al., "Replication timing, chromosomal bands, and isochores," PNAS USA 105:3433-3437 (2008).
DeRisi et al., Science 278:680-686 (1997).
Dimitrova et al., "The spatial position and replication timing of chromosomal domains are both established in early 31-phase," Mol. Cell. 4:983-993 (1999).
Doetschman et al., "The in vitro development of blastocyst-derived embryonic stem cell lines: formation of visceral yolk sac, blood islands and myocardium," J. Embryol. Exp. Morphol. 87:27-45 (1985).
Efroni et al., "Global transcription in pluripotent embryonic stem cells," Cell Stem Cell 2:437-447 (2008).
Esteller et al., Oncogene 21:5427-5440 (2002).
Garcia-Perez et al., "LINE-1 retrotransposition in human embryonic stem cells," Hum. Mol. Genet. 16:1569-1577 (2007).
Gilbert DM, "Replication timing and transcriptional control: beyond cause and effect," Curr. Opinion, Cell Biol. 14:377-383 (2002).
Gilbert et al., "Temporal order of replication of Xenopus laevis 5S ribosomal RNA genes in somatic mils," PNAS 83:2924-2928 (1986).
Goren et al., "Replicating by the clock," Nat. Rev. Mol. Cell Biol. 4:25-32 (2003), abstract only.
Hanna et al., "Treatment of sickle cell anemia mouse model with iPS cells generated from autologous skin," Science 318:1920-1923 (2007).
http://genome.ucsc.edu, web page screenshot only Feb. 3, 2016.
http://www.replicationdomain.org, homepage Feb. 4, 2016.
http://www.r-project.org, homepage Feb. 3, 2016.
Jackson et al., "Replicon clusters are stable units of chromosome structure: evidence that nuclear organization contributes to the efficient activation and propagation of S phase in human cells," J. Cell Biol. 140:1285-1295 (1998).
Jones et al., Nature Genetics 21:163-167 (1999), abstract only.
Krude, T. "Chromatin assembly during DNA replication in somatic cells," Eur. J. Biochem. 263, pp. 1-5 (1999) (not cited in specification), abstract only.
Labib et al., "Replication fork barriers: pausing for a break or stalling for time?" EMBO Rep. 8:346-353 (2007).
Laird et al., Nature Reviews Cancer 3:253-266 (2003), abstract only.
Li et al., "The replication timing program of the Chinese hamster beta-globin locus is established coincident with it repositioning near peripheral heterochromatin in early G1 phase," J. Cell Biol. 154:283-292 (2001).
Li et al., "The role of chromatin during transcription," Cell 128:707-719 (2007).
Ma et al., "Spatial and temporal dynamics of DNA replication sites in mammalian cells," J. Cell Biol. 143:1415-1425 (1998).
Martens et al., "The profile of repeat-associated histone lysine methylation states in the mouse epigenome." EMBO J. 24:800-812 (2005).

(56) References Cited

OTHER PUBLICATIONS

Mikkelsen et al., "Genome-wide maps of chromatin state in pluripotent and lineage-committed cells," Nature 448:553-560 (2007).

Miller et al., Cancer Cell 2:353-61 (2002).

Murphy D, Adv Physiol Educ, 26:256-70, (2002).

Norio et al., "Progressive activation of DNA replication initiation in large domains of the immunoglobulin heavy chain locus during B cell development," Mol Cell 20:575-587 (2005).

O'Keefe et al., "Dynamic organization of DNA replication in mammalian cell nuclei—spatially and temporally defined replication of Chromosome-Specific alpha-Satellite DNA sequences," J. Cell Biol. 116:1095-1110 (1992).

Panning et al., "Spatio-temporal organization of DNA replication in murine embryonic stem, primary, and immortalized cells," J. Cell Biochem. 95:74-82 (2005).

Rathjen et al., "Directed differentiation of pluripotent cells to neural lineages: homogenous formation and differentiation of a neurectoderm population." Development 129:2649-2661 (2002).

Rathjen et al., "Lineage specific differentiation of mouse ES cells: formation and differentiation of early primitive ectoderm-like (EPL) cells," Methods Enzymol. 365:3-25 (2003), abstract only.

Sadoni et al., "Stable chromosomal units determine the spatial and temporal organization of DNA replication," J. Cell Sci. 117:5353-5365 (2004).

Schwaiger et al., "A question of timing: emerging links between transcription and replication," Curr. Opin. Genet. Dev. 16:177-183 (2006), abstract only.

Silva et al., "Capturing pluripotency," Cell 132:532-536 (2008).

Spellman et al., Mol. Biol. Cell 9:3273-97 (1998).

Sporbert et al., "DNA polymerase clamp shows little turnover at established replication sites but sequential de novo assembly at adjacent origin clusters," Mol. Cell 10:1355-1365 (2002).

Tabancay, Jr. et al. "Eukaryotic DNA Replication in a Chromatin Context," Molecular and Computational Biology Section, Current Topics in Development Biology, vol. 76 Chapter 5, pp. 129-184 (2006) (not cited in specification), abstract only.

Takahashi et al., "Induction of pluripotent stem cells from mouse embryonic and adult fibroblast cultures by defined factors." Cell 126:663-676 (2006).

Takebayashi et al., "Regulation of replication at the R/G chromosomal band boundary and pericentromeric heterochromatin of mammalian cells," Exp. Cell Res. 304:162-174 (2005), abstract only.

Thurman et al., "Identification of higher-order functional domains in the human ENCODE regions," Genome Res 17:917-927 (2007).

Toyooka et al., "Identification and characterization of subpopulations in undifferentiated ES cell culture," Development 135:909-918 (2008).

Venkatraman et al., : A faster circular binary segmentation algorithm for the anlaysis of array CGH data. Bioinformatics 23:657-663 (2007).

Watanabe et al., "Amplicons on human chromosome 11q are located in the early/late-switch regions of replication timing," Genomics 84:796-805 (2004), abstract only.

Weber et al., "Distribution, silencing potential and evolutionary impact of promoter DNA methylation in the human genome," Nat. Genet. 39:457-466 (2007), abstract only.

Wijgerde et al., "Transcription complex stability and chromatin dynamics in vivo," Nature 377:209-213 (1995), abstract only.

Wu et al., "Differential subnuclear localization and replication timing of histone H3 lysine 9 methylation states," Mol. Biol. Cell 16:2872-2881 (2005).

Yagi et al., "A novel ES cell line, TT2, with high germline-differentiating potency," Anal. Biochem. 214:70-76 (1993), abstract only.

Ying et al., "Conversion of embryonic stem cells into neuroectodermal precursors in adherent monoculture," Nat. Biotechnol. 21:183-186 (2003), abstract only.

Zhou et al. "Cell Cycle Regulation of Chromatin at an origin of DN replication," EMBO Journal 24, pp. 1406-1417 (2005) (not cited in specification).

Nadon et al., Trends Genet 18:265-71 (2002) (Abstract only).

\* cited by examiner

|  | PCR | | | | Microarray | | | |
| --- | --- | --- | --- | --- | --- | --- | --- | --- |
|  | Mean %early S | | E or L | | Log2(Early/Late) | | E or L | |
| Gene name | ESC | NPC | ESC | NPC | ESC | NPC | ESC | NPC |
| Rex1/Zfp42 | 74% | 23% | E | L | 0.88 | −0.94 | E | L |
| Rex2 | 65% | 35% | E | L | 1.22 | −1.67 | E | L |
| Dppa2 | 71% | 24% | E | L | 1.16 | −1.30 | E | L |
| Dppa4 | 68% | 25% | E | L | 1.17 | −1.45 | E | L |
| Crisp1 | 46% | 29% | L | L | −0.76 | −1.25 | L | L |
| Trap1a | 52% | 40% | E | L | 0.18 | −0.72 | E | L |
| Ephb1 | 47% | 67% | L | E | −1.32 | 0.64 | L | E |
| Akt3 | 40% | 61% | L | E | −0.97 | 0.30 | L | E |
| Ptn | 38% | 62% | L | E | −0.91 | 0.79 | L | E |
| Cdh2 | 33% | 47% | L | L | −1.23 | −0.45 | L | L |
| Postn | 32% | 47% | L | L | −1.36 | −0.45 | L | L |
| Mash1/Ascl1 | 30% | 47% | L | L | −1.03 | 0.05 | L | E |
| Nanog | 80% | 65% | E | E | 0.62 | 1.09 | E | E |
| Fgf4 | 80% | 69% | E | E | 1.00 | 0.91 | E | E |
| Oct-4/Pou5f1 | 76% | 78% | E | E | 0.73 | 1.14 | E | E |
| Mmp15 | 84% | 80% | E | E | 1.16 | 0.88 | E | E |
| α-globin/Hba-a1 | 73% | 79% | E | E | 1.32 | 1.20 | E | E |
| β-globin/Hbb-b1 | 21% | 20% | L | L | −0.84 | −1.10 | L | L |
|  |  |  |  |  |  | Matched: | 18/18 (100%) | 17/18 (94%) |

FIG. 2A

| Gene name | PCR (Hiratani et al, 46CESC) E or L | Microarray (D3ESC) Log2(E/L) | E or L |
|---|---|---|---|
| Lefty2 | E | 0.85 | E |
| Dmrt1 | E | 0.66 | E |
| Tdgf1/Cripto | E | 0.99 | E |
| Tcfap2c | E | 1.07 | E |
| 2010004A03Rik | E | 1.02 | E |
| Utf1 | E | 0.84 | E |
| Ptgis | E | 1.10 | E |
| Epha2 | E | 0.53 | E |
| Pcolce | E | 0.64 | E |
| Ltbr | E | 1.36 | E |
| Ddr1 | E | 1.06 | E |
| Dll1 | E | 1.52 | E |
| Mmp15 | E | 1.16 | E |
| Slc25a10 | E | 0.68 | E |
| Nfatc1 | E | 0.71 | E |
| Bmp1 | E | 1.26 | E |
| Fgfr1 | E | 1.21 | E |
| Gpr56 | E | 1.39 | E |
| Rex1/Zfp42 | E | 0.88 | E |
| Rex2 | E | 1.22 | E |
| Spp1 | E | 0.73 | E |
| 1700034H14Rik | E | 1.14 | E |
| Ctgf | E | 1.28 | E |
| Ddx4 | E | 1.60 | E |
| Rbpms | E | 1.33 | E |
| Tfpi | E | 1.53 | E |
| Terf1 | E | 1.18 | E |
| Ptn | L | −0.91 | L |
| Tspan12/Tm4sf12 | L | −1.34 | L |

| | | | |
|---|---|---|---|
| Postn | L | −1.36 | L |
| Lox | L | −0.82 | L |
| Mtap2 | E | −1.15 | L |
| Sox6 | E | −1.17 | L |
| Ptgs2 | L | −1.12 | L |
| Crisp1 | E | −0.76 | L |
| Adcy8 | L | −1.29 | L |
| Car8 | L | −1.08 | L |
| Sprr2a | L | −1.10 | L |
| A2m | L | −1.00 | L |
| Mme | E | −0.61 | L |
| Cdh4 | E | 0.41 | E |
| Lmo1 | E | −0.15 | L |
| Trap1a | E | 0.18 | E |
| Gbp3 | E | 0.10 | E |
| NrOb1 | L | −0.25 | L |
| Egfr | E | −0.36 | L |
| Col1a2 | E | 0.24 | E |

41/47 Matched (87%)

FIG.2B-1

| Gene name | PCR (Perry et al, OS25ESC) E or L | Microarray (D3ESC) Log2(E/L) | E or L |
|---|---|---|---|
| Scl/Tal1 | E | 0.93 | E |
| Lmo2 | E | 1.18 | E |
| Gata1 | E | 0.37 | E |
| Gata2 | E | 1.23 | E |
| Gata3 | E | 0.95 | E |
| T-bet/Tbx21 | E | 1.04 | E |
| Ebf1 | L | 0.47 | E |
| Pax5 | E | 1.10 | E |
| Ikaros/Ikzf1 | E | 1.19 | E |
| NF-E2/Nfe2 | E | 1.00 | E |
| C/EBPalpha (Cebpa) | E | 1.29 | E |
| PU.1/Sfpi1 | E | 1.21 | E |
| Myb/c-myb | E | 1.23 | E |
| Myog | E | 1.30 | E |
| Myod1/Myod | E | 0.93 | E |
| Myf5 | E | −1.34 | L |
| Sox1 | E | 1.38 | E |
| Sox2 | E | 0.94 | E |
| Sox3 | L | −0.58 | L |
| Irx3 | E | 0.50 | E |
| Nkx2-2 | E | 0.98 | E |
| Nkx2-9 | E | 0.00 | E |
| Msx1 | E | 0.25 | E |
| Pax3 | E | 0.44 | E |
| Pax6 | E | 0.71 | E |
| Pax7 | E | 0.85 | E |

| | | | |
|---|---|---|---|
| Olig2 | E | 0.93 | E |
| Neurod/Neurod1 | L | −0.71 | L |
| Mash1/Ascl1 | L | −1.03 | L |
| Math1/Atoh1 | E | 1.14 | E |
| Neurog1/Ngn1 | E | 0.97 | E |
| Neurog2/Ngn2 | E | 0.68 | E |
| Hes1 | E | 1.23 | E |
| Hes5 | E | 0.88 | E |
| Oct-4/Pou5f1 | E | 0.73 | E |
| Nanog | E | 0.62 | E |
| Utf1 | E | 0.84 | E |
| Rex1/Zfp42 | E | 0.88 | E |
| Foxd3 | E | 0.85 | E |
| Dppa5/Esg1 | E | 0.93 | E |
| Tdgf1/Cripto | E | 0.99 | E |
| Fgf4 | E | 1.00 | E |
| Zfp57 | E | 0.62 | E |

41/43 Matched
(95%)

FIG.2C-1

| $R^2$ | 46CESC | TT2ESC |
|---|---|---|
| D3ESC | 0.91 | 0.90 |
| 46CESC | | 0.91 |

| $R^2$ | D3 NPC | 46C NPC | TT2 NPC |
|---|---|---|---|
| D3ESC | 0.67 | 0.61 | 0.68 |
| 46CESC | 0.61 | 0.67 | 0.72 |
| TT2ESC | 0.66 | 0.68 | 0.77 |
| D3NPC | | 0.80 | 0.82 |
| 46CNPC | | | 0.91 |

FIG.6C

| Replication domains | ESC | NPC |
|---|---|---|
| Number | 1,714 | 1,045 |
| Mean (Mb) | 1.5 | 2.5 |
| Median (Mb) | 0.83 | 1.4 |

|       | Mean domain size (Mb) | | |
|-------|-----|-----|---------|
| Chr   | ESC | NPC | NPC/ESC |
| chr1  | 1.4 | 2.7 | 1.9 |
| chr2  | 1.5 | 2.4 | 1.6 |
| chr3  | 1.4 | 2.0 | 1.5 |
| chr4  | 1.7 | 3.3 | 1.9 |
| chr5  | 1.8 | 3.0 | 1.7 |
| chr6  | 1.7 | 2.5 | 1.5 |
| chr7  | 1.5 | 2.3 | 1.6 |
| chr8  | 1.5 | 2.2 | 1.5 |
| chr9  | 1.3 | 2.2 | 1.7 |
| chr10 | 1.2 | 2.7 | 2.2 |
| chr11 | 1.8 | 3.1 | 1.8 |
| chr12 | 1.5 | 2.5 | 1.7 |
| chr13 | 1.3 | 2.0 | 1.6 |
| chr14 | 1.8 | 2.4 | 1.4 |
| chr15 | 1.5 | 3.1 | 2.1 |
| chr16 | 1.6 | 2.2 | 1.4 |
| chr17 | 1.5 | 2.5 | 1.6 |
| chr18 | 1.2 | 2.1 | 1.7 |
| chr19 | 1.4 | 2.2 | 1.6 |
| chrX  | 2.8 | 3.6 | 1.3 |

FIG.6J

| Domain Category | Mean size (Mb) | %GC | %LINE-1 | Genes/Mb |
|---|---|---|---|---|
| EtoL | 0.58 | 40.3 | 27.5 | 6.9 |
| LtoE | 0.64 | 42.5 | 13.1 | 2.2 |
| EtoE | 2.59 | 45.5 | 8.9 | 13.1 |
| LtoL | 1.15 | 39.3 | 25.5 | 3.5 |

FIG.7G

| | $R^2$, vs Replication Timing | | |
|---|---|---|---|
| | %GC | %LINE-1 | Genes/Mb |
| ESC | 0.27 | 0.18 | 0.16 |
| NPC | 0.52 | 0.46 | 0.13 |

FIG.7H

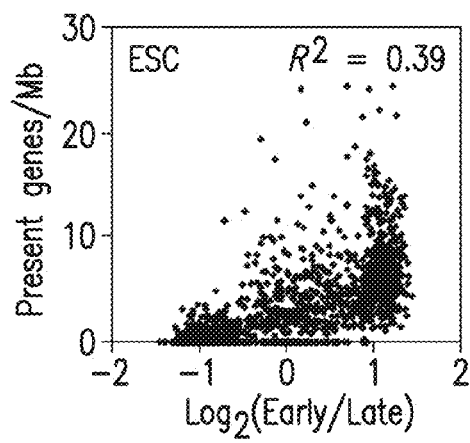
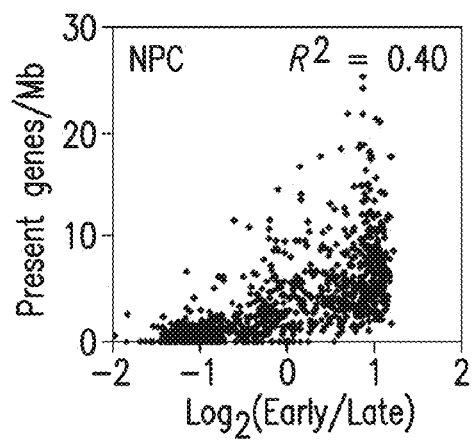
FIG.8A  FIG.8B
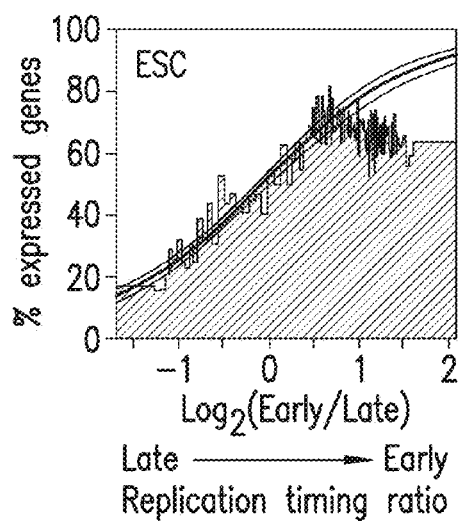
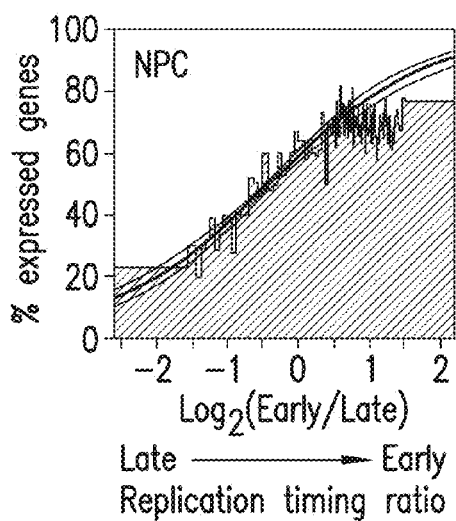
FIG.8C  FIG.8D

| Expression patterns of genes within a domain | LtoE | EtoL | LtoL | EtoE |
|---|---|---|---|---|
| Up + Unchanged | 67% | 4% | 41% | 18% |
| Down + Unchanged | 0% | 29% | 3% | 11% |
| Up + Down + Unchanged | 5% | 6% | 0% | 57% |
| Unchanged Only | 6% | 40% | 22% | 13% |
| Silent Only | 22% | 21% | 33% | 1% |

FIG.8G

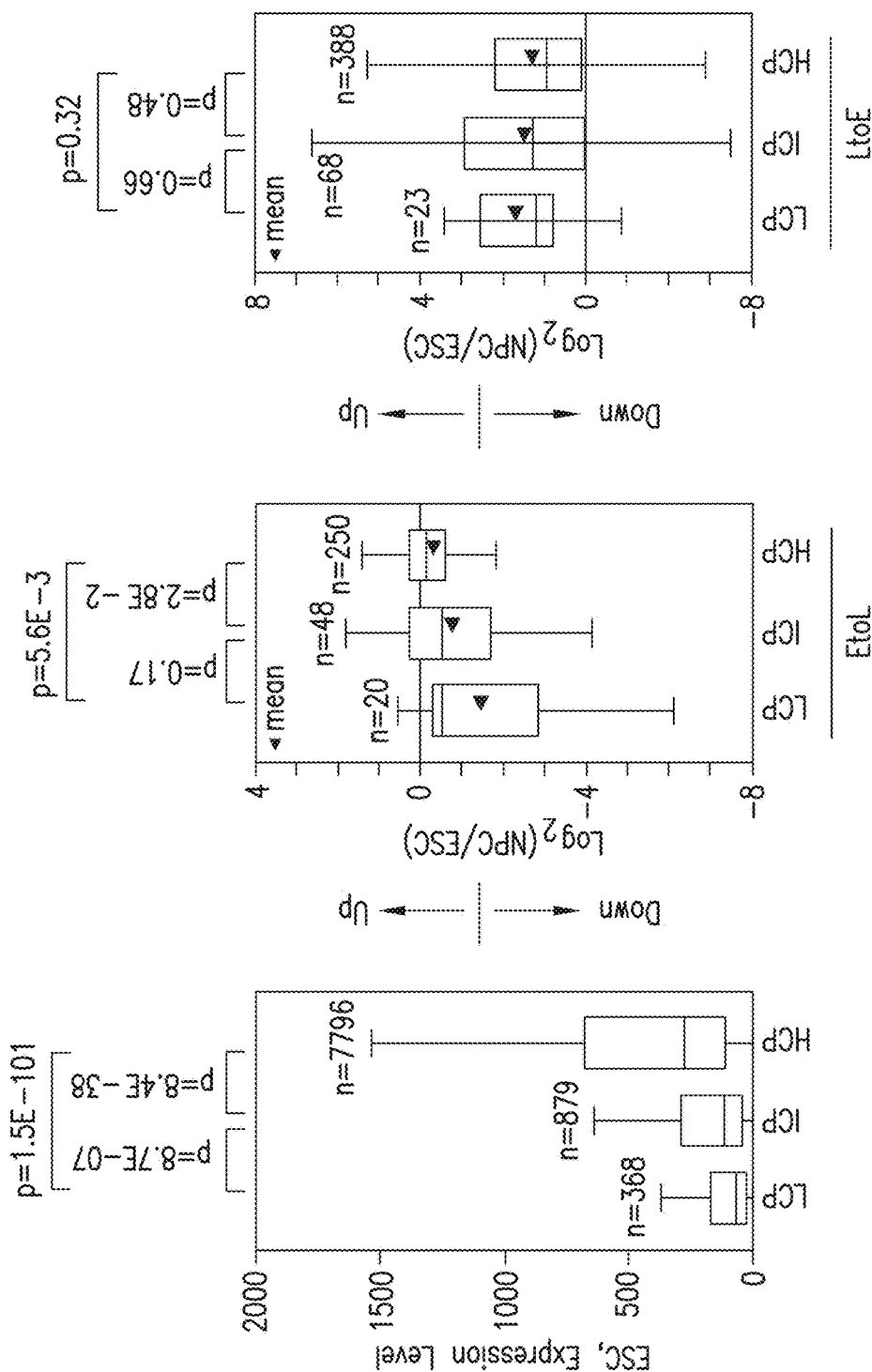

METHOD FOR IDENTIFYING CELLS BASED ON DNA REPLICATION DOMAIN TIMING PROFILES

CROSS-REFERENCE TO RELATED APPLICATIONS

This application is a divisional application of U.S. Pat. App. No. 12/200,186, entitled "METHOD FOR IDENTIFYING CELLS BASED ON DNA REPLICATION DOMAIN TIMING PROFILES," filed Aug. 28, 2008, which claims benefit of priority to U.S Prov. App. No. 60/969,399, entitled "METHOD FOR IDENTIFYING CELLS BASED ON DNA REPLICATION DOMAIN TIMING PROFILES," filed Aug. 31, 2007, and the entire contents and disclosure of this provisional application are hereby incorporated by reference.

GOVERNMENT INTEREST STATEMENT

This invention was made with government support under Grant Nos. GM083337 and GM085354-015319 awarded by the National Institutes of Health (NIH). The government has certain rights in this invention.

BACKGROUND

Field of the Invention

The present invention broadly relates to a method for identifying cells based on their replication domain timing profiles using a high resolution genomic array. The present invention also broadly relates to a method for distinguishing cells from other cells based on replication timing profiles using a high resolution genomic array. The present invention further broadly relates to determining one or more replication timing fingerprints of a cell by comparing replication domain timing profiles obtained using a high resolution genomic array.

Related Art

Conventional mechanisms to classify or identify cells involve a variety of heterogeneous biochemical and molecular procedures. For example, morphology-based approaches (e.g., histology) rely on microscopic examination of cell shape and features to determine cell type. This approach is useful in cases in which cells display a distinctive shape (e.g., long axons in neurons) and/or an easily recognizable feature (e.g., a lipid vesicle stained for fats), but most cells are difficult to distinguish based on their appearance alone. Histology-based procedures to cell identification also require a highly trained person making them impossible to apply in a high-throughput manner.

Protein-based approaches, including biochemical and/or immunological techniques, involve detection of specific proteins that may indicate a particular cell type. A protein may be recognized by an antibody specific for such protein present either on the cell surface (e.g., by immunohistology) or in extracts or samples from disintegrated cells (e.g., by immunoblotting or ELISA). These assays are generally sensitive, fast and simple. However, because each antibody only recognizes one particular protein antigen, such approaches generally do not provide sufficient information to distinguish various types of cells. In other words, a single protein marker is rarely a guarantee of a particular cell type. On the other hand, larger scale protein detection methods (e.g., proteomics) suffer from insufficient sensitivity and a lack of capability for automation.

RNA-based approaches are based generally on the detection of mRNA as a reflection of gene expression that may be indicative of a particular cell type and may be performed individually or using an array system. See, e.g., Spellman et al., *Mol. Biol. Cell* 9:3273-97 (1998); DeRisi et al., *Science* 278:680-686 (1997); Burton et al., *Gene* 293:21-31 (2002). Indeed, these technologies can produce a great deal of information about the overall pattern of gene expression of a cell. However, the decisive drawback of this system is the instability of RNA. Every experiment with RNA must take into account possible degradation of RNA that may occur during sample collection, storage, and experimentation. This is especially problematic when working with archived samples (e.g., preserved biopsies) or with limited amounts of cellular material. A further problem with RNA-based approaches is that mRNA fluctuates in response to temporary changes in environmental conditions. In addition, it has been demonstrated recently that mouse embryonic stem cells (mESCs) display considerable cell-to-cell heterogeneity in the expression of certain pluripotency-specific marker genes. See, e.g., Silva et al., "Capturing pluripotency," Cell 132:532-536 (2008); and Toyooka et al., "Identification and characterization of subpopulations in undifferentiated ES cell culture," Development 135:909-918 (2008).

Therefore, RNA-based approaches for cell identification are limited by perturbations in gene expression caused by transient cell culture conditions, cell-to-cell heterogeneity in gene expression, and random degradation of mRNA in cell-derived extracts or samples that adversely affect the robustness, reproducibility, and interpretation of such techniques. As a result, biological and stochastic variability must be countered by intense bioinformatic analysis. In general, RNA-based arrays are useful discovery tools, but they are not yet widely applicable as a clinical or large scale assay method for the identification of cells. See, e.g., Miller et al., *Cancer Cell* 2:353-61 (2002); Nadon et al., *Trends Genet* 18:265-71 (2002); *Murphy D, Adv Physiol Educ,* 26:256-70, (2002).

In recent years, some markers for epigenetic modifications to chromatin, such as DNA methylation and histone acetylation, have been used to study and distinguish cells. Such approaches are based on the fact that higher organisms must impose and maintain different patterns of gene expression in various types of tissues and/or cells despite having essentially the same DNA sequence encoded by the genome of all cell types within the body of an individual. This is achieved largely through changes in chromatin structure caused in part by chemical modification of chromatin. Generally speaking, the most condensed chromatin domains, known as heterochromatin, are inaccessible to DNA binding factors and tend to be transcriptionally silent, whereas more extended chromatin domains, known as euchromatin, correspond to more accessible portions of the genome that tend to be transcriptionally active.

Therefore, assaying for various epigenetic modifications to chromatin within a collection of cells may provide a basis for distinguishing not only different types of cells, but normal versus transformed cells. For example, aberrant methylation of DNA frequently accompanies the transformation event from healthy to cancerous cells. Indeed, there are examples where specific methylation status may be used identify and/or distinguish various forms of cancer (see, e.g., Jones et al., Nature Genetics 21:163-167 (1999); Esteller et al., Oncogene 21:5427-5440 (2002); Laird et al., Nature Reviews Cancer 3:253-266 (2003)), as well as different stages and lineage commitments of normal cells (see, e.g., Attwood et al., CMLS 59:241-257 (2002)). However, these techniques based on epigenetic chemical modifications to identify cell states are limited by the fact that (1) they require very high resolution (200 bp nucleosomal units), (2) they reflect dynamic chromatin states that can change or become heterogeneous within a homogeneous cell type, (3) there is a large diversity of histone modifications that would need to be individually investigated to gain a comprehensive profile, and (4) these rely on the use of different and expensive antibodies and other reagents that would create challenges for high-throughput analysis.

Accordingly, new and improved methods for identifying and/or distinguishing cells are still needed.

SUMMARY

According to a first broad aspect of the present invention, a method for identifying cells is provided comprising the following steps: (a) hybridizing fluorescently labeled DNA from a population of cells to a genomic array having an average probe spacing of about 6 kb or less to determine a replication timing test profile for the population of cells; and (b) identifying the population of cells by comparing the replication timing test profile to a replication timing reference profile and determining whether the replication timing test profile and the replication timing reference profile are substantially the same.

According to a second broad aspect of the present invention, a method for distinguishing cells is provided comprising the following steps: (a) hybridizing fluorescently labeled DNA from a population of cells to a genomic array having an average probe spacing of about 6 kb or less to determine a replication timing test profile for the population of cells; and (b) distinguishing the population of cells from other cells by comparing the replication timing test profile to a replication timing reference profile to determine whether the replication timing test profile and the replication timing reference profile are substantially different.

According to a third broad aspect of the present invention, a method for identifying cells is provided comprising the following steps: (a) determining a replication timing test profile for a population of cells by quantifying an amount of replicated DNA in a sample derived from the population of cells by sequencing; and (b) identifying the population of cells by comparing the replication timing test profile to a replication timing reference profile and determining whether the replication timing test profile and the replication timing reference profile are substantially the same.

According to a fourth broad aspect of the present invention, a method for distinguishing cells is provided comprising the following steps: (a) determining a replication timing test profile for a population of cells by quantifying an amount of replicated DNA in a sample derived from the population of cells by sequencing; and (b) distinguishing the population of cells from other cells by comparing the replication timing test profile for the population of cells to a replication timing reference profile to determine whether the replication timing test profile and the replication timing reference profile are substantially different.

According to a fifth broad aspect of the present invention, a method for determining a replication timing fingerprint for a particular cell type is provided comprising the following steps: (a) hybridizing fluorescently labeled DNA from a population of cells of the particular cell type to a genomic array having an average probe spacing of 6 kb or less to determine a first replication timing profile for the population of cells; and (b) comparing the first replication timing profile for the population of cells to a second replication timing profile for cells of a different cell type to determine a replication timing fingerprint for the population of cells, wherein the replication timing fingerprint comprises one or more informative segments, wherein each informative segment of the replication timing fingerprint is defined as regions of about 50 kilobases (kb) or greater having a replication timing differential of about 0.5 or greater between the first replication timing profile and the second replication timing profile, and wherein the first and second replication timing profiles comprise replication timing ratio values equal to $\log_2$(early/late S-phase replication).

BRIEF DESCRIPTION OF THE DRAWINGS

FIG. 2A is a table providing validation of results from microarray experiments by PCR;

FIGS. 2B and 2B-1 together represent a table comparing the results from microarray experiments to a previously published replication-timing analysis of 46C ESCs by PCR (see, e.g., Hiratani et al., "Differentiation-induced replication-timing changes are restricted to AT-rich/long interspersed nuclear element (LINE)-rich isochores," PNAS USA 101:16861-16866 (2004), the entire contents and disclosure of which are hereby incorporated by reference), with PCR results classified as early (E) and late (L) based on the same criteria used in FIG. 2A.

FIGS. 2C and 2C-1 together represent a table comparing the results from microarray experiments to a previously published replication-timing analysis of OS25 ESCs by PCR (see, e.g., Perry et al., "A dynamic switch in the replication timing of key regulator genes in embryonic stem cells upon neural induction," Cell Cycle 3:1645-1650 (2004), the entire contents and disclosure of which are hereby incorporated by reference), with genes called E, ME, and M by Perry et al. classified as early (E) and with genes by Perry et al. called ML and L classified as late (L);

FIG. 6C is a table providing Pearson's $R^2$ values for pair-wise comparisons of NPCs derived from distinct neural differentiation schemes and three independent mESC lines;

FIG. 6J is a table summarizing replication domain sizes by chromosome with chromosome Y excluded from the analysis due to being under-represented on the microarray;

FIG. 7G is a table showing the mean size (Mb), % GC, % LINE-1, and gene density (RefSeq genes/Mb) of EtoL, LtoE, EtoE, and LtoL domain categories with domains having the 5% greatest replication timing changes defined as EtoL and LtoE, and with domains having the least replication timing changes (lowest 20 percentile) that maintain replication timing ratios above 0.5 or below −0.5 defined as EtoE and LtoL, respectively;

FIG. 7H is a table showing correlations of % GC, % LINE-1, and gene density with replication timing of domains in ESCs and NPCs expressed as Pearson's R.sup.2 values;

FIG. 8A is a graphical scatter plot showing average replication timing ratios of replication domains from ESCs plotted against their "present" (=transcriptionally active) gene density with Pearson's $R^2$ values shown;

FIG. 8B is a graphical scatter plot showing average replication timing ratios of replication domains from NPCs plotted against their 'present' (=transcriptionally active) gene density with Pearson's $R^2$ values shown;

FIG. 8C is a bar graph of "bins" of 100 genes ranked according to their replication timing ratios for ESCs with the width of each bin representing the range of replication timing ratios needed to achieve 100 genes per bin and the height of each bin representing the percentage of active (='present') genes within such bin, with logistic regression (inner line) and 95% confidence intervals (outer lines) shown;

FIG. 8D is a bar graph of "bins" of 100 genes ranked according to their replication timing ratios for NPCs with the width of each bin representing the range of replication timing ratios needed to achieve 100 genes per bin and the height of each bin representing the percentage of active (="present") genes within such bin, with logistic regression (inner line) and 95% confidence intervals (outer lines) shown;

FIG. 8G is a table providing a summary of expression patters of genes within LtoE, EtoL, LtoL and EtoE domains with "Up" and "Down" genes having above "two-fold up" or "two-fold down" regulation, respectively; "Unchanged" genes having below "two-fold up" or "two-fold down" regulation; "Unchanged Only" domains having only active and silent genes that change by less than two-fold; and "Silent Only" domains having only silent genes;

FIG. 10A is a graphical box plot showing the expression level of transcriptionally active ("present") genes with different promoter CpG densities (LCP, ICP and HCP representing low, intermediate, and high CpG promoters, respectively) based on Affymetrix GeneChip analysis of RefSeq genes, with horizontal bars representing the 10th, 25th, 50th (median), 75th, and 90th percentiles and P-values obtained from a two-tailed t-test for comparison of two unpaired groups shown;

FIG. 10B is a graphical box plot showing the fold changes in transcription [=$\log_2$(NPC/ESC)] of LCP, ICP, and HCP genes among EtoL genes, with horizontal bars representing the 10th, 25th, 50th (median), 75th, and 90th percentiles and P-values obtained from a two-tailed t-test for comparison of the two unpaired groups shown;

FIG. 10C is a graphical box plot showing the fold changes in transcription [=$\log_2$(NPC/ESC)] of LCP, ICP, and HCP genes among LtoE genes, with horizontal bars representing the 10th, 25th, 50th (median), 75th, and 90th percentiles and P-values obtained from a two-tailed t-test for comparison of two unpaired groups shown;

FIGS. 11A and 11A-1 together represent an upper set of graphical box plots providing the subnuclear position (i.e., radial distance) of 8 genomic regions as determined by 3D-FISH in ESCs and NPCs with 0 and 1 representing the periphery and the center of the nucleus, respectively, as well as a lower set of graphical plots providing replication timing profiles and the probe positions (red squares) for the same 8 genomic regions;

DETAILED DESCRIPTION OF THE PREFERRED EMBODIMENTS

Figure 1A:
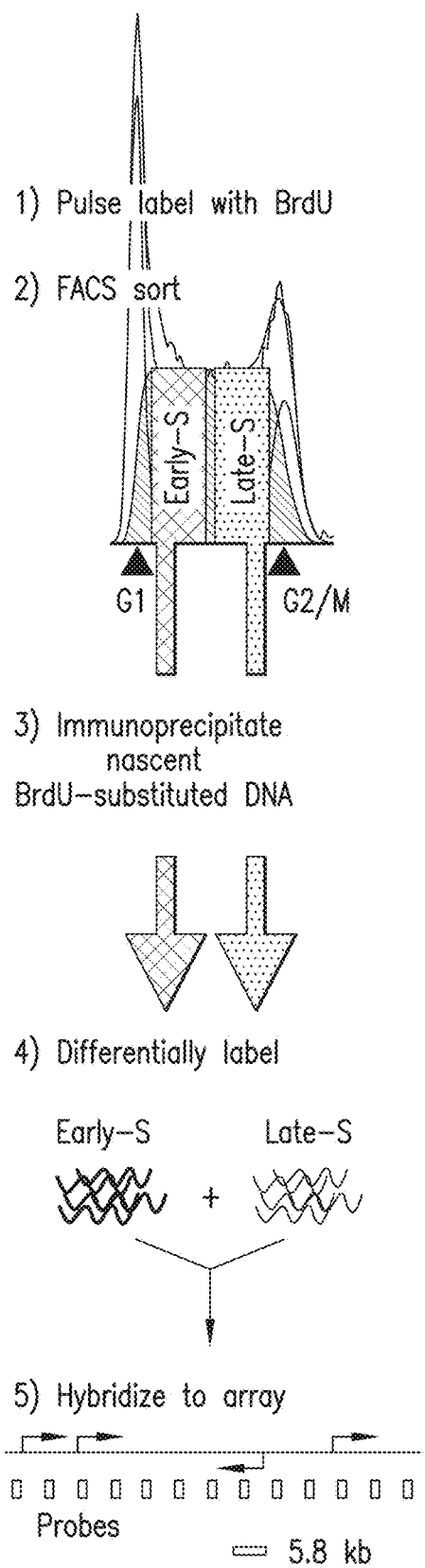
FIG. 1A is a schematic representation showing a protocol for genome-wide replication timing analysis using a 5.8 kb resolution oligonucleotide microarray.

Where the definition of terms departs from the commonly used meaning of the term, applicant intends to utilize the definitions provided below, unless specifically indicated.

For purposes of the present invention, the terms "epigenetics," "epigenetic markers," and "epigenetic parameters" generally refer to chemical modifications of DNA, histones, or other chromatin-associated molecules that impart changes in gene expression, such as methylation, acetylation, ubiquitylation, etc. However, the terms "epigenetics," "epigenetic markers," and "epigenetic parameters" may refer more generally to any changes in chromatin structure that affect gene expression apart from DNA sequence. For example, the terms "epigenetics," "epigenetic markers," and "epigenetic parameters" may refer to incorporation of histone variants or chromosomal remodeling by enzymes.

For purposes of the present invention, the terms "epigenetic signature" or "epigenetic signatures" broadly refer to any manifestation or phenotype of cells of a particular cell type that is believed to derive from the chromatin structure of such cells.

For purposes of the present invention, the term "replication timing ratio" refers to a ratio value for the timing of replication at a particular locus of a chromosome within the genome of a cell. For example, the "replication timing ratio" may be a ratio of the extent of replication in early S-phase cells divided by the extent of replication in late S-phase cells, or vice versa, at a given locus. Alternatively, the replication timing ratio may be expressed on a logarithmic scale, such as $\log_2$(early/late) or $\log_2$(late/early). Alternatively, for example, the term "replication timing ratio" may refer to the ratio of the extent of replicated DNA in S-phase cells to the amount of DNA in G1-phase cells. The extent of replication or the amount of DNA may be measured, for example, by the fluorescence intensity of an attached label.

For purposes of the present invention, the term "replication timing domain" refers to a contiguous region of a chromosome of a cell or population of cells having a roughly the same (i.e., early vs. late) replication timing, such as a contiguous region of a chromosome of a cell or population of cells having a roughly equal replication timing ratio value.

For purposes of the present invention, the term "replication timing profile" refers to a series of values for replication timing (e.g., early versus late S-phase replication timing) along the length of at least a segment of one or more chromosome(s) within a genome. For example, the "replication timing profile" may be expressed as a series of replication timing ratio values, such as early/late S-phase replication or late/early S-phase replication, along the length of at least a segment of one or more chromosome(s), which may further be expressed on a logarithmic scale. Alternatively, the "replication timing profile" may refer to a ratio of the amounts of S-phase DNA to G1-phase DNA from a population of asynchronously dividing cells along the length of at least a segment of one or more chromosome(s), which may further be expressed on a logarithmic scale, with a higher ratio indicating earlier replication and a lower ratio indicating later replication. The term "replication timing profile" may include a replication timing fingerprint for a particular cell type or a set of replication timing profiles for informative segments of a replication timing fingerprint for a particular cell type. The term "replication timing profile" may further include a replication timing profile differential between any combination of: (1) one or more replication timing profile(s); (2) a replication timing fingerprint; and/or (3) one or more informative segment(s) of a replication timing fingerprint(s). The "replication timing profile" may be determined, for example, by quantifying an amount of replicated DNA in a sample from a population of cells by measuring fluorescently labeled DNA, by sequencing, etc.

For purposes of the present invention, the term "replication timing test profile" refers to the replication timing profile for a population of cells of interest having an unknown or uncertain identity to the user of the embodiments of the methods of the present invention.

For purposes of the present invention, the term "replication timing reference profile" refers to a replication timing profile used as a basis for comparison to identify and/or distinguish a population of cells based on its replication timing test profile. Such "replication timing reference profile" may include a replication timing profile for a population of cells, an average replication timing profile for a group of related or identical cells or from replicate experiments, a replication timing fingerprint, one or more informative segment(s) of a replication timing fingerprint, etc., or any combination thereof. Such a "replication timing reference profile" may be simultaneously or previously determined, may be contained in a database, etc.

For purposes of the present invention, the terms "differential," "replication timing profile differential," or "replication timing differential" refer interchangeably to differences in replication timing values between any combination of: (1) one or more replication timing profile(s); (2) a replication timing fingerprint; and/or (3) one or more informative segment(s) of a replication timing fingerprint. For example, the "replication timing differential" may refer to differences in replication timing ratios, such as differences in replication timing ratios expressed on a logarithmic scale, between two or more populations of cells or cell types at a given genomic or chromosomal locus or along the length of at least a segment of one or more chromosome(s) within a genome, etc.

For purposes of the present invention, the term "replication timing fingerprint" refers to one or more segments or portions of a replication timing profile for a particular type of cell(s) that differs from all other cell types or all other relevant cell types, which may be used to identify, distinguish, etc., cells of that type. The term "replication timing fingerprint" may refer to the collection of all informative segments of a genome of cells of a particular cell type defined as segments that display a replication timing profile that differs from the replication timing profiles of one or more other cell types. The term "replication timing fingerprint" may further include one or more informative segment(s) that have replication timing profiles that are shared by two or more cell types (i.e., the replication timing profiles are identical or similar) for purposes of comparing a population of cells to a limited set of candidate cell types that have a different replication timing profile for such informative segment(s). A "replication timing fingerprint" may generally exclude uninformative segments that are not consistent among cells of the same type or that do not differ among cells of different types.

The terms "informative segment" or "informative segments" refer to one or more contiguous portions or segments of one or more chromosome(s) within a genome that are used to define a replication timing fingerprint. In other words, the terms "informative segment" or "informative segments" may refer to one or more contiguous portions or segments of one or more chromosome(s) within a genome that differ between two or more different cell types. For example, the terms "informative segment" or "informative segments" may refer to one or more regions or segments of a genome for a population of cells of a particular cell type having the following characteristics: (1) the region covers at least about 50 kilobases (kb) of genomic DNA; and (2) the region has at least about a 0.5 replication timing ratio differential across such length compared to all other cell types, or at least compared to all other relevant cell types.

For purposes of the present invention, the term "population of cells" refers to a homogeneous group or population of cells. The term "population of cells" may also include a single cell in culture having the potential to grow and divide into a plurality of homogeneous cells under appropriate culturing conditions.

For purposes of the present invention, the term "primary cell" refers to a cell or cells isolated from a tissue of an organism and placed in culture. The "primary cell" may be derived from any tissue of any organism, such as a mammalian organism. The term "primary cell" generally includes any cell or cells that may be isolated from a tissue of an organism to create a reasonably homogeneous population of cells, such as by first creating single cell suspensions.

For purposes of the present invention, the term "mammalian cells" refers to a population of cells that are, or were, originally derived from a mammalian organism. The term "mammalian cells" may include primary cells derived from a mammalian species or a cell line originally derived from a mammalian species. The term "mammalian cells" may refer to a homogeneous population of cells from a mammalian organism.

For purposes of the present invention, the term "cell type" refers to the kind, identity, and/or classification of cells according to any and all criteria, such as their tissue and species of origin, their differentiation state, whether or not (and in what manner) they are normal or diseased, etc. For example, the term "cell type" may refer separately and specifically to any specific kind of cell found in nature, such as an embryonic stem cell, a neural precursor cell, a myoblast, a mesodermal cell, etc. Such a list of possible cell types is meant herein to be unlimited.

For purposes of the present invention, the terms "array" or "microarray," when used to determine the replication timing profile for a population of cells, refer interchangeably to a field or array of a multitude of spots corresponding to nucleic acid probes or oligonucleotides for all or at least a portion of the genome of a species placed on a support or substrate to allow for simultaneous detection and/or quantification of nucleic acid molecules present in one or more sample(s) by hybridization as commonly understood in the art. For purposes of the present invention, the term "array" generally refers to a genomic array, such as a comparative genomic hybridization (CGH) array, a tiling array, etc.

For purposes of the present invention, a "genomic array" is an array having probes and/or oligonucleotides corresponding to both coding and non-coding intergenic sequences for at least a portion of a genome and may include the whole genome of an organism. For example, a "genomic array" may have probes and/or oligonucleotides for only portions of a genome of an organism that correspond to replication timing fingerprint(s) or informative segments of fingerprint(s). The term "genomic array" may also refer to a set of nucleic acid probes or oligonucleotides representing sequences that are about evenly spaced along the length of each chromosome or chromosomal segment. However, even spacing of probes may be dispensable with very high density genomic arrays (i.e., genomic arrays having an average probe spacing of much less than about 6 kilobases).

For purposes of the present invention, the term "high resolution array" or "high resolution genomic array" generally refers a genomic array having sufficient resolution to provide enough information to generate a smooth replication timing profile to reliably determine the exact positions, lengths, boundaries, etc., of the replication timing domains. The term "high resolution array" or "high resolution genomic array" may correspond to the whole genome or a substantial portion of a genome of a particular cell or population of cells. The term "high resolution array" or "high resolution genomic array" may also refer to a genomic array having an average probe spacing of about 6 kilobases (kb) or less.

For purposes of the present invention, the term "spot" refers to an area, region, etc. of the surface of a support, substrate, etc., having identical, similar, and/or related nucleic acid probe or oligonucleotide sequences. Such nucleic acid probes may include vectors, such as BACs, PACs, etc. Each "spot" may be arranged so that it does not touch, become indistinguishable, or become continuous with other adjacent spots.

For purposes of the present invention, the term "resolution," with reference to arrays, refers to how much resolution may be achieved along the length of one or more chromosomes. In general, the more probes and/or oligonucleotides along a given length of a chromosome, the greater or higher the resolution may be for such length of a chromosome, assuming roughly equal spacing. Therefore, the terms "density" or "probe density" for an array are directly related to the term "resolution" since a greater or higher probe density along a given length of a chromosome would generally result in greater or higher resolution for the same length of a chromosome. Conversely, the term "spacing" or "probe spacing" is inversely related to gene density and resolution for an array since a lower or reduced spacing on average between probes and/or oligonucleotides on the array as a function of chromosomal position would generally result in greater or higher resolution or probe density. For example, an array having an average "probe spacing" of about 6 kb or less along a length of a chromosome would have a "probe density" or "resolution" of about 6 kb or higher for such length of chromosome.

For purposes of the present invention, the terms "genome-wide" or "whole genome" may refer interchangeably to the entire genome of a cell or population of cells. Alternatively, the terms "genome-wide" or "whole genome" may refer to most or nearly all of the genome. For example, the terms "genome-wide" or "whole genome" may exclude a few portions of the genome that are difficult to sequence, do not differ among cells or cell types, are not represented on a whole genome array, or raise some other issue or difficulty that prompts exclusion of such portions of the genome.

DESCRIPTION

DNA replication is regulated via the coordinate firing of clusters of replicons that duplicate megabase-sized chromosome segments at specific times during S-phase. Cytogenetic studies show that these "replicon clusters" coalesce as sub-chromosomal units or domains that persist through multiple cell generations. Replicon clusters can be visualized in living cells as discrete foci by pulse labeling with fluorescent nucleotide analogs. When followed through multiple cell divisions, labeled foci do not mix, separate or change in shape, indicating that the DNA that replicates coordinately derives from a single chromosome segment. In general it is thought that adjacent replication origins form what is known as a replicon cluster. These replicon clusters replicate within 45-60 minutes and encompass approximately 500 kilobases, and several adjacent replicon clusters coalesce to form coordinate multi-megabase "replication domains" that replicate within 1-2 hours. (see, e.g., Sadoni et al., "Stable chromosomal units determine the spatial and temporal organization of DNA replication," J. Cell Sci. 117:5353-5365 (2004); Dimitrova et al., "The spatial position and replication timing of chromosomal domains are both established in early G1-phase," Mol Cell. 4:983-993 (1999); Ma et al., "Spatial and temporal dynamics of DNA replication sites in mammalian cells," J. Cell Biol. 143: 1415-1425 (1998); Jackson et al., "Replicon clusters are stable units of chromosome structure: evidence that nuclear organization contributes to the efficient activation and propagation of S phase in human cells," J. Cell Biol. 140:1285-1295 (1998); and Sporbert et al., "DNA polymerase clamp shows little turnover at established replication sites but sequential de novo assembly at adjacent origin clusters," Mol. Cell 10:1355-1365 (2002), the entire contents and disclosures of which are hereby incorporated by reference). So far, however, many details concerning the molecular properties of such domains remain unknown.

Embodiments of the present invention provide methods for identifying and/or distinguishing a population of cells from other cells or populations of cells on the basis of their replication timing profiles obtained by querying a high resolution genomic array. This approach is founded on several discoveries described herein recognizing that replication timing profiles are both stable and reproducible for a particular population of cells and that replication timing profiles differ among different cell types.

Others have attempted to characterize replication timing in various cell types. For example, several studies have determined replication timing of several genomic loci by targeted PCR from samples that contain fragments of replicated DNA purified by immunoprecipitation from cells sorted into various cell cycle fractions. See, e.g., Perry et al., "A dynamic switch in the replication timing of key regulator genes in embryonic stem cells upon neural induction," Cell Cycle 3: 1645-1650 (2004); Azuara et al., "Chromatin signatures of pluripotent cell lines," Nat. Cell Biol. 8:532-538 (2006); Azuara et al., "Heritable gene silencing in lymphocytes delays chromatid resolution without affecting the timing of DNA replication," Nat. Cell Biol. 5(7):668-674 (2003); Azuara V., "Profiling of DNA replication timing in unsynchronized cell populations," Nat. Protoc. 1(4):2171-2177 (2006); and Hiratani et al., "Differentiation-induced replication-timing changes are restricted to AT-rich/long interspersed nuclear element (LINE)-rich isochores," PNAS USA 101:16861-16866 (2004)). However, the PCR-based methods described in these references are only able to determine replication timing at the few discrete genomic loci that happen to be directly tested by PCR. Such methods would not be able to generate a smooth and continuous replication timing profile for a population of cells, which is necessary to determine the exact positions, lengths, and boundaries of replication timing domains. Accordingly, those in the art would not be able to use the PCR-based methods from the above references to accurately and reliably identify and/or distinguish cells on the basis of the exact positions, lengths and boundaries of their replication timing domains.

With existing technology, the only known way to construct a replication timing profile for a population of cells that is able to reliably discern the exact positions, lengths, and boundaries of replication domains in a high-throughput manner over a large portion of the genome of cells from higher organisms is to subject some form of replicated DNA to analysis using a high-resolution genomic array. However, previous reports have not described a genome-wide analysis of replication timing of cells using high-resolution arrays.

Other groups have carried out genome-wide timing of replication using only low-density arrays. For example, in Schubeler et al., "Genome-wide DNA replication profile for *Drosophila melanogaster*: a link between transcription and replication timing," Nat. Genet. 32:438-442 (2002), labeled replicated DNA was subjected to a DNA array that queried only 5,221 sequences having an average chromosomal distance of 20.5 kb, and some probes had a chromosomal distance of 100 kb or greater. In Woodfine et al., "Replication timing of the human genome," Hum. Mol Genet. 13:191-202 (2004), replication timing was determined at only 1 Mb resolution. However, such low-density arrays are unable to generate sufficient information or resolution to accurately and reliably determine the exact positions, lengths, and boundaries of replication timing domains. In fact, a later publication by the same author (see, Woodfine et al., "Replication Timing of Human Chromosome 6," Cell Cycle 4:172-176 (2005)) showed that the 1 Mb resolution array is not capable of discerning all early and late replicating domains.

Other groups have described the study of replication timing in cells using higher density arrays. However, those studies focused on only a portion or segment of a chromosome and not the whole-genome. For example, White et al., "DNA replication-timing analysis of human chromosome 22 at high resolution and different developmental states," PNAS USA 101:17771-17776 (2004) only investigated replication timing of human chromosome 22; MacAlpine et al., "Coordination of replication and transcription along a *Drosophila* chromosome," Genes. Dev. 18:3094-3105 (2004) only studied replication timing for the left arm of chromosome 2 in *Drosophila*; and Woodfine et al., "Replication Timing of Human Chromosome 6." Cell Cycle 4:172-176 (2005) only queried human chromosome 6. In many circumstances, however, a replication timing profile for only a segment or region of a chromosome or only a portion of a genome may be insufficient to accurately and reliably identify a population of cells and/or distinguish a population of cells from other cells.

Importantly, other groups have not explicitly suggested or even contemplated the potential use of high-resolution replication timing profiles as an accurate and reliable means to determine the identity of a population of cells and/or to distinguish the identity of a population of cells from other cells or cell types, as proposed herein by embodiments of the present invention. At most, other groups have only compared replication timing of cells for purposes of study and not as a means to identify and/or distinguish the identity of a population of cells, determine replication timing fingerprints for a particular cell type, etc. In fact, the only published report to actually compare replication timing profiles of different cell types using high-density arrays concluded that the two cell types compared are remarkably similar (see, White et al., "DNA replication-timing analysis of human chromosome 22 at high resolution and different developmental states. PNAS USA 101:17771-17776 (2004)), which suggests that high-resolution replication timing profiles may not be usable to identify cells and/or distinguish different populations of cells, cell types, determine replication timing fingerprints, etc. For example, it is described herein that as much as 20% of the genome changes replication timing upon neural differentiation of mouse embryonic stem cells (ESCs) into neural precursor cells (NPCs), while replication domain boundaries remain remarkably conserved between genetically polymorphic ESCs, thus indicating that replication timing profiles may serve as stable and reliable epigenetic signatures for different types of cells.

Embodiments of the present invention rely on the novel concept that replication timing profiles may be used to accurately and reliably identify a population of cells and/or distinguish a population of cells from others. Embodiments of the present invention are based at least partially on the underlying and fundamental discoveries described herein that the replication timing profile for a particular cell type or homogeneous population of cells is extremely stable and reproducible through generations of cell cycles and that such replication timing profiles differ among different cell types. Significantly, such replication timing profiles appear to be related to chromatin states of particular populations of cells and not directly related to or affected by transcription levels.

Embodiments of the present invention are based primarily on three discoveries described further herein. First, cells of the same type display nearly identical patterns of replication timing domains regardless of how individual cell lines of the same type are generated and/or maintained. For example, different mouse embryonic stem cell (ESC) lines generated according to different procedures and having different maintenance histories show remarkably similar patterns or profiles of replication timing domains. Indeed, a de-differentiated population of cells, called induced pluripotent stem (iPS) cells, also show remarkable similarity in their pattern of replication timing domains compared to ESCs.

Second, different types of cells, even cells from the same lineage at different stages of development, show divergent and distinguishable patterns or profiles of replication timing domains. For example, as described further below, neural precursor cells (NPCs) display different and distinguishable replication timing profiles than ESCs from which they derive.

Third, and as described hereafter, there is the highly useful insight that a comparative genomic (CGH) array having a resolution of about 6 kb (or higher) is sufficient to generate smooth and continuous replication timing profiles for a cell that is capable of identifying, distinguishing, etc., even small replication timing domains, including reliably discerning the exact positions, lengths, boundaries, etc., of such replication domains. As described below, an approximately 100 base pair resolution tiling array did not generate any greater saturation of information concerning the number and/or resolution of replication timing domain positions, lengths, or boundaries. With existing technology, such insight provides the valuable advantage of conveniently and economically allowing the replication timing profile for the whole genome of a homogeneous population of cells to be queried on a single array, as opposed to multiple arrays as would be for tiling arrays covering the whole genome.

According to embodiments of the present invention, methods are provided for identifying and/or distinguishing cells on the basis of their replication timing profiles. In a first step, the replication timing profile of a population of cells is determined based on information about the timing of replication (i.e., early S-phase versus late S-phase replication) occurring in the population of cells. In a second step, the replication timing test profile for the population of cells is compared to a replication timing reference profile (or a replication timing fingerprint) to identify the population of cells and/or distinguish the population of cells from other cells. As described further herein, replication timing profiles may be further used to generate replication timing fingerprints for distinct populations of cells or cell types.

Step 1: Determining a Replication Timing Profile for a Population of Cells

According to a first step of embodiments of the present methods, a replication timing profile may be determined for a cell or population of cells according to embodiments of the present methods for an entire genome, one or more chromosomes, or one or more segments of a chromosome or set of chromosomes depending upon the circumstances. According to some embodiments, for example, a replication timing profile for only a segment of a chromosome or for fewer than all chromosomes, such as a segment or segments containing a sufficient number of replication timing fingerprints for a particular cell type (see below), may be sufficient to identify and/or distinguish the population of cells from other cells. According to other embodiments, for example, generation of a replication timing profile for the entire genome of a population of cells may be required to identify and/or distinguish the population of cells from other cells. Due to the relative ease of generating a replication timing profile for the entire genome of a cell on a single array of sufficiently high resolution, embodiments of the present methods may determine the replication timing profile for the entire genome in the first step.

At a minimum, any array used to determine the replication timing profile for the population of cells should have a sufficient resolution to determine the positions, size, boundaries, etc., of early S-phase and late S-phase replication timing domains for at least a segment of the genome, if not the whole genome, for the population of cells. Therefore, for reasons explained further herein, embodiments of the present methods will generally rely on the use of genomic arrays having a resolution or density of about 6 kb or higher (i.e., an average probe spacing of about 6 kb or less) shown to have sufficient resolution to accurately and reliably determine the positions, lengths, boundaries, etc., of replication timing domains.

A population of cells that may be analyzed according to embodiments of the present methods may include any type of cell from any species that is capable of growing and dividing (i.e., proliferating) in a culture medium. Such a population of cells may include, for example, any cell line or any sample of primary cells, such as any cell or population of cells derived from a tissue, biopsy, blood, sputum, saliva, urine collections, etc., or obtained by a medical procedure. For example, such a population of cells may include any cells that are grown in suspension, as adherent cultures, as embryoid bodies, as tissue or organ culture, etc. Such a population of cells may be derived from any organism. For example, such cell(s) or population of cells may be derived from a mammalian species, such as a human. A population of cells that may be analyzed according to embodiments of the present methods may further include embryonic cells, such as embryonic stem cells (ESCs) or other non-differentiated or precursor cells, or cells that have been de-differentiated from cells derived from somatic tissues or from a differentiated cell line, such as induced pluripotent stem (iPS) cells. Alternatively, such a population of cells may include differentiated cells. A cell(s) or population of cells that may be analyzed according to embodiments of the present methods may also include normal cells, diseased cells, cancerous cells, tumor cells, transformed cells, etc. To ensure accuracy and reliability in determining a replication timing profile for a population of cells, it may be necessary that the population of cells analyzed by embodiments of the present methods be derived from a single cell and/or be free of contamination of other cell types. Therefore, care may need to be taken in culturing cells to ensure their homogeneity or near homogeneity of the cells.

The replication timing profile for a population of cells may be determined using any method that may accurately and reliably discern the positions, lengths, boundaries, etc., of replication timing domains. For example, a replication timing profile may be determined by: (i) an early/late S-phase method; (ii) a G1-phase/S-phase method; or (iii) a synchronization method. All embodiments of the present methods may be performed in replicate to improve statistical analysis and to allow the determination of average values and deviations as well as the removal of outliers and artifacts. In general, data obtained by embodiments of any of the present methods may also be normalized and subjected to polynomial (loess) smoothing to improve analysis and comparison. Furthermore, different methods and embodiments of the present invention described below may be used in combination to improve the accuracy and reliability of replication timing profiles.

Early/Late S-phase Method for Determining Replication Timing

According to some embodiments of the present methods, an "Early/Late S-phase" method may be used to determine the replication timing profile for an asynchronous population of cells. Briefly, a population of cells may be cultured in a growth medium containing a modified nucleotide for a predetermined period of time. The modified nucleotide may be incorporated into regions of the genome of S-phase cells that happen to be undergoing DNA replication during that time. Next, the population of cells may be separated into a population of early S-phase cells and a population of late S-phase cells based on the amount of total DNA content per cell. Once early and late S-phase cells are separated, replicated DNA may be obtained from samples derived from both early and late S-phase cells on the basis of the incorporated modified nucleotide. To distinguish replicated DNA from each of the two cell populations, replicated DNA from early S-phase cells and replicated DNA from late S-phase cells may be differentially labeled with fluorescent labels. Finally, the differentially labeled samples of replicated DNA may be hybridized to a nucleic acid array to determine the relative amount of replication occurring at each genomic loci represented on the array in early versus late S-phase cells based on the strength of fluorescence. Once the amounts of replication occurring in each of the distinct populations of S-phase cells are determined, such data may be normalized and used to generate a smooth replication timing profile along the length of each chromosome queried.

For a description of related methods that may be useful in embodiments of the present methods, see, e.g., Hiratani et al., "Differentiation-induced replication-timing changes are restricted to AT-rich/long interspersed nuclear element (LINE)-rich isochors." *PNAS* 101:16861-16866 (2004); Schubeler et al., "Genome-wide DNA replication profile for *Drosophila melanogaster*: a link between transcription and replication timing." *Nat. Genet.* 32:438-442 (2002); White et al., "DNA replication timing analysis of human chromosome 22 at high resolution and different developmental states." *PNAS USA* 101:17771-17776 (2004); and Hiratani et. al, "Global Re-organization of replication domains during embryonic stem cell differentiation." *PlosBiology*, in press (2008), the entire contents and disclosures of which are hereby incorporated by reference.

According to embodiments of the present methods, cells or populations of cells may be grown in a culture medium containing a modified nucleotide. For example, cells may be grown in suspension or as adherent cells or embryoid bodies. Any medium appropriate for growth of a particular population of cells may be used in present methods. Specific mediums that are appropriate for growth of particular populations of cells are known in the art may be used. Adherent cells may be trypsinized to detach them from the surface and allow their isolation into single cell suspensions.

The modified nucleotide is capable of incorporating into regions of the genome of cells that are undergoing replication during the time of exposure. Only specific regions of the genome of S-phase cells that are undergoing replication during that time will incorporate the modified nucleotide. Depending upon the portion of S-phase that overlaps with the timing or window of exposure to the modified nucleotide, different regions of the genome may incorporate the modified nucleotide. Only those regions of genome that happen to be undergoing replication during that time of exposure will incorporate the modified nucleotide. For example, early S-phase cells may have a different pattern of replication, and hence a different pattern of incorporation of the modified nucleotide, compared to late S-phase cells. By incorporating the modified nucleotide into sites of replication within the genome of a cell, these regions of replication may later be isolated and identified. The length of time for exposure to the modified nucleotide may be predetermined and may depend on various circumstances, such as the culturing conditions and/or type of cells being analyzed. For example, the timing or window of exposure may be modified according to the length of S-phase for a given cell or population of cells. Generally, it has been found that an exposure time of from about 1 to about 2 hours is effective; however, other exposure times may be used as needed for particular populations of cells as the case may be.

The modified nucleotide placed in the culturing medium according to embodiments of the present methods may be any modified nucleotide that enables later detection, isolation, separation, analysis, or identification. For example, the modified nucleotide may be chemically modified or labeled such that it is capable of being selectively bound by an antibody, another molecule, etc. Alternatively, for example, the modified nucleotide may be directly or covalently attached to a label, such as a fluorescent label. However, incorporation of fluorescently labeled nucleotides may require permeabilization of the cells. According to some embodiments, for example, the chemically modified nucleotide may include biotinylated nucleotides that may later be purified, isolated, or extracted using avidin, Extravidin (Sigma), NeutrAvidin (Thermo Scientific), NeutraLite (Belovo), or strepavidin. However, while biotinylated nucleotides may be successfully used, they may have the drawback of requiring permeabilization of cells to allow their incorporation. According to some embodiments of the present methods, the modified nucleotide may be bromodeoxyuridine (BrdU). However, other modified deoxyuridine nucleotides may also be used, such as, for example, iododeoxyuridine (IdU), chlorodeoxyuridine (CldU), 5-ethynyl-2'-deoxyuridine (EdU), etc. See, e.g., Buck et al., "Detection of S-phase cell cycle progression using 5-ethynyl-2'-deoxyuridine incorporation with click chemistry, an alternative to using 5-bromo-2'-deoxyuridine antibodies." *Biotechniques* 44(7):927-9 (2008), the entire contents and disclosure of which is hereby incorporated by reference. According to some embodiments of the present methods, the concentration of BrdU may be varied or optimized depending on the culturing conditions and/or specific cell type. According to some embodiments, the concentration of BrdU in the growth culture medium may be approximately 50 µM BrdU.

According to some embodiments of the present methods, once the cells have been cultured in the presence of the modified nucleotide for a predetermined period of time, the cells may be sorted into separate populations of early S-phase and late S-phase cells on the basis of DNA content. Cells may be separated into early and late S-phase fractions by, for example, fluorescence activated cell sorting (FACS). Other methods known in the art for separating or sorting cells into different fractions of early-replicating S-phase and late-replicating S-phase may also be used. For example, antibodies that bind target proteins expressed only during specific stages of the cell cycle may be used to selectively bind and elute cells in such stages of the cell cycle. See, e.g., Oliver et al., *J. Oral Pathol. Med.* 29(9):426-431 (2000). Alternatively, centrifugal elutriation may potentially be used although it is cumbersome and expensive compared to FACS.

For FACS sorting, the cells may be washed, lightly fixed (e.g., by ethanol), and suspended into a solution, such as PBS, to achieve a desired concentration of cells (e.g., at least about $1.0 \times 10^6$ cells/ml). For the early/late S-phase method, sorting may require starting populations of at least about 3 million cells for populations having about 30% or more cells in S-phase; greater numbers may be required for cell populations having lower percentages of cells in S-phase. For adherent cultures or masses of cells, such cells should first be detached from the substrate and from surrounding cells to allow their suspension, such as by trypsinization. To allow FACS analysis to separate populations of early and late S-phase cells based on the amount of DNA content, the population cells may first be labeled, for example, with a DNA-labeling fluorescent dye. Any fluorescent DNA-labeling dye known in the art may potentially be used. For example, the DNA-labeling fluorescent dye may be Hoechst, chromomycin, DAPI, propidium iodide (PI), mithramycin, etc. For example, cells may be stained with about 50 μg/ml PI for 30 minutes in the presence of RNAseA (0.5 mg/ml). Alternatively, for example, Hoechst staining has the advantage of being used with live cells rather than requiring fixation. Procedures for using flow cytometry or FACS to separate cells on the basis of cell cycle stage, such as early- and late-replicating S-phase cells, are known in the art. See, e.g., Gilbert et al., "Temporal order of replication of *Xenopus laevis* 5S ribosomal RNA genes in somatic cells," *PNAS* 83:2924-2928 (1986); Gilbert et al., "Bovine papilloma virus plasmids replicate randomly in mouse fibroblasts throughout S phase of the cell cycle," *Cell* 50:59-68 (1987); and Hiratani et al., "Differentiation-induced replication-timing changes are restricted to AT-rich/long interspersed nuclear element (LINE)-rich iso chores," *PNAS* 101:16861-16866 (2004), the entire contents and disclosures of which are hereby incorporated by reference.

According to some embodiments of the present methods, the exact composition of cells that comprise the selected or sorted populations of early-replicating and late-replicating S-phase cells may be controlled to an extent by adjusting the gating limits for the two populations of cells. Such early and late S-phase fractions may include any range or fraction of S-phase cells as long as there is sufficient separation between the two fractions. According to some embodiments, the ranges for the two fractions may be approximately equal. For example, early-replicating S-phase cells and late-replicating S-phase cells may be selected by gating the lowest two-fifths and highest two-fifths of cells in S-phase, respectively, based on DNA-labeling fluorescent dye intensity. Alternatively, for example, early-replicating S-phase cells and late-replicating S-phase cells may be selected by gating the lowest one-third and highest one-third of cells in S-phase, respectively, based on DNA-labeling fluorescent dye intensity. In most cells, the total population of S-phase cells may be defined as greater than 2N but less than 4N DNA content per cell. However, some cell types may have different ranges due to having ploidy greater or less than 2N during interphase. Exact ranges of signal intensity that correspond to cells in S-phase may depend on the particular population of cells being analyzed and the labeling dye used. Such ranges may be established by any known methods or standards.

According to some embodiments, a two-dimensional FACS procedure may be used instead of relying on only one DNA-labeling fluorescent dye. According to this approach, cells may be sorted on the basis of both a DNA-labeling fluorescent dye (as described above) and a second label for the modified nucleotide incorporated into replicated DNA, such as with a fluorescently labeled antibody. Any two fluorescent labels may be used if they have sufficiently different emission wavelengths of light to ensure their independent analysis. For example, DNA content may be labeled with a red-fluorescing dye (e.g., propidium iodide) and the modified nucleotide (e.g., BrdU) may be labeled with a green-fluorescing dye (e.g., FITC labeled antibody bound to anti-BrdU antibody). When these cells are subjected to two-dimensional FACS, cells are sorted on the basis of both labels. For example, G1-phase cells would be expected to generally have lower DNA-labeling fluorescent dye (e.g., propidium iodide) and little, if any, labeling of the modified nucleotide (e.g., labeled anti-BrdU). By contrast, early S-phase cells would be expected to generally have lower DNA-labeling fluorescent dye (e.g., propidium iodide) but higher amounts of labeling of the modified nucleotide (e.g., labeled anti-BrdU), while late S-phase cells would be expected to generally have higher DNA-labeling fluorescent dye (e.g., propidium iodide) as well as higher amounts of labeling of the modified nucleotide (e.g., labeled anti-BrdU). Finally, G2- and M-phase cells would be expected to generally have higher DNA-labeling fluorescent dye (e.g., propidium iodide), but lower amounts of labeling of the modified nucleotide (e.g., labeled anti-BrdU).

Therefore, the precision and/or accuracy of separation of early and late S-phase cells by two-dimensional FACS may be improved compared to one-dimensional FACS based on only a DNA-labeling dye. For example, G1-cells may have greater separation from early S-phase cells, and late S-phase cells may have greater separation from G2/M-phase cells. To further improve results using two-dimensional FACS, controls and standards (e.g., labeling only one or the other) may be performed to correct any skewing caused by spectral overlap that may occur between the two labeling dyes (e.g., by subtracting such overlap from the analysis), and the FACS settings may be set to optimize separation between the different fractions of cells (e.g., by adjusting gains for each fluorescence channel).

According to some embodiments of the present methods, after separation of cells into early-replicating and late-replicating S-phase fractions, it may be necessary to isolate DNA from the distinct populations of early and late S-phase cells. Methods for isolating DNA are known in the art. See, e.g., Hiratani et al., "Differentiation-induced replication-timing changes are restricted to AT-rich/long interspersed nuclear element (LINE)-rich isochors," *PNAS* 101:16861-16866 (2004); Hansen et al., "Association of fragile X syndrome with delayed replication of the FMR1 gene," *Cell* 73:1403-1409 (1993); and Cimbora et al., "Long-Distance Control of Origin Choice and Replication Timing in the Human β-Globin Locus Are Independent of the Locus Control Region," *Mol. Cell Biol.* 20:5581-5591 (2000), the entire contents and disclosures of which are hereby incorporated by reference. For example, the cells may be lysed in SDS-PK buffer (1M NaCl; 10 mM EDTA; 50 mM Tris-HCl, pH 8.0; 0.5% SDS; 0.2 mg/ml PK; 50 μg/ml glycogen), and the DNA may be extracted by phenol/chloroform extraction followed by ethanol precipitation.

According to some embodiments of the present methods, once total DNA is isolated from the distinct populations of early and late S-phase cells, DNA segments of the genome of cells that replicated during the time window of exposure to the modified nucleotide may be isolated. However, to allow separate analysis of replicated DNA apart from non-replicated DNA, it may be necessary to break up the genomes of cells into smaller fragments that may be selected and isolated from each other. The genome may be sufficiently fragmented to allow fine resolution of replication timing along the length of each chromosome. For example, the average size of DNA fragments may be about 2 kb or less. Alternatively, the average size of DNA fragments may be about 1 kb or less, or in some cases, in the range of from about 200 to about 800 bps. According to some embodiments, the isolated DNA from each population of cells may be fragmented by subjecting the isolated DNA to sonication for a period of time. Alternatively, other methods of fragmentation may be used, such as restriction digestion, physical shearing by syringe, etc. However, sonication may be an advantageous method since it is relatively easy to use and is believed to generate a fairly uniform distribution of small fragments.

According to some embodiments of the present methods, once DNA is isolated from the distinct populations of early and late S-phase cells and fragmented into small segments of DNA, it may be necessary to isolate only those DNA fragments containing sequences that replicated during the period of exposure to the modified nucleotide. Such fragments of replicated DNA from each population of early and late S-phase cells may be isolated from the remaining DNA on the basis of incorporation of the modified nucleotide. Such an isolation of replicated DNA fragments may be achieved by any known method that selectively isolates DNA fragments on the basis of the modified nucleotide incorporated into regions of the genome corresponding to such fragments. For example, according to some embodiments, if the modified nucleotide is a biotinylated nucleotide, DNA fragments may be isolated from the non-replicated DNA by binding to another molecule, for example, avidin, streptavidin, etc., attached to a substrate, such as beads. According to other embodiments, for example, an antibody for the modified nucleotide, such as an anti-BrdU antibody where BrdU is used as the modified nucleotide, may be used to isolate the replicated DNA fragments by immunoprecipitation. However, any method available in the art for isolating the replicated DNA based on the modified nucleotide incorporated into such replicated DNA may be used.

The following is an example of an embodiment of the present methods where an anti-BrdU antibody is used to isolate the BrdU-labeled replicated DNA fragments. The total mixture of DNA fragments from either population of early or late S-phase cells may be incubated for 20 minutes at room temperature with mouse IgG anti-BrdU antibody (e.g., commercially available anti-BrdU antibody from BD Biosciences) in 1× immunoprecipitation buffer (e.g., 10 mM sodium phosphate, pH 7.0; 0.14 M NaCl; 0.05% Triton X-100), then added to anti-mouse IgG for another 20-minute incubation. According to this method, replicated DNA fragments may be bound by the anti-BrdU antibody and secondary antibody. The replicated DNA may then be precipitated as a DNA-protein complex by centrifugation, washed once with 1× immunoprecipitation buffer, and resuspended in digestion buffer (e.g., 50 mM Tris-HCl, pH 8.0; 10 mM EDTA; 0.5% SDS; 0.25 mg/ml PK) for overnight protein digestion at 37° C. The immunoprecipitated DNA may be collected by ethanol precipitation and resuspended in Tris-EDTA at a concentration of, for example, at least about 250 cell equivalents/μl.

Depending on the type and number of cells as well as the culturing conditions, the amount of replicated DNA isolated from the early and late S-phase fractions of cells may not be enough for genomic array analysis. Therefore, according to some embodiments of the present invention, replicated DNA from both early and late S-phase cells may need to be amplified before introduction to the array. Since replicated DNA is isolated in previous steps, only replicated DNA may be amplified. One consideration is that the relative proportions of DNA fragments not be altered or biased as a result of amplification during this step. Methods for random or whole genome amplification (WGA) of DNA that may be used are known in the art. See, e.g., Hughes et al., "The use of whole genome amplification in the study of human disease," *Progress in Biophys. and Mol. Biol.* 88(1): 173-189 (2005); Lasken et al., "Whole genome amplification: abundant supplies of DNA from precious samples or clinical specimens," *Trends in Biotechnology* 21(12):531-535 (2003); Hawkins et al., "Whole genome amplification—applications and advances," *Current Opinion in Biotechnology* 13(1):65-67 (2002); and Kwoh et al., "Target amplification systems in nucleic acid-based diagnostic approaches," *Am. Biotechnol. Lab.* 8(13):14-25 (1990), the entire contents and disclosures of which are hereby incorporated by reference. For example, samples of replicated DNA may be subjected to whole genome PCR amplification, such as the GenomePlex® whole genome amplification (WGA) method (Sigma).

In addition to PCR-based methods, other examples for amplification of DNA that may be used may include, for example, a transcription-based amplification system (TAS), a self-sustained sequence replication system (3SR), ligation amplification reaction (LAR), ligase-based amplification system (LAS), a Q. beta RNA replication system and run-off transcription, etc. However, PCR is the method generally used for whole genome amplification (WGA) in embodiments of the present methods since it faithfully amplifies the replicated DNA fragments in a uniform and non-biased fashion. One modified PCR procedure that may be used in embodiments of methods of the present invention is ligation-mediated PCR (LM-PCR). See, e.g., O'Geen et al., "Comparison of sample preparation methods for ChIP-chip assays," *Biotechniques* 41(5):577-580 (2006), the entire contents and disclosure of which are hereby incorporated by reference).

According to some embodiments of the present methods, the isolated (and optionally amplified) replicated DNA may be differentially labeled with fluorescent or photoluminescent dyes prior to hybridization to an array. Any fluorescent dye applicable to array technology may be used. For example, the replicated DNA from early and late S-phase cells may be differentially labeled with fluorescently labeled nucleotides. The labeling of the DNA may be performed according to any known or standard method available in the art. According to some embodiments, DNA may be labeled with fluorescently labeled nucleotides using either nick-translation or random priming methods. See, e.g., Lieu et al., "Development of a DNA-Labeling System for Array-based Comparative Genomic Hybridization," *J. Biomol. Tech.* 16(2):104-111 (2005), the entire contents and disclosure of which are hereby incorporated by reference.) Alternatively, the DNA labeling step may be combined with the amplification step above by adding a modified or fluorescent nucleotide into the amplification reaction, which may theoretically bypass the need for a separate labeling step.

Any combination of photoluminescent labels or dyes, such as fluorophores or fluorescent labels/dyes, may potentially be used as long as there is sufficient separation in the wavelength for exciting and/or emitting light between the two or more fluorescent labels to allow separate analysis. Examples of fluorescent labels are known in the art. According to some embodiments, the fluorescent labeling dyes may be Cyanin-3 (Cy3) and Cyanin-5 (Cy5). For example, the fluorescent labeling dyes may be incorporated into the isolated replicated DNA fragments via Cy3- and Cy5-conjugated nucleotide, such as dUTP (Amersham). However, it is to be understood that any other fluorescent labels may be used as long as the fluorescent labels have sufficiently different wavelengths of fluorescence that may be distinguished if simultaneously introduced to the same array. Kits for labeling the DNA with fluorescent dyes, such as Cy3 and Cy5 (e.g., Bioprime Labeling Kit from Invitrogen), and kits for isolating DNA labeled with these dyes (e.g., G50 spin column from Amersham Pharmacia) may also be used.

According to some embodiments of the present methods, early-replicating and late-replicating S-phase DNA may be reciprocally labeled in replicate (i.e., dye swap). In other words, in one test set, early-replicating S-phase DNA may be labeled with a first dye (such as Cy3), and the late-replicating S-phase DNA may be labeled with a second dye (such as Cy5). However, in a reciprocal test, early-replicating S-phase DNA may be labeled with the second dye (such as Cy5), and the late-replicating S-phase DNA may be labeled with the first dye (such as Cy3). By averaging any replication timing differences between the dye swapping data sets, any effects or artifacts caused by variations in labeling reactions for one dye versus the other may be minimized or eliminated.

According to an alternative approach for some embodiments of the present methods, the modified nucleotide may be a fluorescently-labeled nucleotide introduced into the population of cells in culture. Generally, to incorporate the fluorescently-labeled nucleotide into the genome of replicating cells, such cells may also need to be permeabilized according to known methods, such as by electroporation. Following sorting or separation of cells into early and late S-phase fractions, DNA may be isolated and fragmented as described above. Fluorescently-labeled DNA fragments may correspond to regions of the genome replicating during S-phase for each of the early and late S-phase fractions. Therefore, such an approach may provide a short-cut method that may potentially allow direct analysis of replicated DNA on the array without the need for prior isolation or immunoprecipitation of replicated DNA as described above.

According to some embodiments of the present methods, after the replicated DNA has been isolated, amplified (if necessary), and labeled with photoluminescent or fluorescent labels/dyes, the labeled DNA may be hybridized to an array for measurement of replication timing as a function of chromosomal position. The array may be any hybridization array that provides sufficient information (i.e., sufficiently high resolution) regarding replication timing as a function of chromosomal position to identify and/or distinguish a population of cells. Array technology is generally known in the art and may be performed according to relevant manufacturer's instructions.

According to some embodiments of the present methods, the array may be any genomic array querying at least a portion of the genome at a resolution of about 6 kb or greater. For example, the genomic array may be a whole-genome array, such as a comparative genomic hybridization (CGH) array. Regardless of the exact resolution or density of probes on the array, it is advantageous that each of the probes be approximately evenly spaced along the length of each chromosome. Although uneven spacing may potentially be corrected by computer algorithm, evenly spaced array probes allow linear relationships between replication timing and chromosomal position coordinates to be more readily determined. According to some embodiments of the present methods, genomic arrays used in embodiments of the present invention may have a resolution or probe density of about 6 kb or higher (i.e., an average probe spacing of about 6 kb or less). For example, as described herein, CGH arrays having an average probe spacing or resolution of 5.8 kb are able to generate replication timing profiles that may identify the positions, lengths, boundaries, etc. as well as higher density arrays. According to some embodiments, the CGH array may be a Nimblegen array, an Agilent array, an Affymetrix array, etc.

According to other embodiments, the array may be a "tiling" array with a much higher probe density (e.g., a probe every 100 bp). Although a tiling array may have the advantage of generating a high-resolution replication-timing map, it currently requires the use of multiple arrays to query the whole genome of higher organisms. By contrast, however, a CGH array generally provides sufficient resolution of replication timing and has the advantage of allowing a query of the whole genome on a single chip or array. Therefore, a CGH array having a resolution or probe density of about 6 kb or greater (i.e., an average probe spacing of about 6 kb or less) may be advantageous for embodiments of the present methods. However, it is to be understood that, according to some embodiments, the array may query replication timing for only a portion of the genome. For example, depending on the specific assay or application, replication timing profiles over only one or more chromosomes or one or more segments of chromosome(s) may be sufficient to identify and/or distinguish a population of cells. It is also to be understood that multiple arrays may also be used to determine replication timing profiles for a population of cells, even though using a single array may be generally advantageous.

According to some embodiments of the present methods, after binding differentially labeled early-replicating and late-replicating S-phase DNA to the array, the data may be analyzed using an array scanner. Examples of such scanners are known in the art and may include, for example, the GenePix Axon 4000B (Molecular Devices). Alternatively, DNAscope™ IV & V (Biomedical Photometrics) may also be used. However, any scanner having sufficient resolution could be used. As described above, once the amount of replication is quantified for early and late S-phase cells, a replication timing profile may be generated for the population of cells. For example, the replication timing profile may be represented by a ratio that may be calculated and plotted as $\log_2$(early/late) for each chromosomal locus queried. The replication timing data obtained for early and late S-phase cells may be normalized, and the replication timing profile generated from such data may be plotted using a local polynomial smoothing algorithm to generate a loess-smoothed curve.

According to some embodiments of the present methods, once the amount of replication occurring separately in early and late S-phase cells is determined, a replication timing profile may be generated along the length of each chromosome or chromosomal segment tested. A replication timing profile may be generated according to any known and appropriate mathematical and/or statistical method to determine replication timing based on the amounts of DNA replication occurring at each genomic locus in both early and late S-phase cells. Data from individual replicates may be normalized and scaled to have the same median-absolute deviation using the Limma package (R/Bioconductor). Data sets may then be averaged and smoothed (e.g., by local polynomial (loess) smoothing).

Therefore, a replication timing profile for a population of cells may be generated from a series of replication timing ratios or differences for each genomic locus tested along a length of a chromosome. For example, replication timing ratios at genomic loci may be computed on a logarithmic scale, such as $\log_2$(early/late), where "early" and "late" are the amount of signal intensity for a given locus from early S-phase and late S-phase cells, respectively. Such replication timing profile composed of replication timing ratios may be further subjected to loess polynomial smoothing to help eliminate outliers and artifacts. On the logarithmic scale, replication timing ratios having a positive number are earlier replicating, while negative replication timing ratios are later replicating. Of course, these relationships would be reversed if the logarithmic scale is computed as $\log_2$(late/early). As an alternative approach, a replication timing profile may be computed as a difference between early and late S-phase replication along the length of each chromosome. Once a replication timing profile is determined for a population of cells, the data may be used to identify the positions, lengths, boundaries, etc. of replication domains for the population of cells.

G1-phase/S-phase Method for Determining Replication Timing

According to other embodiments of the present methods, the replication timing profile may be determined by a "G1-phase/S-phase" method. Briefly, an asynchronously dividing population of cells may be labeled with a DNA-binding dye and sorted into G1-phase and S-phase fractions. (Two-dimensional FACS may also be used to improve separation of G1-phase and S-phase cell fractions.) DNA from the G1-phase and S-phase fractions may be separately isolated and differentially labeled with fluorescent labels. Finally, the differentially labeled G1- and S-phase DNA samples may be hybridized to a high density genomic array, such as a 6 kb or higher resolution genomic array. Many of the steps, such as DNA isolation, labeling, and array hybridization, may be performed similarly or identically to procedures and embodiments described above for the early/late S-phase method where appropriate. For a further explanation and description of the G1/S-phase method to determine the replication timing profile for a population of cells which may be used in some embodiments of the present methods, see, e.g., Woodfine et al., "Replication timing of the human genome," *Hum. Mol. Genet.* 13:191-202 (2004); and Woodfine et al., "Replication Timing of Human Chromosome 6," *Cell Cycle* 4:172-176 (2005), the entire contents and disclosures of which are hereby incorporated by reference. Again, embodiments of the present methods using the G1/S-phase method may be performed in replicate and may implement dye-swap experiments to control for labeling effects and conditions. In addition, raw data obtained from the genomic array may be normalized, and replication timing profiles may be subjected to local polynomial (loess) smoothing according to embodiments of the present methods.

The proportion of cells in the unsynchronized S-phase fraction which have replicated a particular sequence of the genome will be proportional to the time at which such sequence replicates in S-phase. Therefore, the ratio of S:G1 phase signal intensity reported for each sequence from the array represents the average sequence copy number in the unsynchronized S-phase fraction with the G1-phase fraction providing a baseline. Thus, sequences with ratios closer to about 2:1 represent loci that replicate earlier during S-phase, while conversely sequences with ratios closer to about 1:1 represent sequences which replicate later during S-phase.

Synchronization Method for Determining Replication Timing

According to other embodiments of the present methods, the replication timing profile may be determined by a "synchronization" method. Any method known in the art for producing a synchronous population of cells in culture may be used. For example, such methods may rely on the use of any compound known to achieve reversible arrest at a defined point in the cell cycle, such as by using nocodazole, aphidicolin, hydroxyurea, double-thymidine block, etc., followed by release of cells in unison or by removing a compound required for proliferation, such as by starvation, followed by re-addition. Other possibilities may include, for example, elutriation by cell size or mitotic shake-off as known in the art. In cases where the cells have become successfully arrested at a particular cell cycle stage, the cells may be released from the arrest either by removal or addition of a compound to produce a population of synchronously dividing cells. Depending on the starting point in the cell cycle for the newly generated synchronous population of cells as well as the type of cells in question, the cell cycle stage of the synchronous population of cells may be known over time based on the amount of time that has expired since their generation, selection, or release.

Therefore, a population of cells may be separated into different cultures or sub-populations and synchronized according to some embodiments of the present methods. Each identical sub-population of separately synchronized cells may then be exposed to a modified nucleotide at different times corresponding to different portions of the cell cycle. For example, one of the identical sub-population of cells may be exposed to (or pulse-labeled with) BrdU at a time corresponding to early S-phase, while the other identical sub-population of cells may be pulse-labeled with BrdU at a different time corresponding to late S-phase. These cells may then be separately harvested, their DNA isolated and fragmented, and replicated DNA purified from each sub-population of cells on the basis of the modified nucleotide, such as by immunoprecipitation with an anti-BrdU antibody. Once the samples of replicated DNA from early and late S-phase cells have been purified, they may be differentially labeled with a photoluminescent (e.g., fluorescent) label or dye and subjected to analysis by hybridization to a genomic array to generate a replication timing profile similarly to what is described above.

DNA isolation, purification, labeling, and array hybridization steps may be performed similarly or identically to procedures and embodiments described above for the early/late S-phase method where appropriate. For a further explanation and description of the synchronization method to determine the replication timing profile for a population of cells which may be used in some embodiments of the present methods, see, e.g., MacAlpine et al., "Coordination of replication and transcription along a *Drosophila* chromosome." *Genes Dev.* 18:3094-3105 (2004), the entire contents and disclosure of which are hereby incorporated by reference. According to some embodiments, the replication timing profile for a population of cells may be determined according to methods similar to the early/late S-phase method. For example, replication timing ratios may be determined as a ratio of early S-phase to late S-phase replication at a given genomic locus, such as $\log_2$(early/late), with a positive value indicating earlier S-phase replication and negative value indicating later S-phase replication timing.

According to alternative embodiments, a single population of synchronized cells may be labeled with one modified nucleotide during early S-phase and a different modified nucleotide during late S-phase. Subsequently, early and late S-phase replicating DNA may be separated by immunoprecipitation with different antibodies to take advantage of the different modified nucleotides, and the different samples of early and late replicating DNA differentially labeled with fluorescent labels and hybridized to a genomic array.

Sequencing Methods for Determining Replication Timing

According to other embodiments of the present methods, the replication timing profile may be determined by using a sequencing method. For example, instead of scanning and quantifying fluorescently labeled DNA by hybridizing to an array, total or replicated DNA (e.g., corresponding to S-phase vs. G1-phase DNA or early S-phase vs. late S-phase DNA, respectively, as described above) may be sequenced to determine its identity and location in a genome by comparison to known genomic sequences of an organism. The amount of replication occurring for any given region may be quantified by the number of sequence reads for such a region. In other words, the more abundantly a particular region of a genome is represented in a sample, the greater the number of sequences corresponding to such regions of the genome will be generated. Therefore, the sequencing step may be used to quantify the amount of replication occurring in a fraction of cells used to make the sample. Such quantities may then be used to create a replication timing profile for a population of cells similarly to above.

Alternatively, according to some embodiments, what is referred to hereafter as a "sequence capture" method may be used. According to this approach, total or replicated DNA samples (e.g., corresponding to S-phase vs. G1-phase DNA or early S-phase vs. late S-phase DNA, respectively, isolated from a population of cells as described above) may be subjected to an additional step to further isolate only those fragments or sequences corresponding to particular segments or regions of interest within a genome. For example, total or replicated DNA from a fraction of cells may be immobilized on a capture array (or column) containing sequences corresponding to the particular segments or regions of interest within the genome and subsequently eluted after separation from the rest of the unbound DNA in the sample. Such segments or portions of interest may correspond, for example, to replication timing fingerprint(s) or informative segments of replication timing fingerprint(s) for the genome of a particular type of cells. Once these DNA fragments or sequences of interest have been isolated from the sample, they may be subjected to sequencing to identify their location in the genome and quantified as described above. Again, such quantities may then be used to create a replication timing profile for the population of cells, as described above.

Embodiments of present methods may use any sequencing method known in the art. Generally speaking, any potential sequencing bias in carrying out sequencing reactions may be avoided, and sequencing may be performed at random to achieve sequencing of most or every DNA molecule present in a sample. For example, randomized primers may be used, or a sequence corresponding to one or more primer sequence(s) may be ligated to each DNA molecule. In addition, the degree of resolution for the replication timing profile is generally proportional to how "deep" the sequencing reactions are performed. In general, the more overlapping sequence information obtained from a DNA sample derived from a population of cells, the higher the resolution will be for determining the quantity of DNA (and hence DNA replication) present in the sample over smaller segments, portions, regions, etc. of chromosome(s) of a genome of the population of cells. The number and extent of sequencing reactions would need to be sufficiently "deep" to allow for resolution capable of accurately and reliably determining the positions, lengths, boundaries, etc. of replication timing domains from such replication timing profile. A number of improved "deep sequencing" methods have recently emerged for generating large amounts of DNA sequence information in less time making the sequencing approach for generating a replication timing profile an increasingly feasible option.

Step 2: Identifying and/or Distinguishing the Population of Cells on the Basis of their Replication Timing Profile During a second step for embodiments of the present methods, the identity of a population of cells, as well as its species of origin, may be determined on the basis of its replication timing test profile by comparison to another replication timing reference profile that may be simultaneously or previously determined. Alternatively, a replication timing profile for a population of cells may be used to distinguish the population of cells from others, such as from other types of cells and/or possibly from cells from different species. According to some embodiments, the replication timing profile may be compared to a known replication timing profile or set of known replication timing profiles, which may also be a part of a database of known replication timing profiles, to thereby identify such population of cells and/or distinguish such population of cells from others. Alternatively, the replication timing profile may be compared to another replication timing profile that may be simultaneously or previously determined. According to embodiments of the present methods, a population of cells may be identified and/or distinguished from all other types of cells or only from a group of candidate cell types or cells of interest.

According to some embodiments of the present methods, once a replication timing profile has been determined for a population of cells based on any of the methods described in the first step, the positions, lengths, boundaries, and/or other characteristics of replication timing domains may be determined. Where replication timing is plotted on a y-axis versus chromosomal coordinates along an x-axis, replication domains may be identified as regions of fairly uniform y-axis values separated by sharp transitions. On the basis of a replication timing profile for a population of cells, for example, replication domains and their properties (e.g., chromosomal position, length, boundaries, etc.) may be identified and characterized according to a segmentation algorithm operating with the assistance of a computer, such as DNAcopy (R/Bioconductor) based on analysis of DNA copy number data. This computerized program may provide a circular binary segmentation method for the analysis of array-based DNA copy number data (see, e.g., Olshen et al., "Circular binary segmentation for the analysis of array-based DNA copy number data," *Biostatistics* 5(4):557-72 (2004), the entire contents and disclosure of which are hereby incorporated by reference). For identification of replication timing domains, such segmentation algorithms or programs may potentially be applied directly to raw data sets or mean replication timing ratios without any smoothing. However, according to some embodiments, a replication timing profile for a population of cells or an average profile for a group of related cells or replicates will be subjected to normalization and polynomial (loess) smoothing to improve results and remove outliers prior to analysis or comparison. Once chromosomal regions corresponding to individual early or late replication timing domains have been determined, characteristics of such domains may be easily deduced by directly measuring the positions, lengths, strengths, and boundaries of each domain.

As stated above, once a replication timing profile is determined for a population of cells, such population of cells may be identified and/or distinguished in relation to other replication timing profiles. According to some embodiments of the present methods, such an analysis may be performed qualitatively by eye to determine whether or not there is a match between two or more replication timing profiles, for example, where only an anecdotal determination is sought or where there are obvious differences in replication timing such that statistical analysis is not necessary. According to other embodiments, however, identifying and/or distinguishing a population of cells may only be performed accurately and reliably by statistical analysis, such as with the aid of a computer and associated software.

Such computer software may operate on the basis of an algorithm and/or software program that interprets, compares, etc., replication timing profiles originating from different sources (e.g., by comparing the relative positions, lengths, and boundaries of early and/or late replication timing domains). According to some embodiments, the same computer and/or software may perform all aspects of reading and interpreting the data. For example, the computer and associated software may read the data from the scanner, compute the replication timing profile(s) and/or positions, lengths, boundaries, etc., of early and late replication domains, and statistically compare or determine whether a replication timing profile of a population of cells is the same or different from other replication timing profiles, replication timing fingerprints, and/or informative segments of replication timing fingerprints, each of which may be contained in a database. Such computer and associated software may further output such results or determinations on a screen or in hard copy to a user and express such results or determinations either qualitatively, categorically, or in terms of various probabilities or confidence levels, such as by providing numerical values of similarities and/or differences between two or more replication timing profiles compared, such as a percent match or a probability match.

To identify and/or distinguish a population of cells from others according to embodiments of the present invention, any acceptable mathematical or statistical technique may be used. Generally speaking, a replication timing test profile generated according to the first step of an embodiment of the present methods may be compared to a separately derived replication timing profile or an average profile for two or more separately derived replication timing profiles, which may be simultaneously or previously determined and/or may be part of a database of replication timing profiles or average profiles. Such a comparison may be made on either the probe or domain level. For example, the degree of correlation (or lack thereof) between a test profile for a population of cells and other replication timing profiles or average profiles for a distinct group of cell populations may be calculated in terms of a correlation coefficient (R) or coefficient of determination ($R^2$). The correlation coefficient (R) corresponds to the degree of proportionality between the two data sets (e.g., R=1 means there is perfect positive correlation, whereas R=−1 means there is a perfectly inverse correlation). According to other embodiments of the present methods, replication timing data may be compared on the basis of the characteristics of replication timing domains by noting differences in the positions, lengths, boundaries, etc., of replication domains and determining if there is a significant difference.

According to some embodiments, a replication timing profile for a population of cells may be considered a "match" to another replication timing profile or average profile if the degree of correlation is above a predetermined threshold or level. Replication timing profiles that do not reach such correlation threshold may be considered indeterminate or not a match. For example, such a correlation coefficient may be calculated based on a comparison of replication timing ratios along the length of each chromosome and expressed as an average correlation of all such comparisons. According to some embodiments of the present methods, a correlation coefficient (R) of about 0.85 or greater may indicate a match; alternatively, a correlation coefficient (R) of about 0.9 or greater may indicate a match. According to other embodiments of the present methods, a correlation coefficient (R) of less than about 0.8 may indicate that there is not a match.

According to an alternative approach of the present methods, the comparison may be made between all loess-smoothed values, such as a logarithmic replication timing ratio, for each probe on the length of each chromosome. Between replicates of the same population of cells or experiments using different cells of the same type, at least about 95% (e.g., 95-99%) of loess-smoothed replication timing ratios would be expected to differ by less than about 0.5 along the length of each chromosome. In other words, a population of cells may be identified as being the same cell type as the another population of cells (i.e., a match) if: (1) their respective profiles or average profiles have at least about 95% (e.g., 95-99%) of loess-smoothed replication timing ratio values differing by less than about 0.5; or (2) only about 5% or less (e.g., 1-5%) of loess-smoothed replication timing ratio values differ by more than about 0.5. On the other hand, it is expected that a population of cells may be distinguished from another population of cells or cell type (i.e., not a match) if greater than about 10% of their respective loess-smoothed replication timing ratio values differ by about 0.5 or greater, such as from about 10% to about 20% of their respective loess-smoothed replication timing ratio values differ by about 0.5 or greater. However, to distinguish closely related cell types (e.g., slightly different differentiating states), it may be necessary that a population of cells be distinguished from another closely related population of cells or cell type (i.e., not a match) by using a standard where greater than about 7% of their respective loess-smoothed replication timing ratio values differ by about 0.5 or greater.

According to some embodiments of the present methods, instead of comparing an assorted, diverse, unrelated, etc., collection of replication timing profiles from individual replicate experiments from individual populations of cells, a replication timing test profile for a population of cells may be compared to an average of replication timing profiles for a group of related cells or a group of distinct populations of cells of the same type, which may be simultaneously or previously determined and/or a part of a database. In other words, such average replication timing profile may be determined from multiple replication timing experiments for either a single population of cells or for a collection of different populations of cells of the same type. For example, an average replication timing profile may be generated from replicate experiments using the same cell line or homogeneous population of cells, or alternatively, an average replication timing profile may be generated from multiple replication timing experiments in different cells or cell lines of the same type, such as, for example, different cell lines derived from the same tissue or cell type of a particular organism. Each replication timing profile from each replicate or experiment may preferably be normalized and/or subjected to loess polynomial smoothing to improve the data prior to averaging.

The advantage of comparing a replication timing test profile for a population of cells to two or more replication timing profiles or an average replication timing profile is that it allows a more accurate and reliable assignment of a replication timing profile to a particular cell type. Since average replication timing profiles may be derived from a plurality of experiments or replicates, the mean values may be expressed at various confidence levels in terms of their standard deviation. Therefore, differences in replication timing ratios between the replication timing test profile and the average replication timing reference profile for a particular cell type over particular regions of chromosomes may be analyzed to determine if those differences are within various degrees of standard deviation that may be used to indicate a match. Conversely, if the replication timing test profile over particular regions of chromosomes falls outside of one or more standard deviations for the average profile, then the population of cells may not be considered a match, and may represent a different cell type than represented by the average profile. For example, if such differences are within one, two, or three standard deviations across the entire genome, then the population of cells may be considered a match, whereas if such differences fall outside one, two, or three standard deviations for a significant portion or length of the genome, then the population of cells may be considered not a match.

According to some embodiments, the replication timing test profile for a population of cells may be compared to another replication timing profile for a distinct population of cells or an average replication timing profile from a group of related populations of cells by subtracting the other replication timing profile or average profile from the test profile to produce a replication timing differential plotted along the length of each chromosome. If the replication timing profiles for a given chromosomal location are the same, the difference would be expected to be approximately zero. However, if there are significant differences in replication timing between the two profiles for a given chromosomal position or region, then a positive or negative number that deviates from zero may be expected. Since early and late replication timing domains are separated by sharp transitions, if domain boundaries do not align between the test profile and another replication profile or average profile used for comparison, then a significantly positive or negative differential may be expected over such regions.

A segmentation algorithm, such as a DNAcopy (R/Bioconductor) program, may be used to identify regions having significantly non-zero replication timing differentials. By determining the number, length, and extent of such non-zero replication timing differential regions along each of the chromosomes, a determination may be made whether or not the test profile is a match to another replication timing profile or average profile. Differentials having strongly positive or negative values over a significant length or portion of the genome in one or more locations may indicate that there is not a match between the profiles being compared, and thus the two respective cell types are not the same. By contrast, cells of the same type may be expected to display very few, if any, differences (i.e., significantly positive or negative differential values) over any appreciable length(s) of the genome. In general, the longer the chromosomal length over which there is a significantly positive or negative differential value, the less that differential value needs to be to indicate that there is not a match.

According to some embodiments of the present methods, a replication timing profile may be compared instead to a "replication timing fingerprint." A replication timing fingerprint for a particular cell type may be determined from either several replicates of the same population of cells or from separate experiments conducted on a group of related populations of cells of the same type (i.e., having the same differentiation state and derived from the same organism (and tissue type if differentiated)). By comparing the different replicates or experiments for cells of the same type, a combined replication timing profile that accurately conforms to each of the replication timing profiles from each of the replicates or experiments may be generated. Regions that show little variation between replicates and/or experiments may be assigned a mean value and a high degree of confidence, whereas regions that show variation may be assigned lower confidence and may be excluded from further fingerprint analysis.

Subsequently, by comparing such a combined replication timing profile to replication timing profiles of different cell types, consistent differences in replication timing may be observed. For example, a series of replication timing differential values between replication timing ratios from one cell type and those from another cell type may be plotted over the length of each chromosome (similarly to above). Regions of chromosomes that are routinely different (i.e., have consistent differential values) for a particular type of cell compared to all other cell types tested or known may be used to help define a replication timing fingerprint for that cell type and may be referred to as an "informative segment" of the genome for purposes of the replication timing fingerprint, whereas regions that do not differ in replication timing or that lack consistency among cells of the same type may be considered "uninformative segments." The collection of all such informative segments for cells of a particular cell type may be used to define the "replication timing fingerprint" for such cell type, which may be used as a basis for comparison. In general, these "fingerprints" for a particular cell type will include only those informative segments of high confidence that show very significant differentials in replication timing over a substantial length of a chromosome when compared to all other cell types. However, a replication timing fingerprint for a particular cell type may further include one or more informative segment(s) having replication timing profiles that may be shared among two or more cell types if a population of cells of the particular cell type having such informative segment(s) is only being compared to other candidate cell types that do not have the same replication timing profile over such informative segment(s) of the genome. As an example of the present methods used to determine a replication timing fingerprint, the nearest neighbor statistical approach may be used to group and classify replication timing profiles for distinct populations of cells and cell types in relation to one another.

According to some embodiments of the present methods, a replication timing profile over a segment of a genome may be defined as the collection of all informative segments of the genome for a population of cells, with any given region or segment of a genome defined as an informative segment for a particular cell type if two conditions are met: (1) the region covers at least about 50 kilobases (kb) of genomic DNA; and (2) the region has at least about a 0.5 replication timing ratio differential across such length compared to all other cell types, or at least all other relevant cell types compared. The requirement for at least about a 50 kilobases (kb) region is derived from the fact that such distance corresponds to about 9 or more consecutive probes (assuming about 5.8 kb resolution) and the smallest known replicon (i.e., the smallest unit of differential that would be expected biologically). By including at least about 9 probes, the vast majority of differences due to probe-level noise will be excluded. The requirement of at least about 0.5 replication timing differential provides a practical cutoff and is fairly close to two standard deviations of separation that would define the top 5% of differences as being eligible for the replication timing fingerprint.

By using replication timing fingerprints (i.e., unique regions of differential replication timing for a particular cell type) for one or more populations of cells, comparison to other replication timing profiles may be facilitated because the analysis may be focused on only those informative segments that comprise the replication timing fingerprint. Therefore, according to present embodiments, a replication test profile for a population of cells may be compared to replication timing fingerprints for a variety of cell types, which may be contained in a database, to identify the population of cells and/or distinguish the population of cells from others. Therefore, a population of cells displaying a replication timing profile having most or all of the characteristics of a replication timing fingerprint for a particular cell type may be identified as being such cell type. Conversely, a population of cells displaying a replication timing profile lacking the characteristics of a replication timing fingerprint of a particular cell type may be distinguished from such cell type.

According to some embodiments of the present methods, a population of cells displaying a replication timing profile that is similar or substantially the same as most or all of the informative segments of a replication timing fingerprint for a particular cell type may be identified as being the same cell type. By contrast, according to other embodiments, a population of cells displaying a replication timing profile that is substantially different than one or more of the informative segments of a replication timing fingerprint for a particular cell type may be distinguished from such cell type.

For example, according to some embodiments, a population of cells may be identified as being a particular cell type if the replication timing profile has replication timing ratio differentials of about 1.0 or less across the length of most or all informative segments of a replication timing fingerprint for the particular cell type. Alternatively, for example, a population of cells may be identified as being a particular cell type if the replication timing profile has replication timing differentials of about 2.0 or less across the length of most or all informative segments of a replication timing fingerprint for the particular cell type. However, a population of cells may be identified as being a particular cell type even if the replication timing profile has replication timing differentials of greater than about 2.0 across the length of one or more informative segments of a replication timing fingerprint for the particular cell type as long as the number and/or length of such segments is sufficiently small.

Conversely, according to other embodiments, for example, a population of cells may be distinguished from a particular cell type if the replication timing profile has replication timing ratio differentials of about 4.0 or greater across the length of one or more informative segments of the replication timing fingerprint for the particular cell type. However, a population of cells may be distinguished from a particular cell type even if the replication timing profile has replication timing ratio differentials of less than about 4.0 across the length of one or more informative segments of the replication timing fingerprint for the particular cell type as long as the number and/or length of such segments is sufficiently small.

The ability to use replication timing profiles to identify and/or distinguish cells may provide enormous utility in a variety of contexts. For example, a replication timing profile for a population of cells determined by some embodiments of the present methods may be used to determine whether the population of cells is pure or homogeneous depending on how perfectly the replication timing profile for such population of cells conforms to its known or expected replication timing profile or fingerprint. For example, reductions in the relative prominence of certain features or fingerprints of a replication timing profile of a population of cells that are expected for a particular cell type, which may be expressed as a reduced probability or percent match, may be used to indicate less than full purity or homogeneity.

According to some embodiments of the present methods, the replication timing profile for a population of cells may also be used to determine whether a population of cells is normal or diseased. For example, some embodiments of the present methods may be used as a means for diagnosing whether an individual has an inherited disease or whether an individual has cancerous cells in their body. Embodiments of the present methods may be used to determine whether a cell or population of cells has become transformed (i.e., whether or not cells are cancerous or tumorigenic). For example, transformed cells generally have altered gene expression and often suffer from genetic instability. Therefore, transformed cells may experience changes in their replication timing profiles due to changes in chromatin structure and/or expression of genes, thus allowing some embodiments of the present methods to identify and/or distinguish such population of cells and determine whether they are diseased, transformed, etc. Cells that have become transformed, cancerous, or tumor cells, therefore, may have different replication timing profiles compared to normal cells of the same tissue type or from which they originated.

Embodiments of the present methods may also be used to diagnose whether a population of cells suffer from other types of disease, such as a developmental or inherited disease. Furthermore, embodiments of the present methods may potentially be used to distinguish subtly different but related types of disease. Being able to characterize a population of cells molecularly may have the advantage of allowing a person, such as a physician or veterinarian, to diagnose disease and tailor treatments for an individual. For example, a biopsy or sample containing a population of cells in question may be extracted or removed from an individual, cultured, and their replication timing profiles determined. The replication timing profile for the cells in question may then be used for comparison to other replication timing profiles and/or fingerprints corresponding to normal and/or diseased cells to determine whether the cells in question are normal or diseased.

Embodiments of the present methods may be used to determine the stage of development of a cell or population of cells. Some embodiments of the present methods may be used to determine an extent of differentiation of a population of cells into a particular cell type and whether such differentiation is proceeding normally. For example, embodiments of the present methods may be used to determine whether a population of cells are stem cells, other precursor cells, partially or fully differentiated cells, etc. Alternatively, embodiments of the present methods may be used to determine whether a cell or population of cells has been successfully de-differentiated into a precursor or stem cell, such as, for example, whether an induced pluripotent stem (iPS) cell has become fully reverted.

Such applications may arise in the context of tissue engineering where cells are being designed for use in an individual. Before administering engineered cells to an individual, it may be necessary for purposes of safety and effectiveness that the population of cells are what they are purported to be. Therefore, embodiments of the present methods may be used to determine the homogeneity and identity of cells that may be used for therapy. Recent advances in de-differentiating somatic cells to a pluripotent state have opened up possibilities for using an individual's own cells to create a variety of cell types that may be used for treatment of the same individual without the complications of non-self immune reactions or rejection. Therefore, embodiments of the present methods may be used to investigate the chromatin state of cells as evidenced by their replication timing profile to determine whether a population of cells has in fact assumed their purported identity prior to their use in treatment. For example, where stem cells are being differentiated into precursors or specific cell types, embodiments of the present methods may be performed to ensure that cells are differentiating properly and acquiring the desired state of differentiation prior to their use in therapy or treatment.

General Methods

General molecular biological techniques, biochemical techniques, and microorganism techniques which may be used in embodiments of the present invention are described in, for example, Innis, M. A. et al., "PCR Strategies," Academic Press (1995); Ausubel, F. M., "Short Protocols in Molecular Biology: A Compendium of Methods from Current Protocols in Molecular Biology," (Wiley & Sons, 5$^{th}$ Ed., 2002); Sninsky, J. J. et al., "PCR Applications: Protocols for Functional Genomics," (Academic Press, 1999); Sambrook J. et al., "Molecular Cloning: A Laboratory Manual," (3$^{rd}$ Ed., Cold Spring Harbor Laboratory Press, Cold Spring Harbor, N.Y., 2001); Freshney, R. I., "Culture of Animal Cells: A Manual of Basic Techniques," (4$^{th}$ Ed., 2000); Spector, D. L., Cells: "A Laboratory Manual, Culture and Biochemical Analysis of Cells," (Cold Spring Harbor Press, 1998), the entire contents and disclosures of which are hereby incorporated by reference. Gene introduction may be confirmed by any standard method known in the art, such as those described herein, including, e.g., Northern blotting analysis and Western blotting analysis, or other known or common techniques. Any technique may be used herein for introduction of a nucleic acid molecule into cells, including, for example, transformation, transduction, transfection, etc. Such nucleic acid molecule introduction techniques are known in the art and commonly used.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

The following non-limiting examples are provided to further illustrate embodiments of the present invention. It should be appreciated by those of skill in the art that the techniques disclosed in the examples that follow represent approaches that have found function in the practice of these embodiments, and thus can be considered to constitute examples of modes for its practice. However, those skilled in the art, in light of the present disclosure, should appreciate that many changes can be made in the specific embodiments that are disclosed herein and still obtain the same or similar result without departing from the spirit and scope of the present invention. The following section provides examples for determining replication timing profiles based on the early/late method described above. However, this should not be construed as a limitation since it should be understood that the present invention may rely on other methods described herein for determining replication timing profiles for a population of cells.

Example 1

Materials and Methods

ESC Culture, Neural Differentiation, and BrdU-labeling

D3 cells (see, e.g., Doetschman et al., "The in vitro development of blastocyst-derived embryonic stem cell lines: formation of visceral yolk sac, blood islands and myocardium," J. Embryol. Exp. Morphol. 87:27-45 (1985), the entire contents and disclosure of which are hereby incorporated by reference), 46C cells (see, e.g., Ying et al., "Conversion of embryonic stem cells into neuroectodermal precursors in adherent monoculture," Nat. Biotechnol. 21:183-186 (2003), the entire contents and disclosure of which are hereby incorporated by reference), and TT2 cells (see, e.g., Yagi et al., "A novel ES cell line, TT2, with high germline-differentiating potency," Anal. Biochem. 214:70-76 (1993), the entire contents and disclosure of which are hereby incorporated by reference) are male ESC lines with a normal karyotype that are cultured in the presence of LIF (leukemia inhibitory factor) as described in, for example—Rathjen et al., "Lineage specific differentiation of mouse ES cells: formation and differentiation of early primitive ectoderm-like (EPL) cells," Methods Enzymol. 365:3-25 (2003), the entire contents and disclosure of which are hereby incorporated by reference. D3 ESCs are differentiated as embryoid bodies in a conditioned medium as described in, for example, Rathjen (2003), supra) and NPC samples are collected after 9 days of differentiation. The 46C and TT2 ESCs are differentiated in adherent monolayer culture as described (see, e.g., Ying et al. (2003), supra) and NPC samples are collected after 6 days (46C) or 8 days (TT2) of differentiation. For BrdU-labeling, cells are incubated in the presence of 50 μM BrdU for 1 or 2 hr, washed twice with ice-cold PBS, trypsinized and fixed in 75% ethanol as described in, for example, Hiratani et al., "Differentiation-induced replication-timing changes are restricted to AT-rich/long interspersed nuclear element (LINE)-rich isochores." PNAS 101:16861-16866 (2004), the entire contents and disclosure of which are hereby incorporated by reference).

Cell Cycle Fractionation and Isolation of BrdU-labeled DNA

BrdU-labeled, fixed cells are resuspended in PBS containing 1% FBS (2-3×106 cells/ml), stained with propidium iodide (50 μg/ml) for 30 min in the presence of RNaseA (0.5 mg/ml), and then sorted into two cell cycle fractions (early and late S) by flow cytometry, as described in, for example, Hiratani et al., (2004), supra). Isolation of BrdU-labeled DNA has been described in, for example, Hiratani et al., (2004), supra).

Replication Timing Analysis by Microarrays

To obtain sufficient target DNA for microarray hybridization, immunoprecipitated DNA samples are amplified by whole genome amplification (WGA) (Sigma, GenomePlex®) as described in, for example, O'Geen et al., "Comparison of sample preparation methods for ChIP-chip assays." *Biotechniques* 41:577-580 (2006), the entire contents and disclosure of which are hereby incorporated by reference). The maintenance of relative enrichment of several known early and late replicating genes before and after WGA is confirmed. Sample labeling, hybridization and data extraction are performed according to standard procedures by NimbleGen Systems using a 5.8 kb resolution mouse whole-genome microarray (Nimblegen Systems, 2006-07-26_MM8_WG_CGH). For all except 46C NPCs, two independent biological replicates are analyzed, for which early- and late-replicating DNA were labeled reciprocally with Cy3 and Cy5 (=dye switch). For comparison of different probe density, a 100 bp resolution microarray covering portions of mouse chromosome 6 and 7 (Nimblegen Systems, 2006-07-17_MM8_Tiling_Set15) is hybridized with D3 ESC samples in duplicate.

Quality control PCR experiments are performed to validate microarray experiments. Pairs of immunoprecipitated BrdU DNA samples from early and late S fractions are subject to PCR and mean % early S-phase values [=(intensity of early fraction)/(intensity of early and late fractions combined)] from 6-7 pairs of DNA samples are calculated, as previously described [22]. Genes above and below 50% are classified as early (E) and late replicating (L), respectively. From microarray data, replication timing ratios of genes are obtained from the loess-smoothed curve at the transcription start sites. Replication timing ratios above and below 0 are classified as early (E) and late replicating (L), respectively.

Microarray Data Normalization and Replication Timing Ratio Calculation

Normalization procedures are carried out using R/Bioconductor (http://www.r-project.org), while various data analyses are carried out using either R/Bioconductor, Excel (Microsoft), or Spotfire DecisionSite (Spotfire, Inc). For each experiment, raw data sets are loess-normalized to remove signal intensity-dependent bias and scaled to have the same median-absolute deviation using a limma package (R/Bioconductor). From two replicates, the mean replication timing ratios for each probe are calculated. Mean ratios are used to generate a smoothed profile using local polynomial smoothing (loess) for each chromosome [span=300000/(chromosome size)]. Replication timing ratios of 18,679 RefSeq genes are obtained as follows. Briefly, redundancy is removed from a list of 20,509 RefSeq genes (mm8 assembly refflat.txt file from UCSC Genome Browser; http://genome.ucsc.edu) to generate a list of 18,702 non-redundant RefSeq genes on non-chrN_random chromosomes. Loess-smoothed replication timing ratios of these genes at their transcription start sites are obtained using an R/Bioconductor script. Twenty three genes that resided within large gaps in probes (>0.65 kb) are excluded to generate the final list of 18,679 RefSeq genes with replication timing ratios matched. Complete replication timing data sets for all (384,849) probes may be found at http://www.replicationdomain.org.

Transcription Analysis by Microarrays

Total cellular RNA is isolated from D3 ESCs or NPCs (three biological replicates per cell state) and steady-state transcript levels are determined by Affymetrix GeneChip® microarrays (Mouse Genome 430 2.0), which are highly reproducible ($R^2 > 0.98$ between all replicates). After quality control tests (see, e.g., Bolstad B M, "Quality Assessment of Affymetrix GeneChip Data," in: Gentleman et al., *Bioinformatics and Computational Biology Solutions using R and Bioconductor* (New York, N.Y., Springer, 2005, pp. 33-48), the entire contents and disclosure of which are hereby incorporated by reference), data sets are subjected to normalization by the Probe Logarithmic Intensity Error algorithm (PLIER) developed by Affymetrix for calculating probe signals. For each Affymetrix "probe set," signal intensity of the three biological replicates are averaged (=average intensity). Genes may be represented by multiple probe sets. In such cases, the one with the highest total intensity (i.e., sum of ESC and NPC average intensity) is defined as the representative probe set and the other probe sets are not used. The highest intensity probe sets are used because these sets are empirically the most consistent with reverse transcriptase (RT)-PCR analysis and may be defined in an objective way. Present (transcriptionally active) and absent (inactive) calls are generated by MAS5.0 (Affymetrix) per replicate per probe set, which results in multiple present-absent calls for a given gene [=3×(total number of probe sets for a gene)]. "Present" genes are defined as those with more than 50% of all probe set calls being "present.'" The 15,143 (81%) of the 18,679 RefSeq genes, for which replication timing ratios are obtained, are represented on the Affymetrix GeneChip® microarrays and are assigned transcription levels and present-absent calls. Validation of transcription array results is evident from previously published transcription analysis under the same condition (see, e.g., Rathjen et al., "Directed differentiation of pluripotent cells to neural lineages: homogeneous formation and differentiation of a neurectoderm population." *Development* 129:2649-2661 (2002), the entire contents and disclosure of which are hereby incorporated by reference).

Identification of Replication Domains and Domains that Change Replication Timing DNAcopy (R/Bioconductor) is a segmentation algorithm for the analysis of microarray-based DNA copy number data (see, e.g., Venkatraman et al., "A faster circular binary segmentation algorithm for the analysis of array CGH data." *Bioinformatics* 23:657-663 (2007), the entire contents and disclosure of which are hereby incorporated by reference). For identification of replication domains, this method is applied directly to data sets containing mean replication timing ratios for all probes before loess-smoothing. The parameters, nperm (number of permutation) and alpha (the significance level for the test to accept change-points), are set at 10,000 and $1 \times 10^{-15}$, respectively, which are empirically determined based on how well the resultant segmentation profile traced the loess-smoothed profile. Once determined, these parameters are fixed and used for objective segmentation of all data sets. A segmentation is run for each chromosome. The same strategy is used to identify chromosomal domains that change replication timing, except in this case, data sets consisting of replication timing ratio differential (=NPC ratio−ESC ratio) for all probes are used for segmentation. Among the resultant 2,042 segments, 102 EtoL, 102 LtoE, 232 EtoE, and 96 LtoL domains are selected based on the criteria described herein.

Analysis of Transitions Between Replication Domains

Three chromosomes are analyzed for transitions between domains, identifying 25 from each of the following regions: chr2:40,000,000-75,000,000; chr11:40,000,000-68,000,000; and chr16:40,000,000-65,000,000. Transition regions are defined as regions with large and uni-directional changes in replication timing along the chromosomes on the loess-smoothed curve. The positions at which this uni-directionality stops are defined as the two "ledges" of a transition region.

GC and LINE-1 Content Calculation

GC and LINE-1 content is calculated based on the UCSC Genome Browser database (gc5base.txt and chrN_rmsk.txt, mm8 assembly; http://genome.ucsc.edu) using the Table Browser function of the UCSC Genome Browser as well as an R/Bioconductor script.

DNA-FISH

DNA-FISH is performed essentially as described in, for example, Li et al., "The replication timing program of the Chinese hamster beta-globin locus is established coincident with its repositioning near peripheral heterochromatin in early G1 phase," *J. Cell Biol.* 154:283-292 (2001), the entire contents and disclosure of which are hereby incorporated by reference, with some modifications. Briefly, preparation and fixation of cells are done as described in, for example, Solovei et al., "FISH on three-dimensionally preserved nuclei," in: Beatty, B. et al., Editors, *FISH: Practical Approach*, (Oxford: Oxford Univ. Press. 2002), the entire contents and disclosure of which are hereby incorporated by reference) to preserve 3D structure. BAC probes are used for all genes tested, with some genes additionally tested by PCR probes of 8.9-10.2 kb. DIG-labeled probes are generated using the DIG-nick translation mix (Roche, Cat#11745816910). Primary and secondary antibodies used to detect the DIG-labeled probes are sheep anti-DIG-fluorescein (Roche Applied Science, Cat#11207741910) and rabbit fluorescein anti-sheep IgG (Vector, Cat#FI-6000), respectively. Images are captured with a DeltaVision Image Restoration Microscope System (Applied Precision) attached to an Olympus IX-71 fluorescence microscope equipped with an Olympus PlanApo 100×1.42NA oil objective lens. Optical sections are taken with 0.2 mm spacing and are subsequently enhanced using constrained iterative deconvolution process by softWoRx software (Applied Precision). The radius of each nucleus is defined as one half of the largest diameter of DAPI staining and measures the distance from FISH signals to the nearest nuclear periphery.

RNA-FISH

LINE-1 RNA-FISH is performed essentially as described in, for example, Wijgerde et al. "Transcription complex stability and chromatin dynamics in vivo," *Nature* 377:209-213 (1995), the entire contents and disclosure of which are hereby incorporated by reference. LINE-1 primer sequences are 5'-TAATACGACTCACTATAGGGGGCTCAGAACT-GAACAAAGA-3' (forward; underline, T7 promoter) and 5'-GCTCATAATGTTGTTCCACCT-3' (reverse), which amplifies a 1041-bp fragment of LINE-1 corresponding to portions of ORF2 and the 3'-UTR (L1MdA2; accession, M13002; 7713 bp). Importantly, this sequence is conserved in other subfamilies of LINE-1. Genomic DNA is used for PCR, and the amplified DNA fragment is purified and used for in vitro transcription followed by reverse transcription to generate a digoxigenin (DIG)-labeled, single-stranded DNA probe.

Example 2

Replication Domain Structure in Embryonic Stem Cells

Replication timing is mapped in mESCs using high-density oligonucleotide arrays, adapting a previously developed retroactive synchronization method. See, e.g., Schubeler et al., "Genome-wide DNA replication profile for *Drosophila melanogaster*: a link between transcription and replication timing," *Nat. Genet.* 32:438-442 (2002); and Gilbert D M, "Temporal order of replication of *Xenopus laevis* 5S ribosomal RNA genes in somatic cells," *PNAS USA* 83:2924-2928 (1986), the entire contents and disclosures of which are hereby incorporated by reference. ESCs are chosen because they provide the opportunity to directly evaluate dynamic changes in the replication program in response to changes in growth conditions (see, e.g., Hiratani et al., "Differentiation-induced replication-timing changes are restricted to AT-rich/long interspersed nuclear element (LINE)-rich iso chores," *PNAS USA* 101:16861-16866 (2004); and Perry et al., "A dynamic switch in the replication timing of key regulator genes in embryonic stem cells upon neural induction," *Cell Cycle* 3:1645-1650 (2004), the entire contents and disclosures of which are hereby incorporated by reference), in contrast to comparisons of separately isolated cell lines that may harbor genetic differences or long-term epigenetic adaptations. Cells are pulse-labeled with BrdU and separated into early and late S-phase fractions by flow cytometry. BrdU-substituted DNA from each fraction is immunoprecipitated with an anti-BrdU antibody, differentially labeled, and co-hybridized to a mouse whole-genome oligonucleotide microarray (Nimblegen Systems) (see FIG. 1A). The ratio of the abundance of each probe in the early and late fraction ["replication timing ratio"=$\log_2$ (Early/Late)] is then used to generate a replication timing profile for the entire genome at 5.8 kb resolution. Replicate experiments in which early and late replicating DNA are reciprocally labeled ("dye-switch") show a high degree of correlation and are averaged ($R^2$ values ranged between 0.86 and 0.95 after loess-smoothing).

Data sets are confirmed by PCR analysis of 18 genes (100% consistent (18/18) in ESCs; 94% consistent (17/18) in NPCs) and by comparison to two previously published replication-timing analyses of 90 individual genes in mESCs (91% consistent (82/90) with the PCR results of the two studies combined) (see, e.g., Hiratani et al., (2004), supra; and Perry et al., (2004), supra). See FIGS. 2A, 2B, and 2C. For example, PCR experiments confirm enrichment of α-globin and β-globin DNA sequences in the expected fractions of immunoprecipitated early and late S-phase DNA samples, respectively. In addition, PCR experiments confirm the expected enrichment of mitochondrial DNA sequences in immunoprecipitated DNA samples from both early and late S-phase (not shown). It is noted that the binary classification of PCR results forces some genes that actually change replication timing to not be classified as such, as with, for example, Crisp1 (later shift), Cdh2, Postn and Mash1 (earlier shift). See FIG. 2A. However, even such subtle changes are detected on the microarray, as shown by the changes in replication timing ratios from ESCs to NPCs.

Figure 1B:
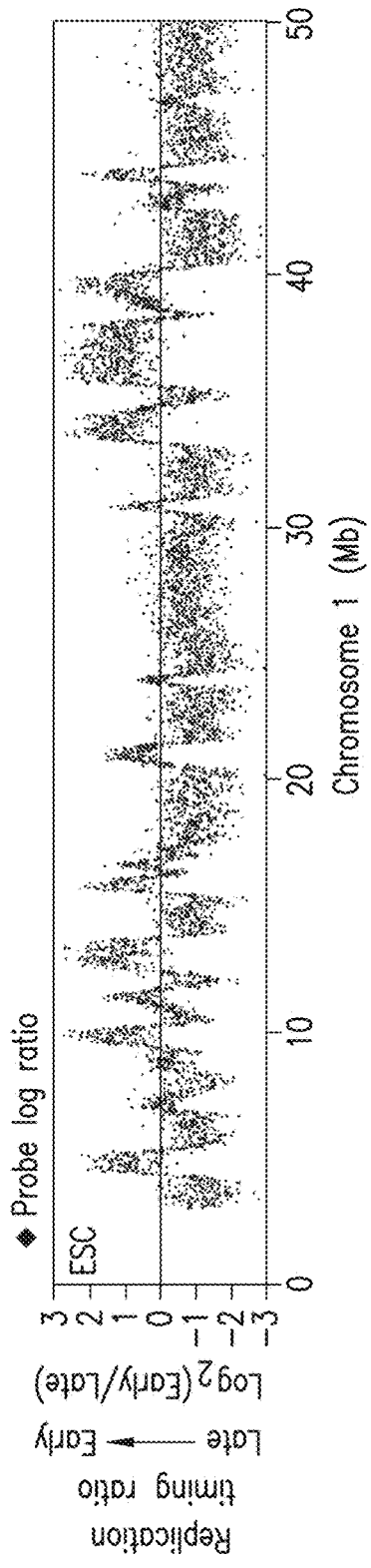
FIG. 1B is a graph showing an exemplary mESC replication timing profile of a segment of chromosome 1 with raw values for probe log ratios [=$\log_2$(Early/Late)] along the chromosome.
Figure 1C:
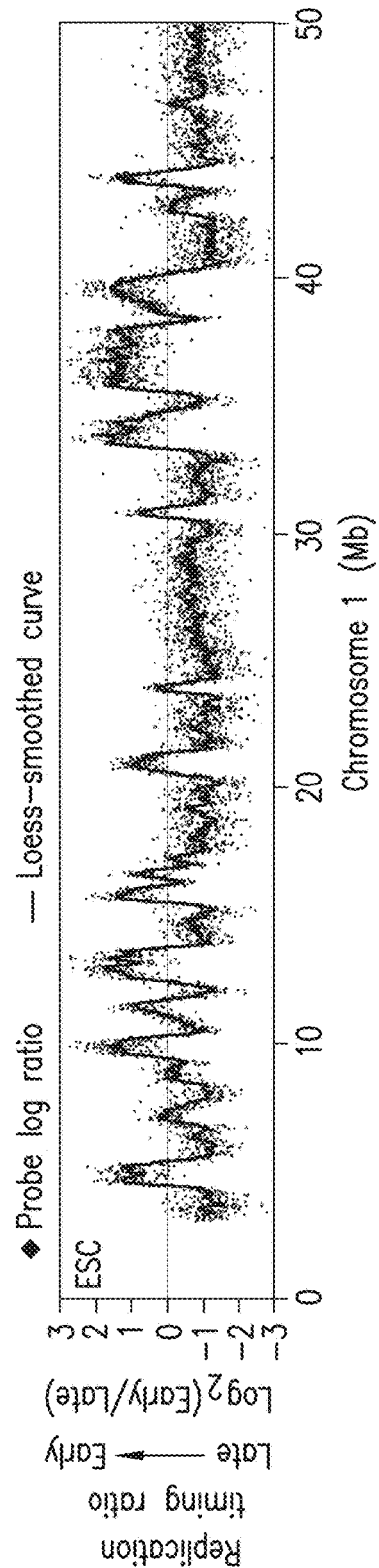
FIG. 1C is a graph showing the same replication timing profile values of a segment of chromosome 1 from FIG. 1A but with a local polynomial smoothing (loess) curve to highlight the clear demarcation between regions of coordinate replication.
Figure 1D:
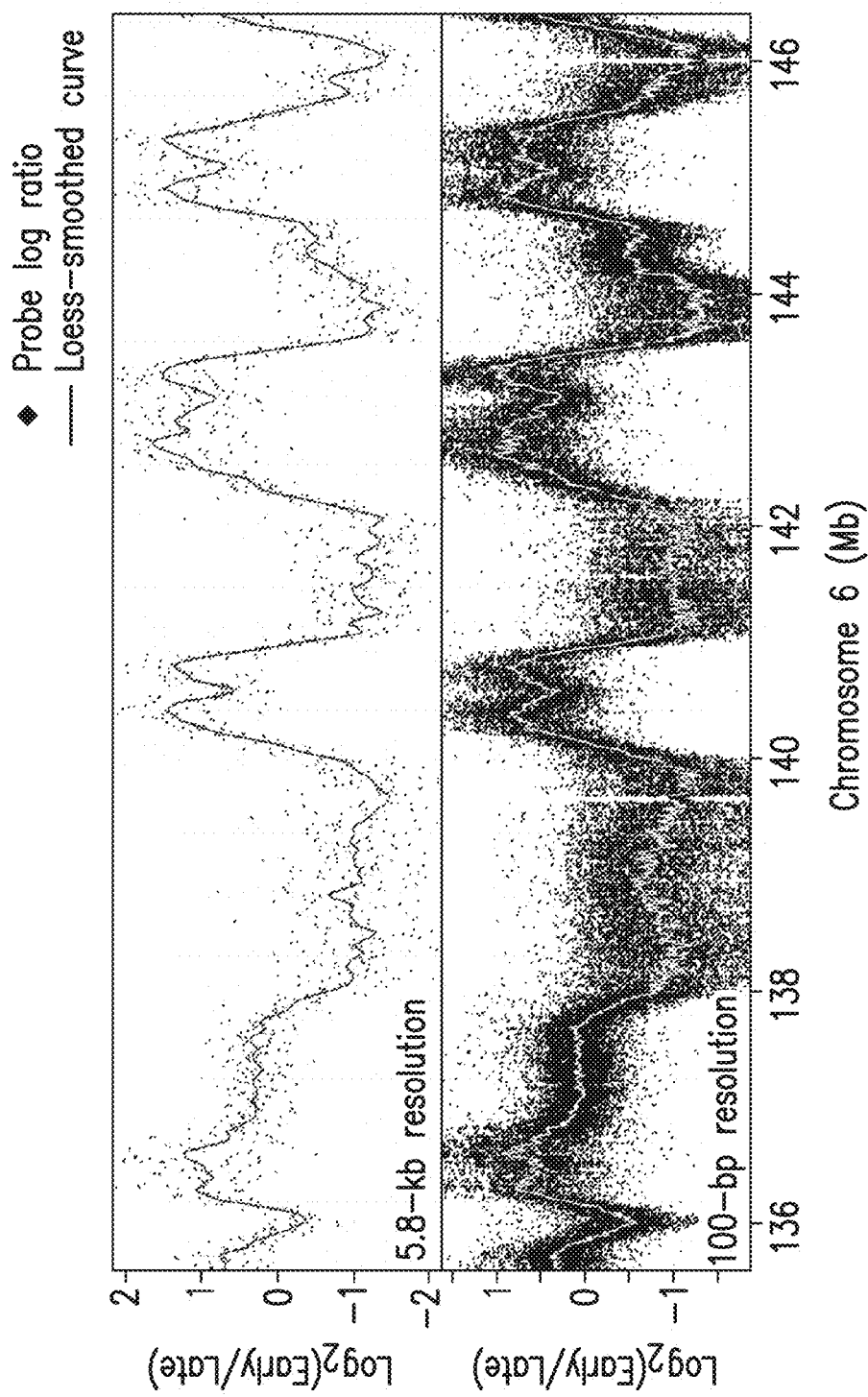
FIG. 1D is a graph showing a comparison of loess-smoothed replication timing profiles generated using either a 5.8 kb resolution CGH array or a 100-bp resolution tiling array with probe log ratio values for the 100-bp resolution tiling array revealing essentially identical smoothed replication timing profiles.
Figure 3:
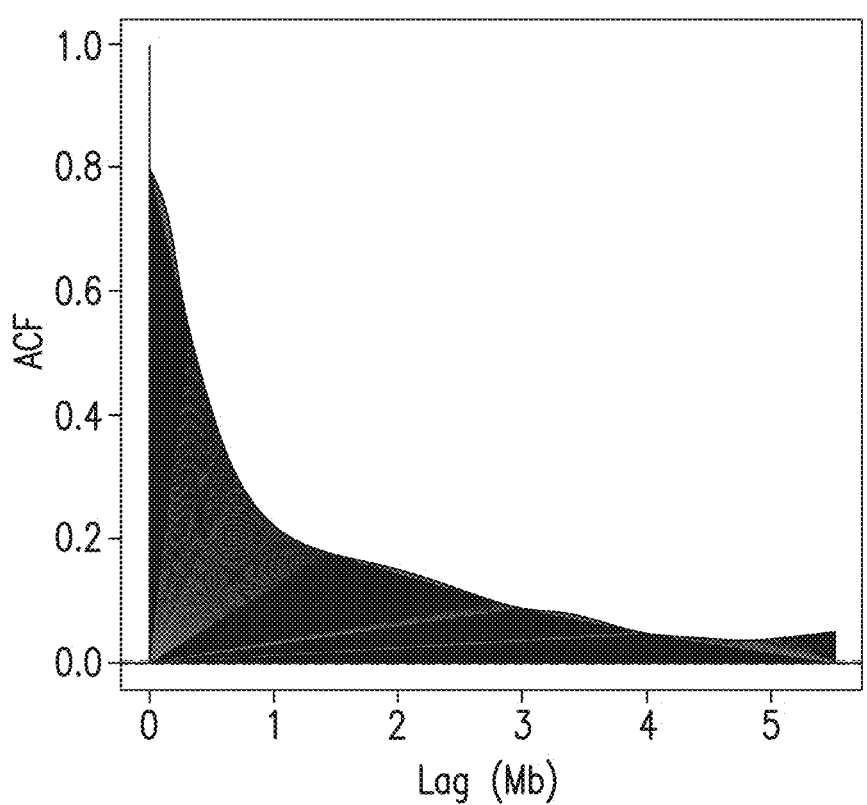
FIG. 3 is a graph showing the autocorrelation analysis of replication timing data, with the autocorrelation function (ACF) indicating the degree of similarity between neighboring data points (y-axis) plotted against inter-probe chromosome distance (Lag) in Mb (x-axis)

FIG. 1B shows the mean replication timing ratio for each probe plotted as a function of chromosomal coordinate for an exemplary 50-Mb segment of chromosome 1, and FIG. 1C shows a loess-smoothed curve fit for the same region. This profile reveals a surprisingly clear demarcation between regions of coordinate replication that is heretofore referred to as "replication domains." To address whether 5.8 kb resolution is sufficient to provide a complete profile of replication domains, the same duplicate preparations of replication intermediates are hybridized to tiling microarrays (one probe every 100 bp) of chromosome 6 and 7. Despite the nearly 60 fold higher probe density, results show an almost indistinguishable smoothed profile (see FIG. 1D). This is consistent with known properties of DNA replication; a 2 hour BrdU pulse is expected to label 200-400 kb stretches of DNA (fork rate 1-2 Kb/min. See, e.g., Jackson et al., "Replicon clusters are stable units of chromosome structure: evidence that nuclear organization contributes to the efficient activation and propagation of S phase in human cells," *J. Cell Biol.* 140:1285-1295 (1998); Norio et al., "Progressive activation of DNA replication initiation in large domains of the immunoglobulin heavy chain locus during B cell development," *Mol Cell* 20:575-587 (2005); and Takebayashi et al., "Regulation of replication at the R/G chromosomal band boundary and pericentromeric heterochromatin of mammalian cells," *Exp. Cell Res.* 304:162-174 (2005), the entire contents and disclosures of which are hereby incorporated by reference), and since multiple replicons across hundreds of kilobases fire synchronously (reviewed in, e.g., Gilbert et al., "Nuclear Structure and DNA Replication," in: DePamphilis M L, Editor *DNA Replication and Human Disease* (Cold Spring Harbor Press, Cold Spring Harbor, N.Y.: 2006)), probes spaced 5.8 kb apart would be expected to replicate at very similar times. Indeed, high autocorrelation of replication timing is observed between neighboring probes (see FIG. 3). Hence, replication timing across the entire genome may be reliably profiled on a single oligonucleotide chip. Replication profiles for all chromosomes may be found at http://www.replicationdomain.org.

Figure 4A:
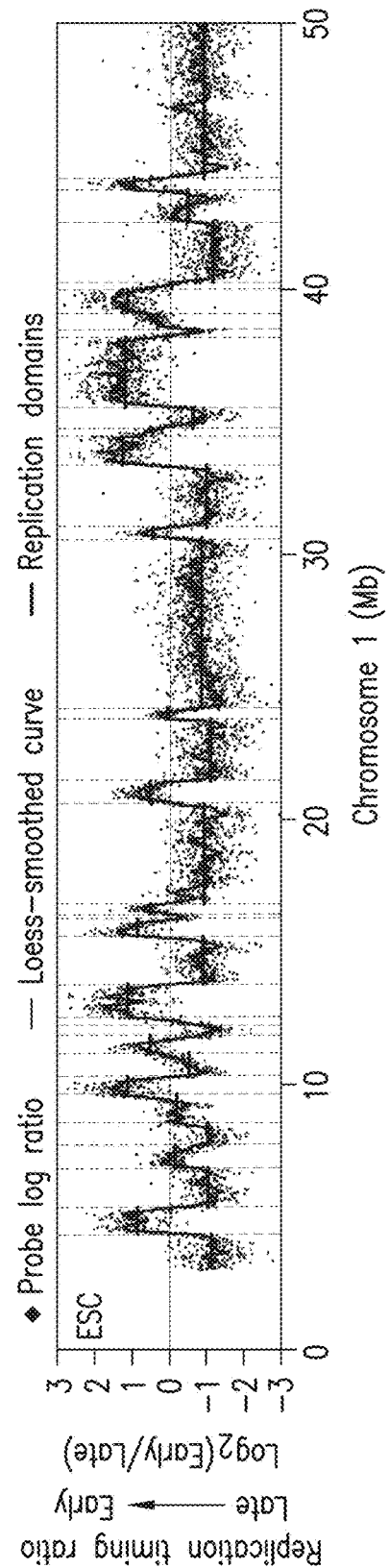
FIG. 4A is a graph showing a loess-smoothed replication timing profile for chromosome 1 from an ESC line with the identification of replication domains (horizontal lines) and their boundaries (dotted lines) by a segmentation algorithm (see, e.g., Venkatraman et al., "A faster circular binary segmentation algorithm for the analysis of array CGH data," Bioinformatics 23:657-663 (2007))
Figure 4B:
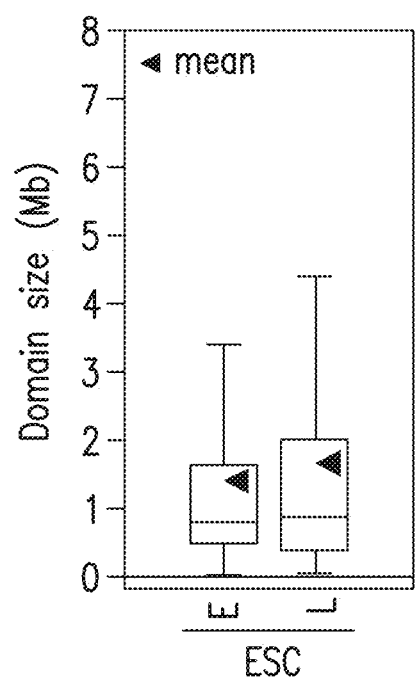
FIG. 4B are graphical box plots of early (E; log ratio>0) and late (L; log ratio<0) replication domain sizes with horizontal bars representing the 10th, 25th, 50th (median), 75th, and 90th percentiles, and with arrowheads representing the mean.
Figure 5A:
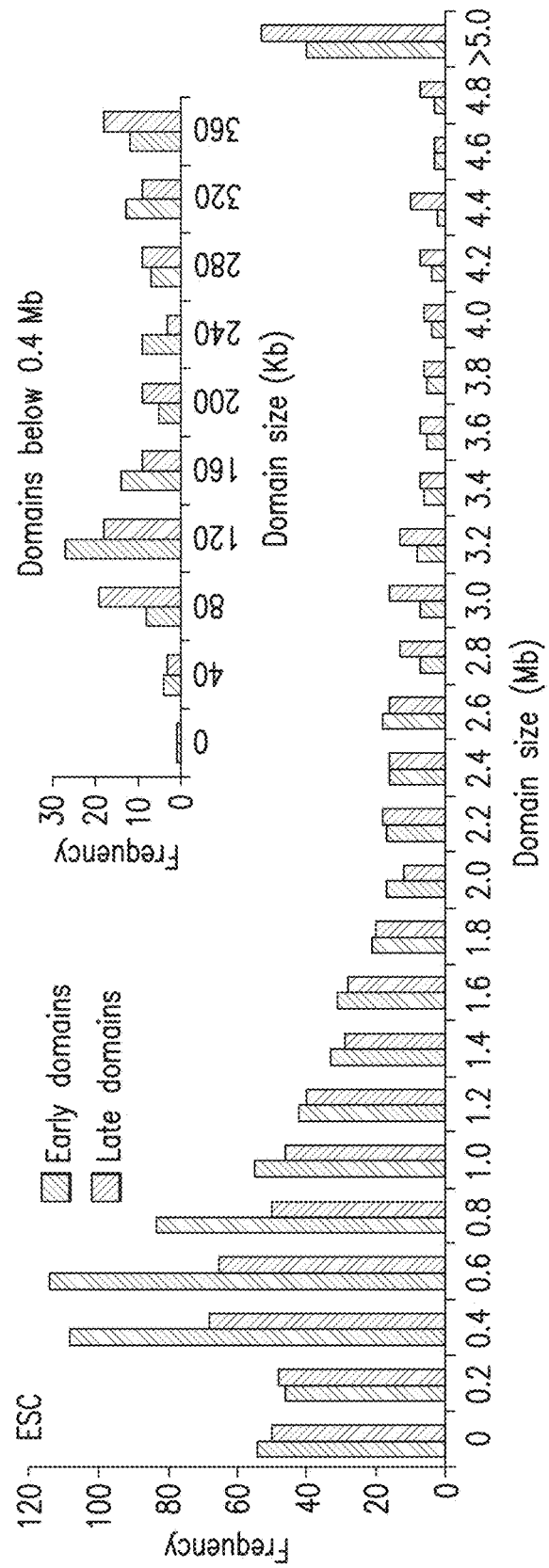
FIG. 5A is a bar graph showing the size distributions of early and late replication domains in ESCs categorized into bins of equal intervals (0.2 Mb or 40 kb below 0.4 Mb) with domains having replication timing ratios above and below zero defined as early and late replication domains, respectively.
Figure 5B:
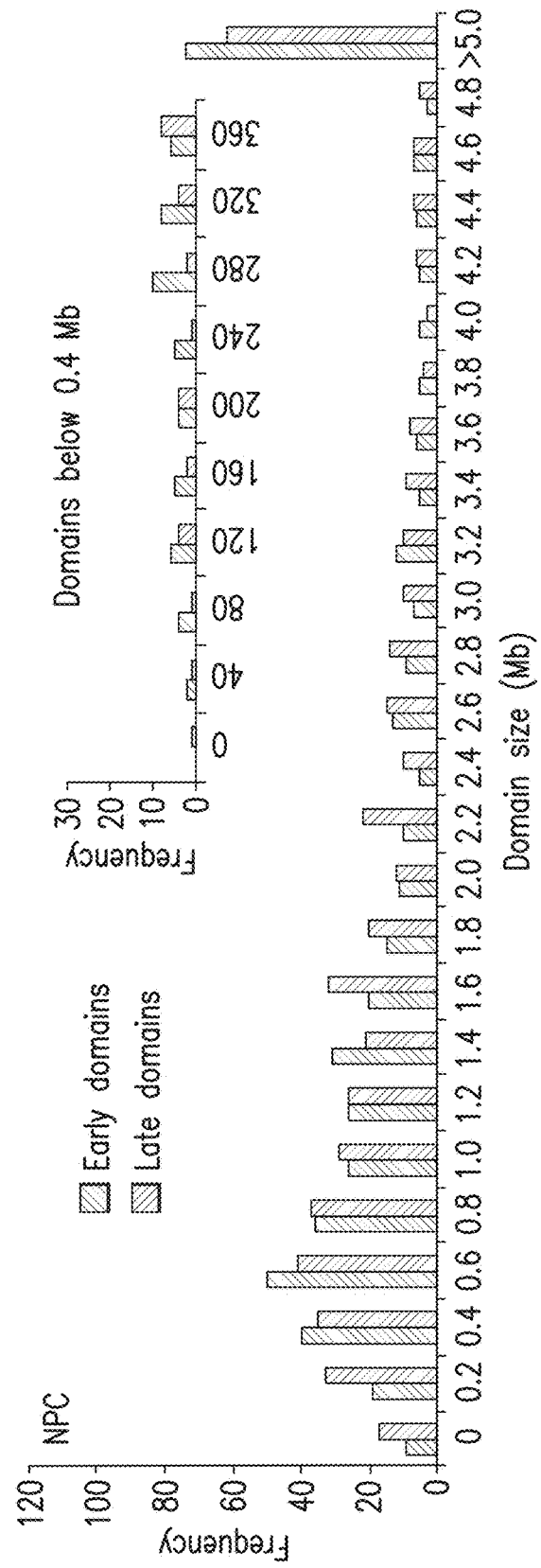
FIG. 5B is a bar graph showing the size distributions of early and late replication domains in neural precursor cells (NPCs) categorized into bins of equal intervals (0.2 Mb or 40 kb below 0.4 Mb) with domains having replication timing ratios above and below zero defined as early and late replication domains, respectively.
Figure 5C:
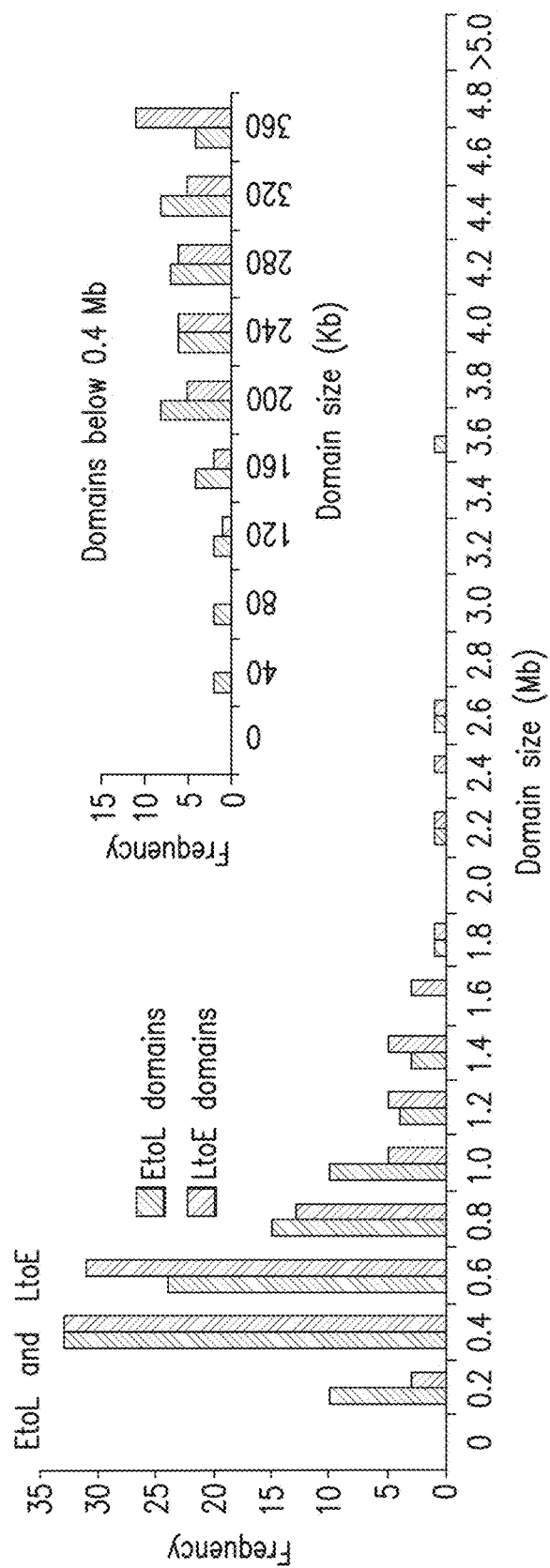
FIG. 5C is a bar graph showing the size distributions of replication domains categorized into bins of equal intervals (0.2 Mb or 40 kb below 0.4 Mb) that change replication timing from early-to-late (EtoL) or late-to-early (LtoE)
Figure 5D:
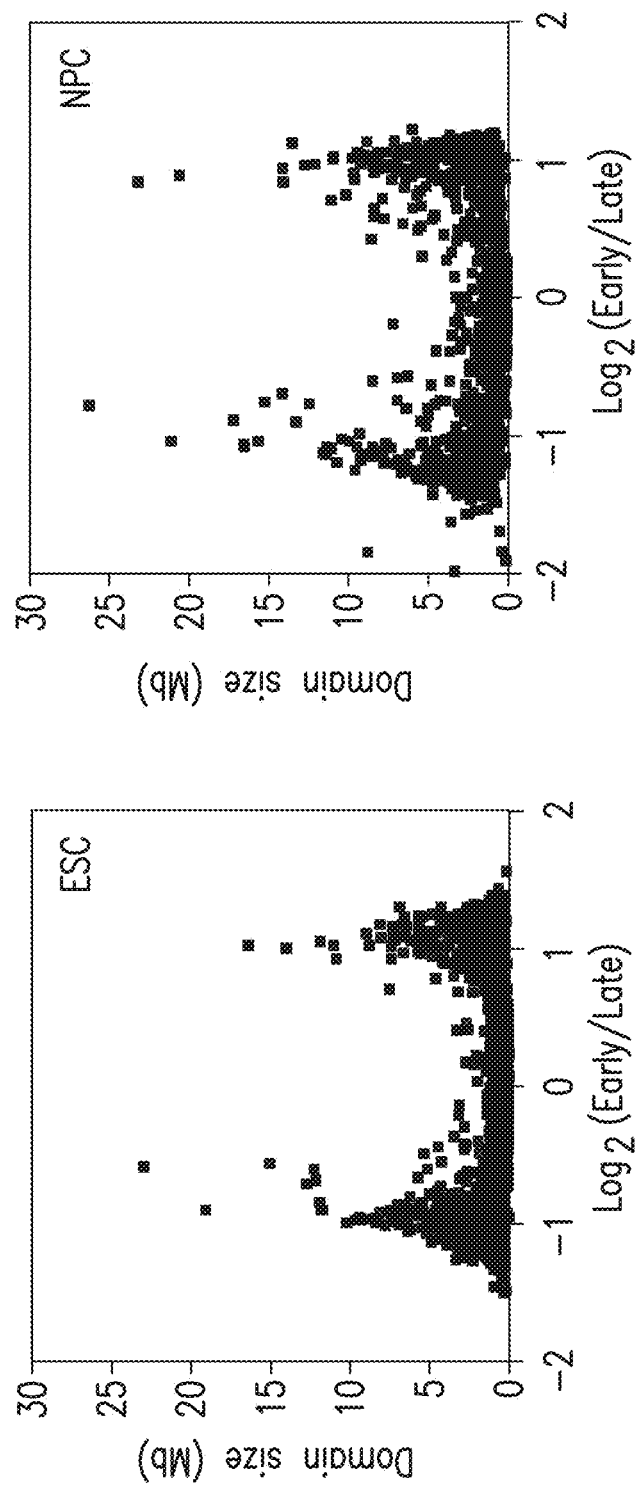
FIG. 5D is a graphical scatter plot of replication timing ratios versus domain size (Mb) in ESCs and NPCs.

To quantify the numbers and positions of replication domains and their boundaries genome-wide, a segmentation algorithm—originally developed to identify copy number differences for comparative genomic hybridization (see, e.g., Venkatraman et al., "A faster circular binary segmentation algorithm for the analysis of array CGH data," *Bioinformatics* 23:657-663 (2007), the entire contents and disclosure of which are hereby incorporated by reference)—is adapted to identify regions of uniform y-axis values (i.e., replication domains), which are illustrated in FIG. 4A. This algorithm generates a data set consisting of the nucleotide map positions for the boundaries of each replication domain. Domain sizes ranged from 200 kb to 2 Mb, with some considerably larger domains (see FIGS. 4B and 5A). These domain sizes may explain why existing ENCODE replication timing data for HeLa cells (see, e.g., Birney et al., "Identification and analysis of functional elements in 1% of the human genome by the ENCODE pilot project," *Nature* 447:799-816 (2007) do not reveal replication domains. The ENCODE regions cover 1% of the genome and consist primarily of scattered 500 kb genomic segments, which may be too small to discern replication domain level chromosome organization. Domains are found to replicate at all times during S-phase, however, domains larger than 2.5 Mb are either very early or very late replicating, suggesting that coordinately replicating regions larger than a certain threshold size tend to replicate at one extreme or another of S-phase (see FIG. 5D). These results are not an artifact of probe density, segmentation algorithm or synchronization method since similar distributions are obtained at 100 bp resolution, using different segmentation parameters, and using an alternative protocol that determines replication timing by probe copy number in S-phase vs. G1-phase without fractionation of S-phase (see, e.g., Woodfine et al., (2004), supra). Similar results may also be obtained with human ESCs.

Example 3

Domain Structure is Conserved Between Independent mESC Lines

Figure 4C:
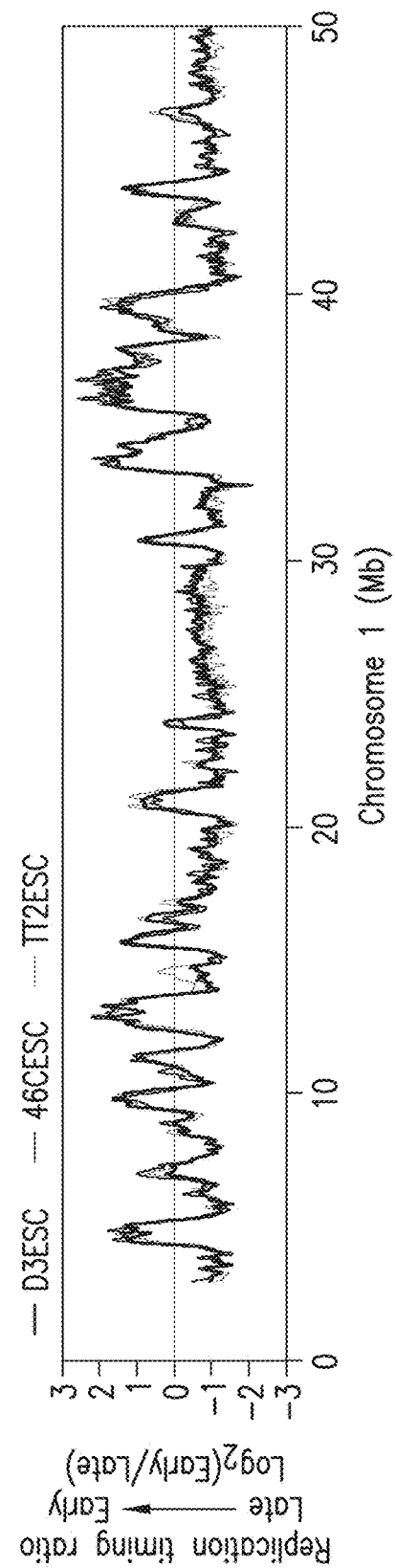
FIG. 4C is a graph comparing three different mESC lines (D3, 46C and TT2) having similar replication domain organization, as revealed by visual inspection of a segment on chromosome 1.
Figures 4D, 4E:
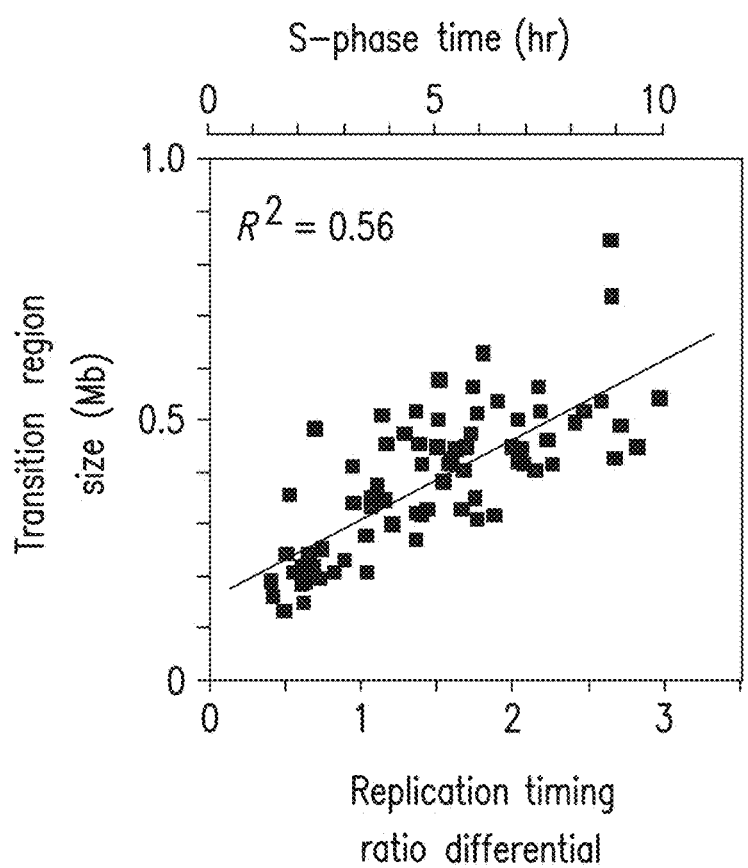
FIG. 4D is a table showing high Pearson's $R^2$ values for pair-wise comparisons of the three different mESC lines (D3, 46C and TT2)
FIG. 4E is a graphical scatter plot of replication timing ratio differentials for transition regions with a time scale (based on the assumption that the replication timing ratio difference of 3 roughly corresponds to an approximately 10 hour S-phase), plotted against the physical distance (Mb) between the ends of 75 pairs (25 for each chromosome) of adjacent replication domains from chromosomes 2, 11 and 16 revealing a positive linear correlation with a slope that is consistent with mammalian replication fork speeds.

The results described above demonstrate that coordinately replicated regions (replication domains) constitute functional units of chromosomes whose boundaries may be molecularly defined. The fact that replication domain boundaries may be so precisely mapped in populations of cells demonstrates that their positions are highly stable from cell cycle to cell cycle. To evaluate whether these boundaries are a conserved property of chromosomes in multiple mESCs, three mESC lines from two independently established mouse inbred strains are compared. Lines D3 and 46C are both derived from the 129 mouse strain and so are nearly identical genetically, but are separated by more than 20 years in cell culture, while TT2 is derived 15 years ago from a C57BL/6×CBA hybrid mouse and is therefore genetically polymorphic (see, e.g., Doetschman et al., (1985), supra; Yagi, et al., (1993), supra; and Ying et al., (2003), supra). Despite the disparate genetic and temporal histories of these three cell lines, their replication profiles are virtually identical (see FIGS. 4C and 4D). This demonstrates that replication domain structure is a highly conserved property of mESCs. Moreover, the recent demonstration that mESCs display considerable cell-to-cell heterogeneity in the expression of certain pluripotency-specific marker genes such as Nanog and Rex1 (see, e.g., Silva et al., "Capturing pluripotency," *Cell* 132:532-536 (2008); and Toyooka et al., (2008), supra, the entire contents and disclosures of which are hereby incorporated by reference) indicates that replication-timing profiles are a substantially more stable and homogeneous property of ESCs than transcription profiles.

Example 4

Transitions Between Replication Domains are Consistent with Large Originless Regions of Uni-directional Replication These results demonstrate that replication timing is regulated at the level of large domains that replicate coordinately, separated by noticeable transition regions. These transition regions resemble the origin-less transition between early and late replicating segments of the immunoglobulin IgH locus (see, e.g., Norio et al., (2005), supra), where a unidirectional replication fork travels 450 kb. If such transition regions throughout the genome represent uni-directional forks, which in mammalian cells travel at the rate of 1-2 kb per minute (see, e.g., Jackson et al., (1998), supra; Norio et al., (2005), supra; and Takebayashi et al., (2005), supra), then it is expected that a linear relationship between the time and distance between each replication domain. The transitions between 25 such replication domain boundaries each from chromosomes 2, 11 and 16 (total of 75) are examined. For each of these boundaries, both the replication timing ratio difference and the kilobase distance from the distal "ledge" of one domain to the proximal "ledge" of the next (see Example 1 above) is scored and plotted relative to each other (see FIG. 4E). Indeed, there is a strong positive linear correlation between the distance and time between replication domains. Since the replication timing ratios for the entire data set ranged from approximately −1.5 to +1.5 which represents an approximately 10 hour S-phase, it is estimated that a uni-directional fork may need to travel 1.4 kb/min on average (ranging from 0.8 to 3.5 kb/minute), which is consistent with mammalian replication fork speeds. Given this linear relationship and the uniform slope of each transition region, this data strongly suggest that the boundaries between replication domains define origin-less regions of uni-directional replication throughout the genome. Regions where individual replication forks need to travel long distances may delineate genomic regions that are particularly vulnerable to DNA damage since stalled forks can form reactive recombination intermediates that lead to chromosome rearrangements. See, e.g., Labib et al., "Replication fork barriers: pausing for a break or stalling for time?," *EMBO Rep.* 8:346-353 (2007), the entire contents and disclosure of which are hereby incorporated by reference. In fact, a survey of a few such boundaries correlates them with genes that are frequently disrupted in cancer. See, e.g., Watanabe et al., "Amplicons on human chromosome 11 q are located in the early/late-switch regions of replication timing," *Genomics* 84:796-805 (2004); and Watanabe et al., "Chromosome-wide assessment of replication timing for human chromosomes 11 q and 21q: disease related genes in timing-switch regions," *Hum Mol Genet* 11:13-21 (2002), the entire contents and disclosure of which are hereby incorporated by reference.

Example 5

Replication Domain Profiles Change in a Characteristic Way during Neural Differentiation If replication timing is regulated during development but is stable within a particular cell type, then replication domain maps may represent cell-type specific "epigenetic signatures." The extent to which replication timing may differ in different cell types is currently not clear, and some studies have concluded that there are few if any differences between cell types. See, e.g., White et al., "DNA replication timing analysis of human chromosome 22 at high resolution and different developmental states," *PNAS USA* 101:17771-17776 (2004); Grasser et al., "Replication timing-correlated spatial chromatin arrangements in cancer and in primate interphase nuclei," *J. Cell Sci.* 121(11):1876-86 (2008); and Costantini et al., "Replication timing, chromosomal bands, and isochores," *PNAS USA* 105:3433-3437 (2008), the entire contents and disclosures of which are hereby incorporated by reference. To directly address the extent to which replication-timing changes occur during the course of differentiation, replication profiles are generated following differentiation of ESCs to neural precursors (NPCs) using two different neural differentiation protocols: one that uses a conditioned medium to differentiate D3 ESCs as embryoid bodies (see, e.g., Rathjen et al., (2003), supra), and one that uses a chemically defined medium to differentiate 46C and TT2 ESCs in adherent monolayers (see, e.g., Ying et al., (2003), supra). Results reveal substantial changes in the replication profile (see FIG. 6A). Even after excluding regional differences of less than 9 consecutive probes (52 kb), 20% of probes show a log ratio change of more than 0.5, as compared to 3% of probes showing differences either between ESC lines or between neural differentiation protocols. Importantly, replication profiles for NPCs are similar regardless of the ESC line or neural differentiation protocol employed (see FIGS. 6B and 6C) and despite differences in the levels of certain gene expression markers between the differentiated cell populations produced by these two protocols (not shown). This demonstrates that the observed changes are characteristic of NPCs rather than having been elicited by conditions associated with a particular neural differentiation protocol (albeit there are more differences between NPCs than between ESCs). It is concluded that specific changes in replication timing take place during the course of neural differentiation to generate a novel replication profile that is characteristic of NPCs, suggesting that replication-timing profiles are stable within particular cell lineages but change significantly in response to major cell fate decisions. Low $R^2$ values for pair-wise comparisons of ESCs and NPCs confirm that substantial changes in replication timing occur upon differentiation (see FIG. 6C).

Example 6

Global Re-organization of Replication Domains during Differentiation

Figure 6A:
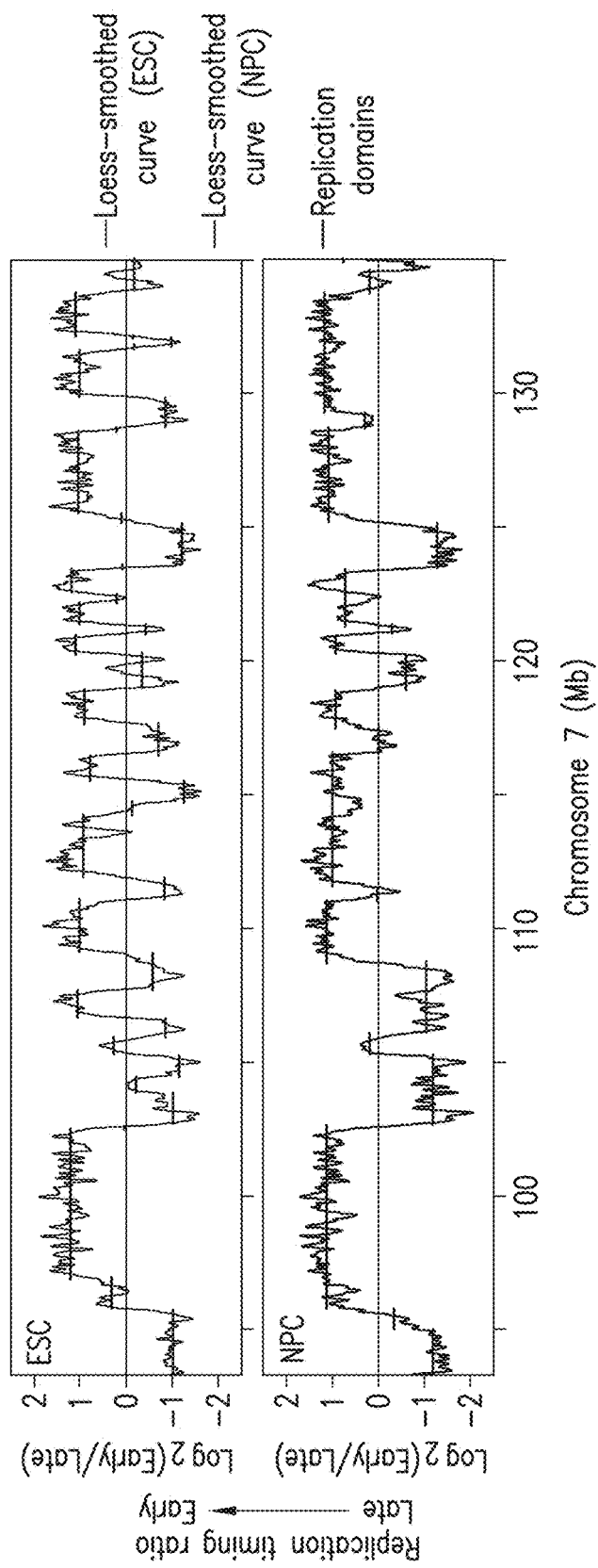
FIG. 6A is a pair of graphs of loess-smoothed replication timing profiles for an exemplary segment of chromosome 7 with replication domains indicated by horizontal lines showing dramatic changes upon differentiation of ESCs to NPCs.
Figure 6B:
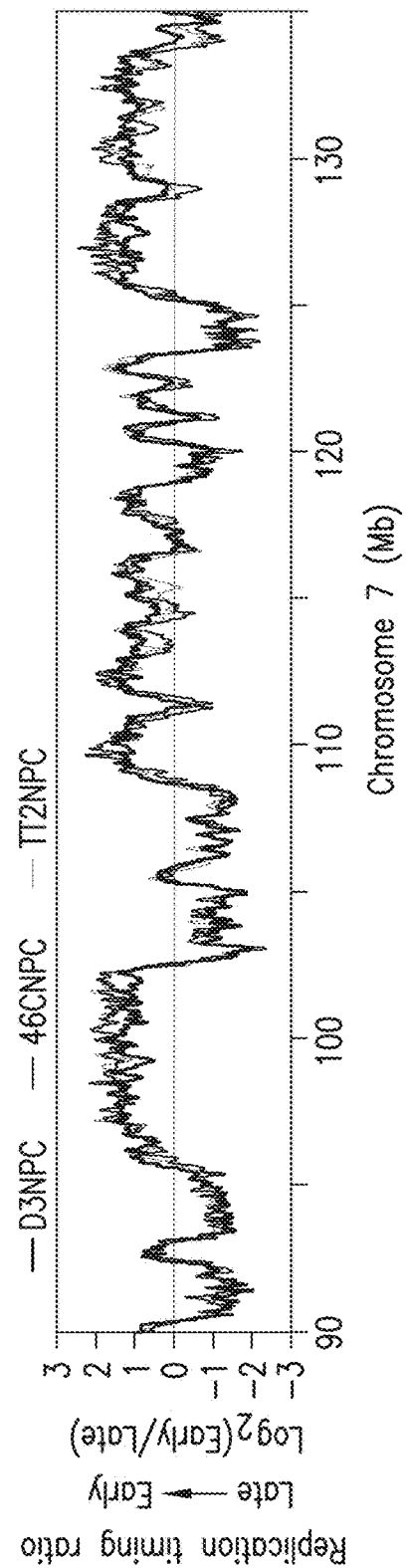
FIG. 6B is a graph of loess-smoothed replication timing profiles for three NPCs derived from distinct neural differentiation schemes showing fairly similar replication timing profiles among them by visual inspection.
Figure 6D:
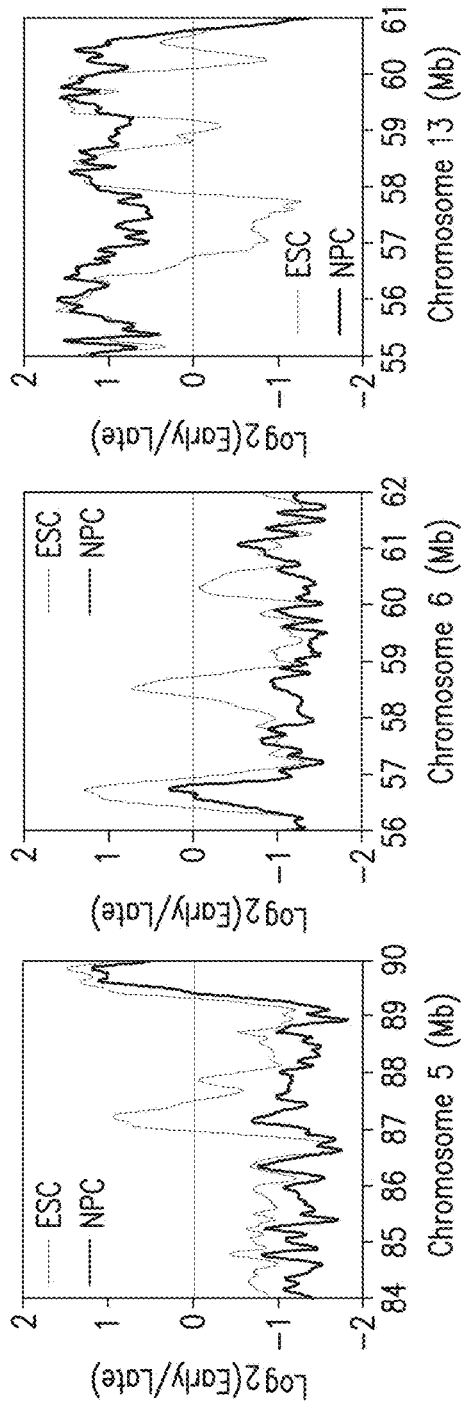
FIG. 6D is a graph of a loess-smoothed replication timing profile for a small segment of chromosome 5 showing an exemplary early-to-late (EtoL) consolidation.
Figure 6E:
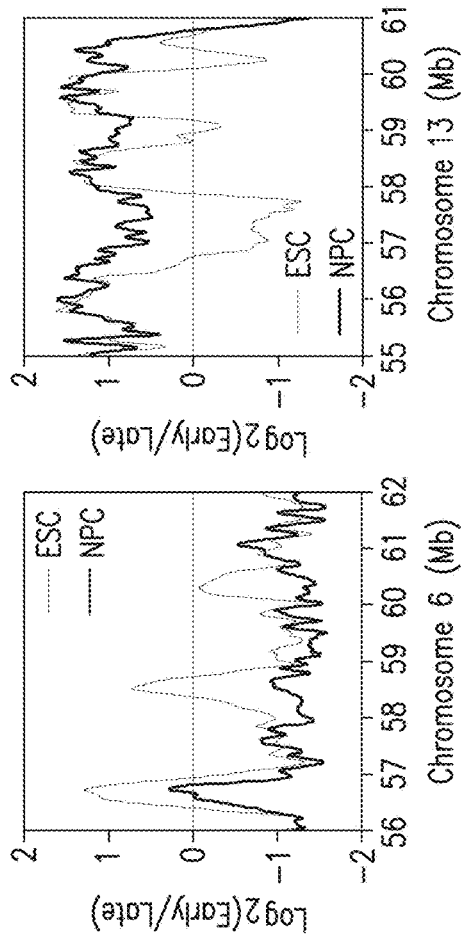
FIG. 6E is a graph of a loess-smoothed replication timing profile for a small segment of chromosome 6 showing an exemplary early-to-late (EtoL) consolidation.
Figure 6F:
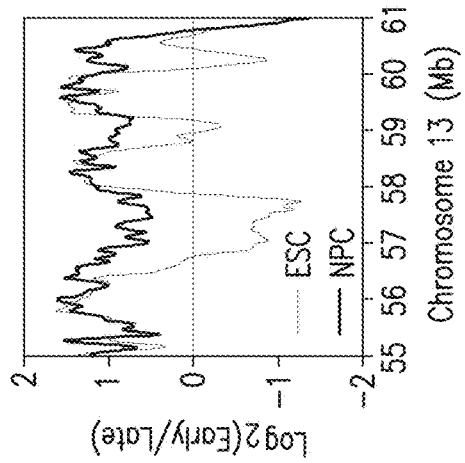
FIG. 6F is a graph of a loess-smoothed replication timing profile for a small segment of chromosome 13 showing an exemplary late-to-early (LtoE) consolidation.
Figure 6G:
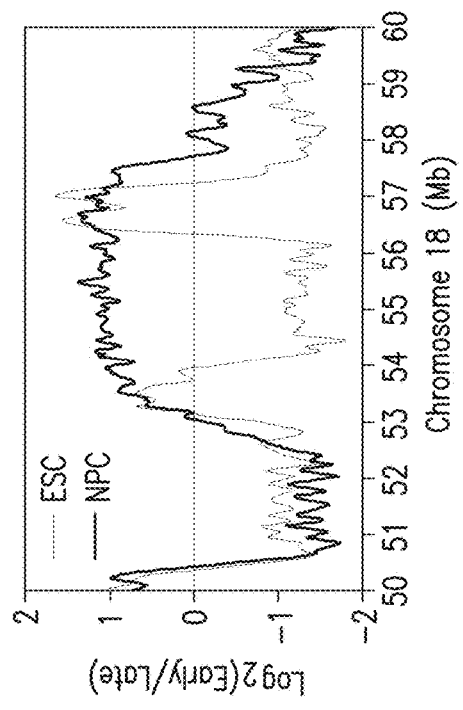
FIG. 6G is a graph of a loess-smoothed replication timing profile for a small segment of chromosome 18 showing an exemplary late-to-early (LtoE) consolidation.
Figure 6H:
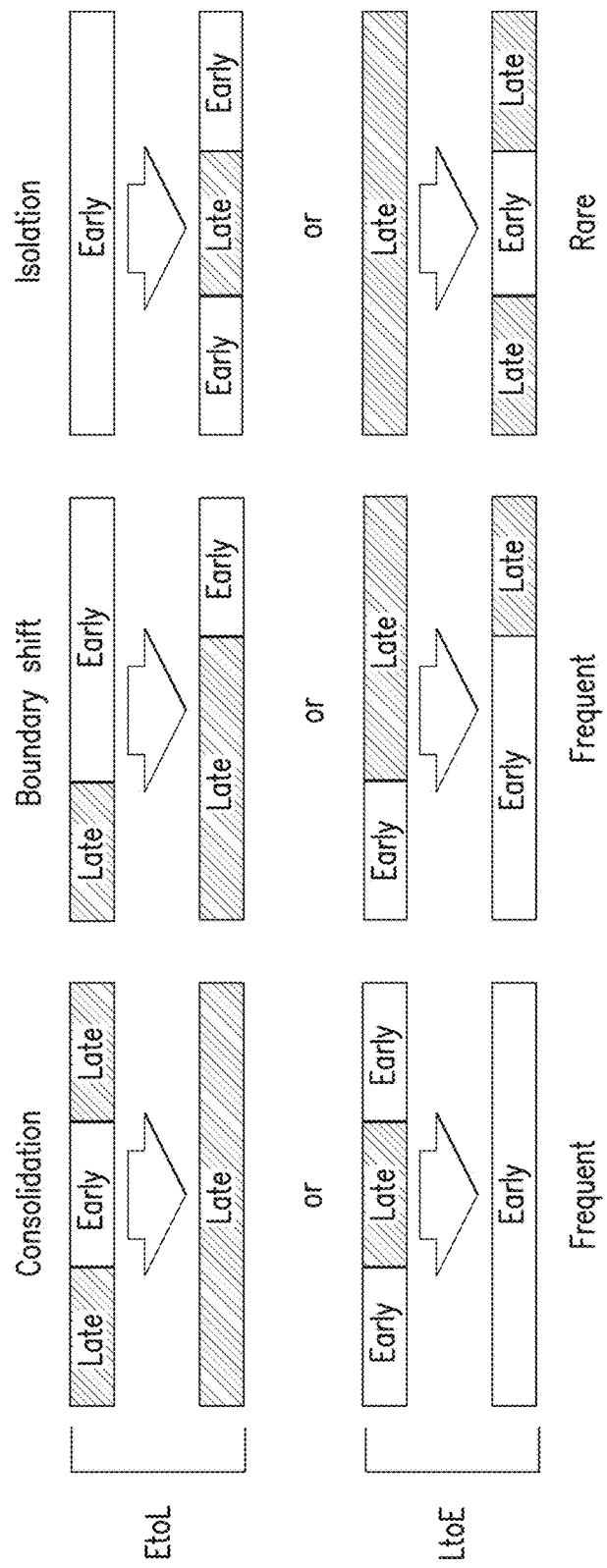
FIG. 6H is a schematic representation of replication domain consolidation, boundary shift, and isolation events that may occur during differentiation.
Figures 6I, 6K:
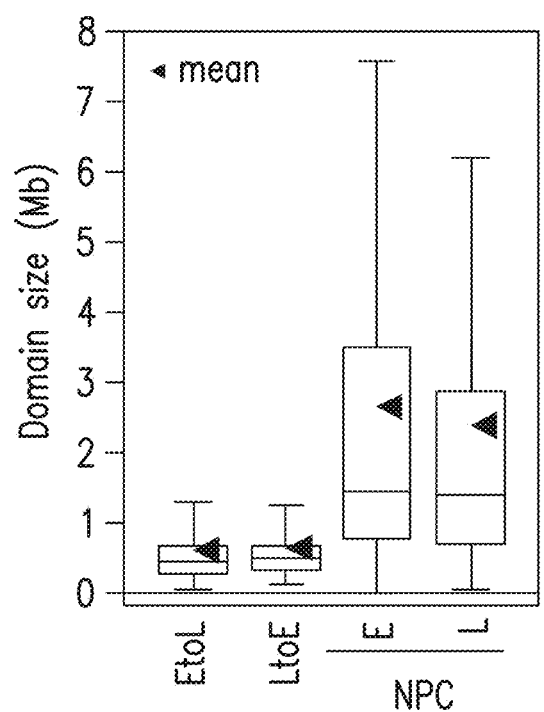
FIG. 6I is a table summarizing replication domain properties from ESCs and NPCs.
FIG. 6K are graphical box plots of the sizes of domains that changed replication timing (EtoL and LtoE), as well as early and late replicating domains in NPCs with horizontal bars representing the 10th, 25th, 50th (median), 75th, and 90th percentiles, and with arrowheads representing the mean.

Unexpectedly, it is found that replication-timing changes induced by differentiation resulted in a dramatic change in the number and sizes of replication domains (see FIG. 6A). Small domains that were replicated at different times in ESCs frequently merge to become one larger coordinately replicated domain (see FIGS. 6D, 6E, 6F, and 6G). This reorganization is referred to as domain "consolidation" (see FIG. 6H). Also frequent are events in which the positions of boundaries shifted (referred to as a "boundary shift"). Boundary shifts occur equally through the encroachment of late domains into early domains and vice versa, so they do not affect the overall size or number of replication domains. In rare cases, the emergence of new smaller domains from within a larger domain (referred to as "isolation") is observed (see FIG. 6H). Visual inspection of 46 domains that changed replication timing [22 LtoE (Late in ESCs to Early in NPCs) and 24 EtoL (Early-to-Late)] confirms that "consolidation" and "boundary shift" events are equally frequent (43% and 50%, respectively), while "isolation" events are rare (7%). Domain consolidation is significant with a 40% reduction in the number of domains and a corresponding increase in the size of domains (see FIG. 6I and FIGS. 5A and 5B) in NPCs compared to ESCs. Importantly, consolidation is widespread, occurring on all chromosomes (see FIG. 6J). Interestingly, domains that switched replication timing (EtoL and LtoE) are smaller and more uniform in size (400-800 kb) than the distribution of domains as a whole (see FIG. 6K and FIG. 5C). EtoL and LtoE domains show smaller and tighter distribution than domains in general from NPCs (see FIG. 6K) or ESCs (see FIG. 4B). This size range (400-800 kb) is very close to cytogenetic estimates of the amount of DNA within individual replication foci. See, e.g., Ma et al., "Spatial and temporal dynamics of DNA replication sites in mammalian cells," *J. Cell Biol.* 143:1415-1425 (1998), the entire contents and disclosure of which are hereby incorporated by reference. Together, these data suggest that replication domains are made up of smaller units that may correspond to replication foci or "replicon clusters" and that replication timing changes may occur at the level of these smaller units.

Example 7

Consolidation Aliens Replication Domains to Isochore GC Content

Figure 7A:
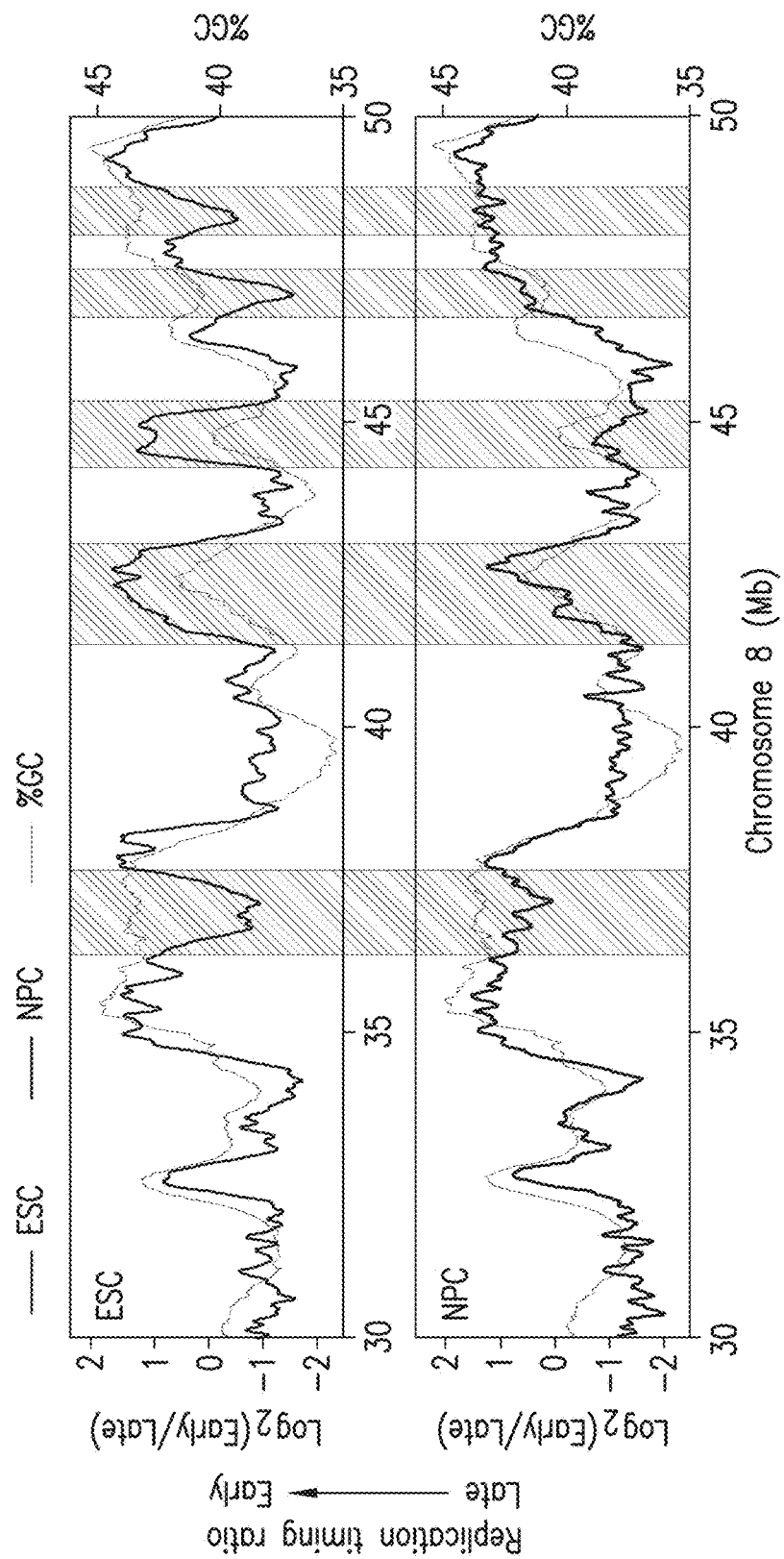
FIG. 7A is a pair of graphs showing loess-smoothed replication timing profiles of ESCs (top) and NPCs (bottom) compared to % GC computed as moving averages of 500 kb windows of GC content for a segment of chromosome 8 with grey highlighted areas showing regions where differentiation aligns replication timing to GC/LINE-1 content.
Figure 7B:
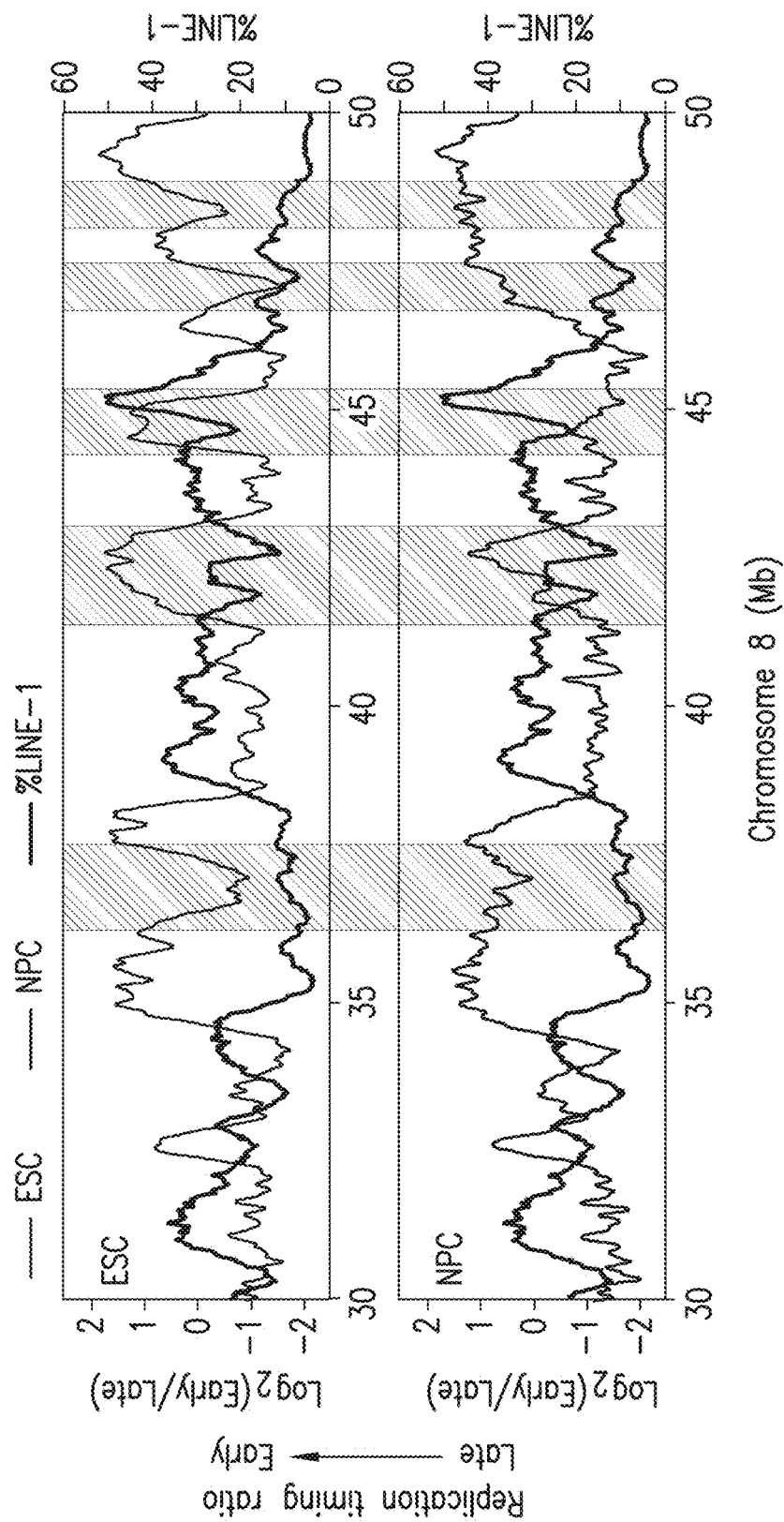
FIG. 7B is a pair of graphs showing loess-smoothed replication timing profiles of ESCs (top) and NPCs (bottom) compared to % LINE-1 computed as moving averages of 500-kb windows of LINE-1 content for a segment of chromosome 8 with grey highlighted areas showing regions where differentiation aligns replication timing to GC/LINE-1 content.
Figure 7C:
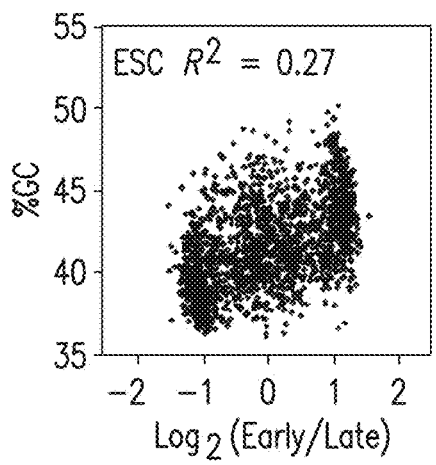
FIG. 7C is a graphical scatter plot showing average replication timing ratios of replication domains in ESCs plotted against their % GC content with Pearson's $R^2$ values shown.
Figure 7D:
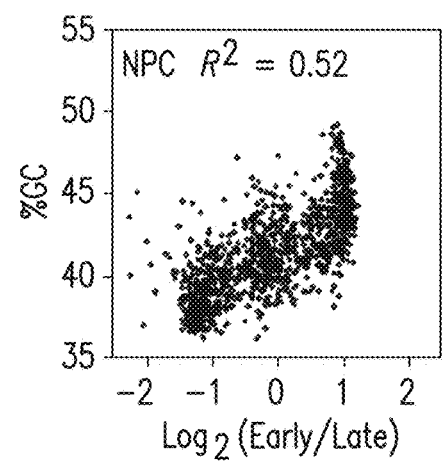
FIG. 7D is a graphical scatter plot showing average replication timing ratios of replication domains in NPCs plotted against their % GC content with Pearson's $R^2$ values shown.
Figure 7E:
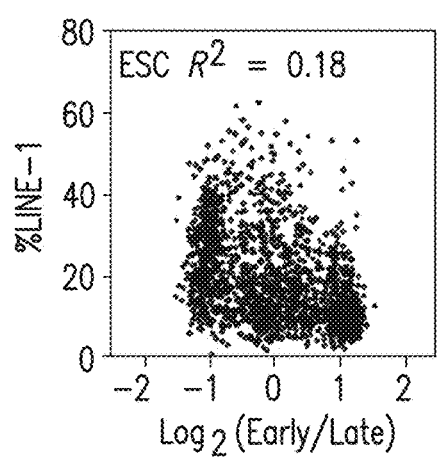
FIG. 7E is a graphical scatter plot showing average replication timing ratios of replication domains in ESCs plotted against their % LINE-1 content with Pearson's $R^2$ values shown.
Figure 7F:
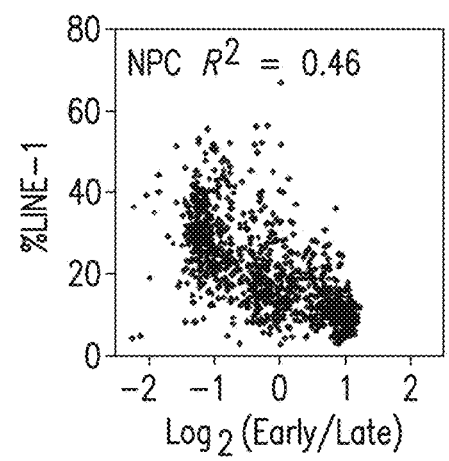
FIG. 7F is a graphical scatter plot showing average replication timing ratios of replication domains in NPCs plotted against their % LINE-1 content with Pearson's $R^2$ values shown.
Figure 7I:
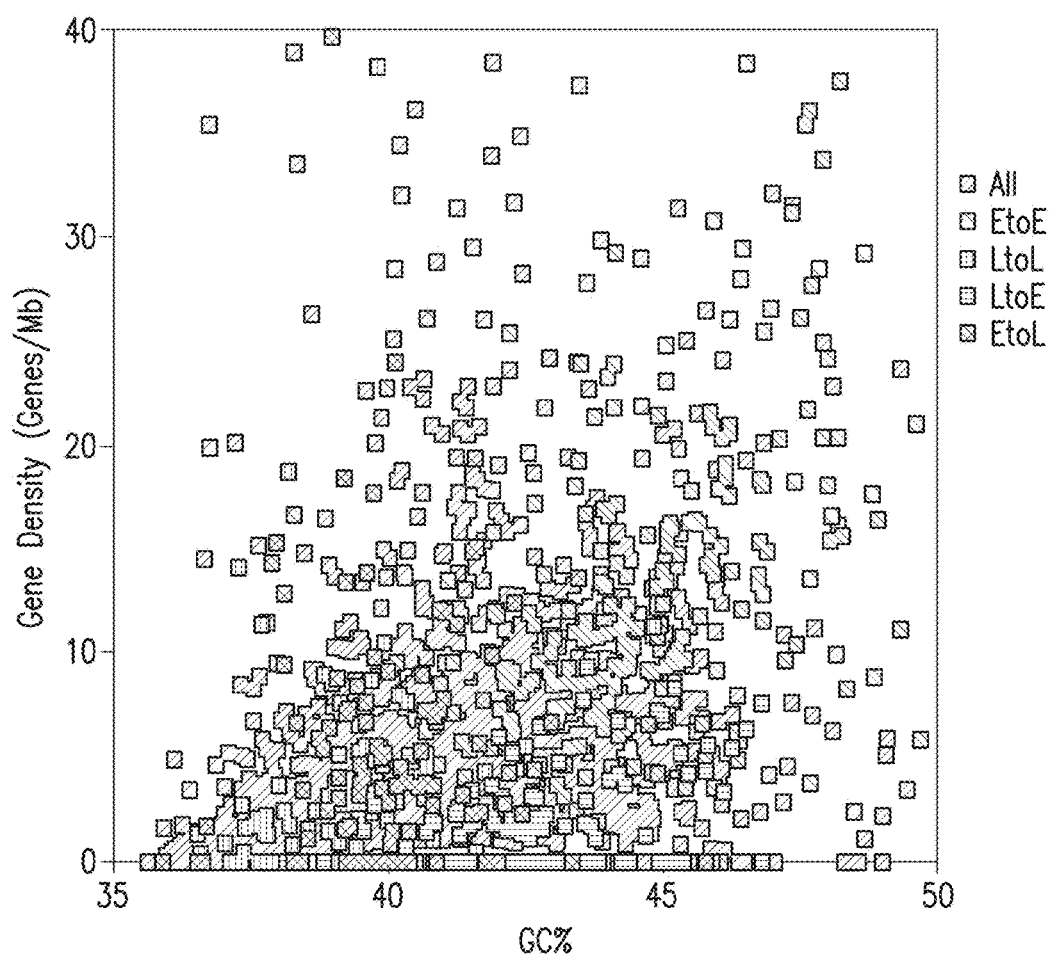
FIG. 7I is a graphical scatter plot of % GC content and gene density showing that EtoE, LtoL, LtoE, and EtoL domains are generally GC-rich/gene-rich, GC-poor/gene-poor, GC-rich/gene-poor and GC-poor/gene-rich, respectively.
Figures 7J, 7K:
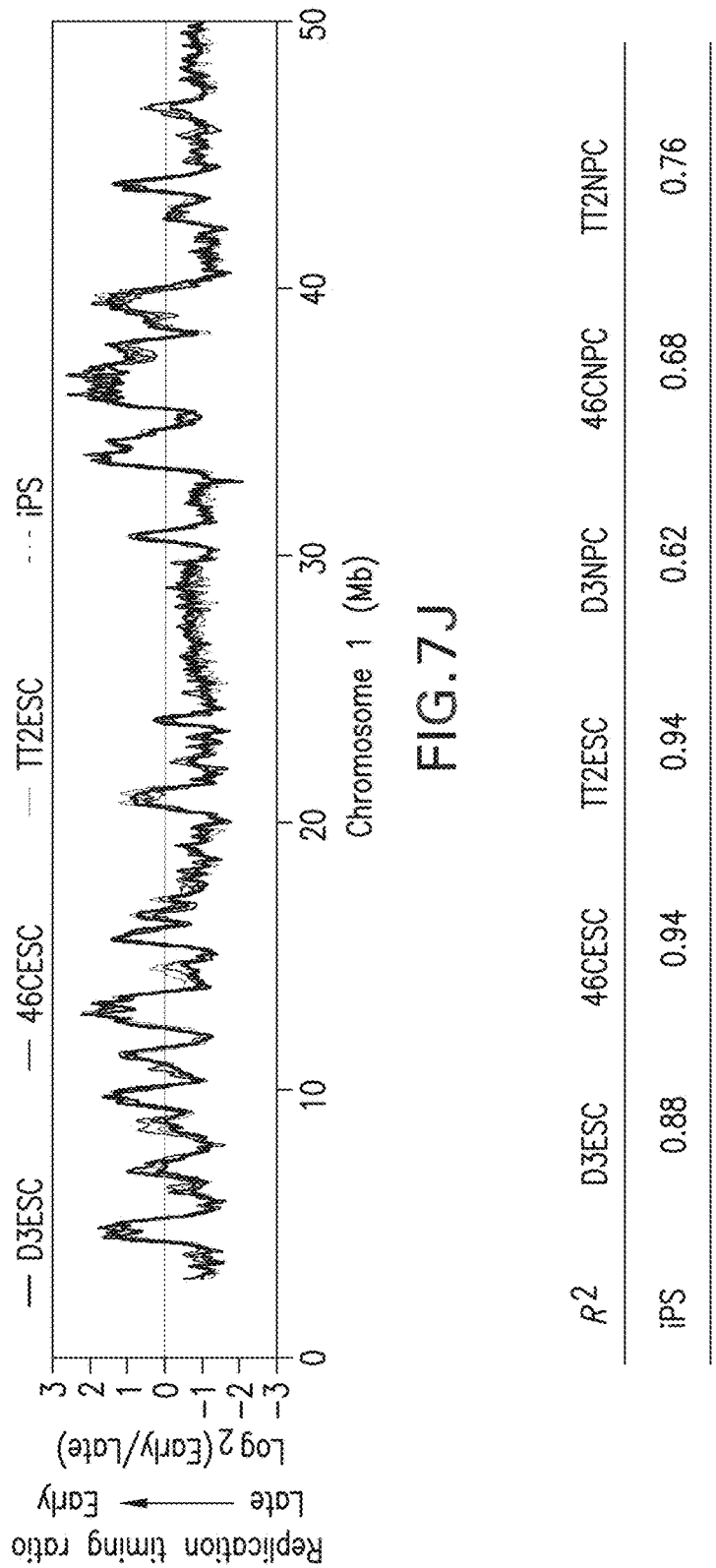
FIG. 7J is a graph of replication timing profiles from mESCs and induced pluripotent stem (iPS) cells showing that iPS cells match the replication timing profiles of ESCs by visual inspection.
FIG. 7K is a table showing Pearson's $R^2$ values for pair-wise comparisons of iPS cells to ESCs and NPCs showing high correlation with ESCs but not NPCs.

Mammalian chromosomes are organized into alternating AT- and GC-rich stretches of sequence called isochores, which are rich and poor in LINE-1 transposable elements, respectively. See, e.g., Bernardi G, "Isochores and the evolutionary genomics of vertebrates," *Gene* 241:3-17 (2000). Prior studies evaluating replication timing of various segments of the human genome have reported a strong positive correlation between GC content and early replication. See, e.g., Woodfine et al., (2004), supra; Schmegner et al., "Isochores and replication time zones: a perfect match," *Cytogenet. Genome Res.* 116:167-172 (2007); Costantini et al., (2008), supra; and Watanabe et al., (2002), supra, the entire contents and disclosures of which are hereby incorporated by reference. Such a correlation is also detected herein (see FIG. 7), but the degree of this correlation is not static. In fact, the correlation between replication domains and isochores is not impressively strong in mESCs but improves substantially during differentiation. This is evident by visual comparison of replication profiles to GC and LINE-1 density in ESCs vs. NPCs (see FIGS. 7A and 7B). To confirm this alignment genome wide, the GC or LINE-1 content of the DNA sequences within the boundaries of each replication domain is plotted vs. the replication time of each domain. For both sequence properties, the correlation becomes much stronger in NPCs than in ESCs (see FIGS. 7C, 7D, 7E, and 7F). Moreover, domains that change replication timing usually acquire a temporal profile in line with their isochore sequence composition. In other words, EtoL (Early-to-Late) domains are low in GC and high in LINE-1 density and resemble LtoL (Late-to-Late) domains, while LtoE (Late-to-Early) domains have an intermediate GC content and a relatively low LINE-1 density and resemble EtoE (Early-to-Early) domains (see FIG. 7G).

Example 8

Domains that Change Replication Timing have Unusual Sequence Composition

GC vs. AT rich isochores are also known to be gene rich vs. gene poor. See, e.g., Costantini et al. "An isochore map of human chromosomes," *Genome Res* 16:536-541 (2006), the entire contents and disclosure of which are hereby incorporated by reference. As expected, gene density within replication domains largely follows the rules of isochore replication timing: in both ESCs and NPCs, domains that have a high density of genes are early replicating and, for the most part, GC-rich. In fact, 75% of genes replicate early in both cell types (i.e., positive replication timing ratios) and, as expected, EtoE and LtoL domains are GC-rich/gene-rich and GC-poor/gene-poor, respectively (see FIG. 7G). Surprisingly, although the alignment to isochore GC/LINE-1 density increases during differentiation, the correlation between gene density and early replication does not (see FIG. 7H). This is due to the fact that LtoE and EtoL domains exhibit the unusual properties of being GC-rich/gene-poor and GC-poor/gene-rich, respectively (see FIGS. 7G and 7I). Thus, GC/LINE-1 density and gene density are properties of isochores that may be uncoupled. Moreover, these results demonstrate that replication timing is not a simple reflection of either local gene density or isochore GC content, as has been proposed by others. See, e.g., Grasser et al., (2008), supra; and Costantini et al., (2008), supra. Without being bound by any theory, it is believed that segments that change replication timing have an unusual combination of GC content and gene density, providing a potential means to predict chromosome domains that change replication timing.

Example 9

Replication Domain Structure of Induced Pluripotent Stem (iPS) Cells Matches that of ESCs The results described above suggest that replication-timing profiles in ESCs may provide a unique signature for identification of the pluripotent state. A prediction of this hypothesis is that induced pluripotent stem (iPS) cells, in which an adult differentiated cell has been reverted back to the pluripotent state, should share replication profiles with ESCs. To address this prediction, replication profiles for iPS cells (see, e.g., Takahashi et al., "Induction of pluripotent stem cells from mouse embryonic and adult fibroblast cultures by defined factors." *Cell* 126:663-676 (2006), the entire contents and disclosure of which are hereby incorporated by reference) are generated, which are re-programmed from tail-tip fibroblasts derived from a 129×BL-6 hybrid strain of mice as described in, for example, Hanna et al., "Treatment of sickle cell anemia mouse model with iPS cells generated from autologous skin," *Science* 318:1920-1923 (2007), the entire contents and disclosure of which are hereby incorporated by reference). Indeed, iPS cells show a profile that is virtually indistinguishable from other ESCs (see FIGS. 7J and 7K). These results provide additional evidence that iPS cells are indeed very similar to ESCs and that the property of smaller replication domains that disrupt the alignment of replication timing to isochores is a novel characteristic of the pluripotent state. Moreover, these results suggest a means to profile or identify cell types, including pluripotent cell types, based on replication domain organization, which appears to be considerably more stable than transcription profiles.

Example 10

Replication Timing and Transcription Chances during Differentiation

Correlation Between Early Replication and Transcription in ESCs and NPCs

Figure 8E:
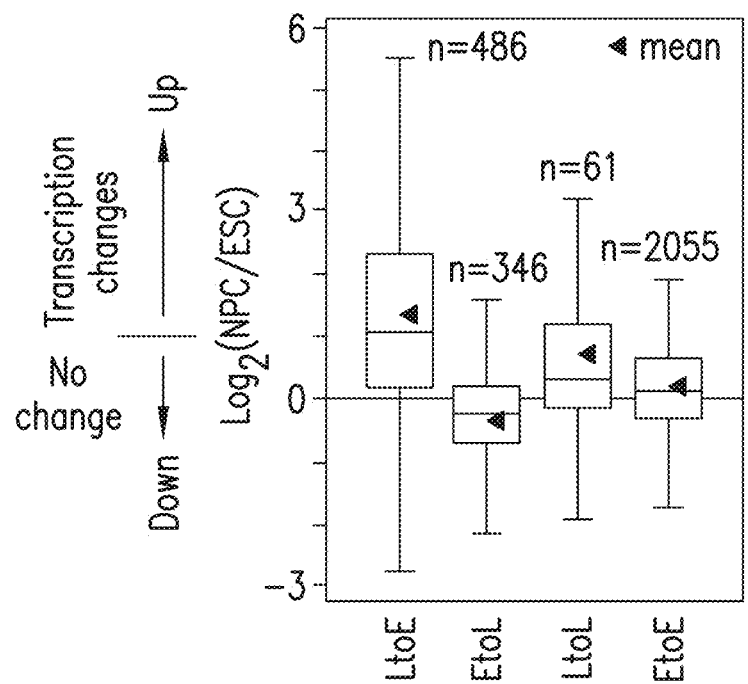
FIG. 8E is a pair of graphical box plots showing the fold changes in transcription [=$\log_2$(NPC/ESC)] of LtoE, EtoL, LtoL and EtoE genes with RefSeq genes having the 5% greatest replication timing changes defined as EtoL and LtoE while those having the least replication timing changes (lowest 20 percentile) that maintain replication timing ratios above 0.5 or below −0.5 being defined as EtoE and LtoL, respectively, with horizontal bars representing the 10th, 25th, 50th (median), 75th, and 90th percentiles, and with arrowheads representing the mean.

Genes that are transcribed are generally early replicating, while genes that are late replicating are almost always silent. However, exceptions to this rule have been described. See, e.g., Gilbert D M, "Replication timing and transcriptional control: beyond cause and effect," *Curr. Opin. Cell Biol.* 14:377-383 (2002); Goren et al., "Replicating by the clock," *Nat. Rev. Mol. Cell Biol.* 4:25-32 (2003); and Schwaiger et al., "A question of timing: emerging links between transcription and replication," *Curr. Opin. Genet. Dev.* 16:177-183 (2006)). No study has comprehensively examined the changes in gene expression as they relate to changes in replication timing. To address this issue, the steady state levels of annotated gene transcripts are analyzed before and after differentiation to NPCs using Affymetrix GeneChips. Regardless of whether levels, density or number of active genes are examined, either at the level of domains (see FIGS. 8A and 8B) or individual genes (see FIGS. 8C and 8D), both differentiation states show a strong and similar positive correlation between early replication and transcription. Logistic regression (inner line) and 95% confidence intervals (outer lines) reveal a strong correlation in both ESCs (see FIG. 8C) and NPCs (see FIG. 8D). By the Likelihood Ratio test (a goodness of fit test), the fitted model is significantly different ($p<2\times10-16$ for both ESCs and NPCs) from that of a null hypothesis in which replication timing has no effect on transcription.

Figure 8F:
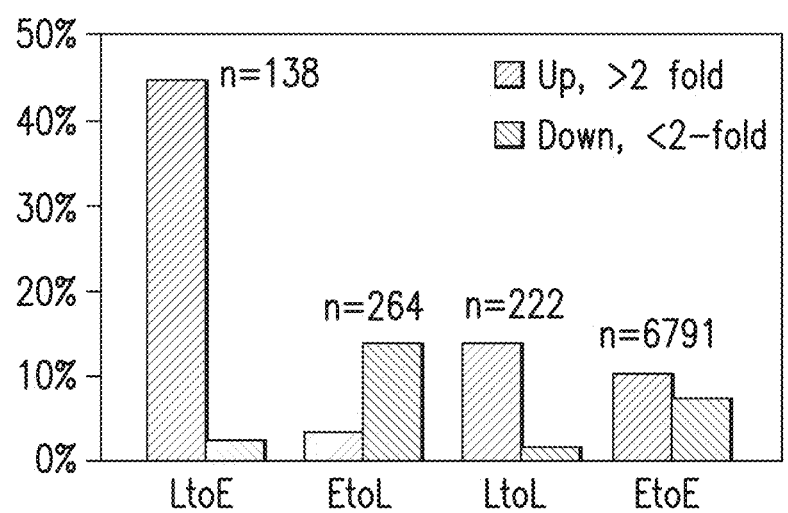
FIG. 8F is a bar graph showing the relative percentage of "two-fold up" or "two-fold down" regulated genes within LtoE, EtoL, LtoL and EtoE domains as defined in FIG. 7G.

Consistent with previous findings across a portion of the *Drosophila* genome (see, e.g., MacAlpine et al., "Coordination of replication and transcription along a *Drosophila* chromosome." *Genes Dev.* 18:3094-3105 (2004)), this positive correlation is greater when integrated over large regions (approximately 600 kb for ESCs and NPCs vs. 180 kb in *Drosophila*). The maintenance of this statistical relationship during differentiation may be accounted for by the directionality of transcriptional changes within each domain (see FIGS. 8E and 8F). At the level of individual genes, LtoE genes are mostly upregulated while EtoL genes showed a weak tendency to be downregulated. At the level of domains, amongst those domains that contain at least one RefSeq gene (NCBI annotation at http://www.ncbi.nlm.nih.gov/RefSeq/), the majority of LtoE domains contain only upregulated genes, while EtoL domains contain mostly downregulated or unchanged genes (see FIG. 8G).

Figure 8H:
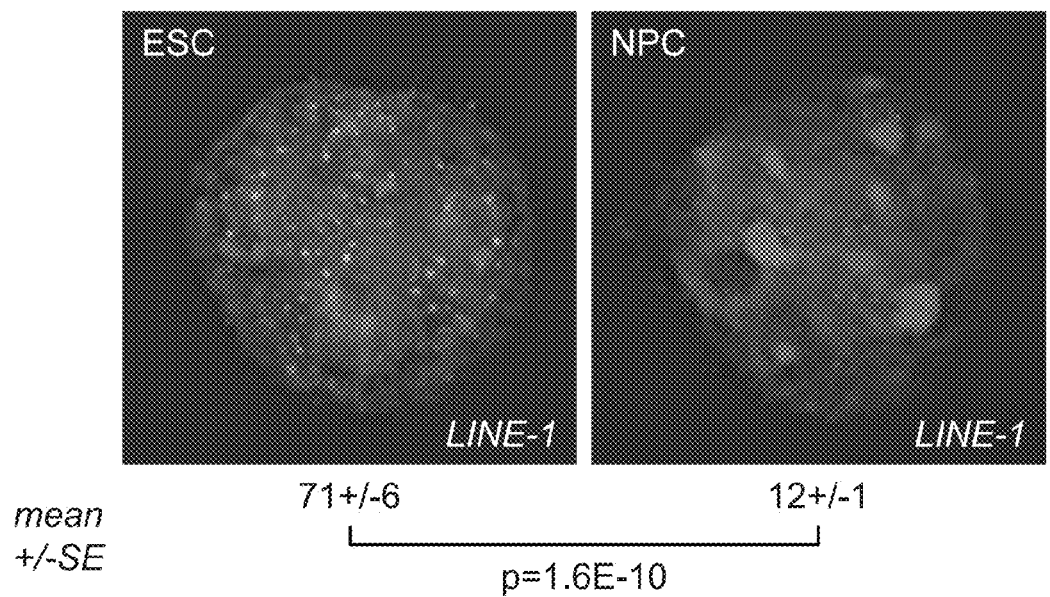
FIG. 8H is an image of RNA-FISH showing active transcription of LINE-1 transposable elements in ESCs, but not in NPCs, with mean and standard error of mean (SE) of the number of RNA-FISH signals per nucleus (N=30 from two biological replicates) and the P-value obtained from a two-tailed t-test for comparison of two unpaired groups shown.

However, there are many exceptional genes, including classes of genes that are upregulated within EtoL or LtoL domains. In fact, a weak association of gene activation is detected within LtoL domains (see FIGS. 8E, 8F and 8G) that leads to a higher probability of very late genes being expressed after differentiation (see FIG. 8C vs. FIG. 8D). Moreover, these results demonstrate that there is little or no relationship between replication timing and the probability of transcription for genes replicated throughout nearly the entire first half of S-phase (see FIGS. 8C and 8D). Genes with >0.5 replication timing ratios have an equal probability of transcription while those with negative replication timing values have a very strong correlation between their replication time and their probability of being expressed. It should be noted that these analyses are limited by the fact that non-coding and transposon transcription is not taken into account and is difficult to accurately assess. See, e.g., Efroni et al., "Global transcription in pluripotent embryonic stem cells," Cell Stem Cell 2:437-447 (2008). In fact, it is found that LINE-1 transposons are expressed in mESCs, as recently shown for hESCs (see, e.g., Garcia-Perez et al., "LINE-1 retrotransposition in human embryonic stem cells," Hum. Mol. Genet. 16:1569-1577 (2007)), and that these active LINE-1 elements are then repressed during the course of differentiation (see FIG. 8H), consistent with a recent report (see, e.g., Efroni et al., (2008), supra). Since EtoL domains are exceptionally enriched for LINE-1 elements (see FIG. 8G), it is possible that LINE-1 silencing takes place within the EtoL domains, something that is currently impossible to verify since the elements are so highly repetitive and widespread. In short, while there is a general trend for replication timing and transcription to change coordinately, given the number of exceptional examples, it is highly unlikely that there is a direct relationship between replication timing and transcription.

Replication Timing Correlates with Active, but not Repressive Histone Marks

Figure 9B:
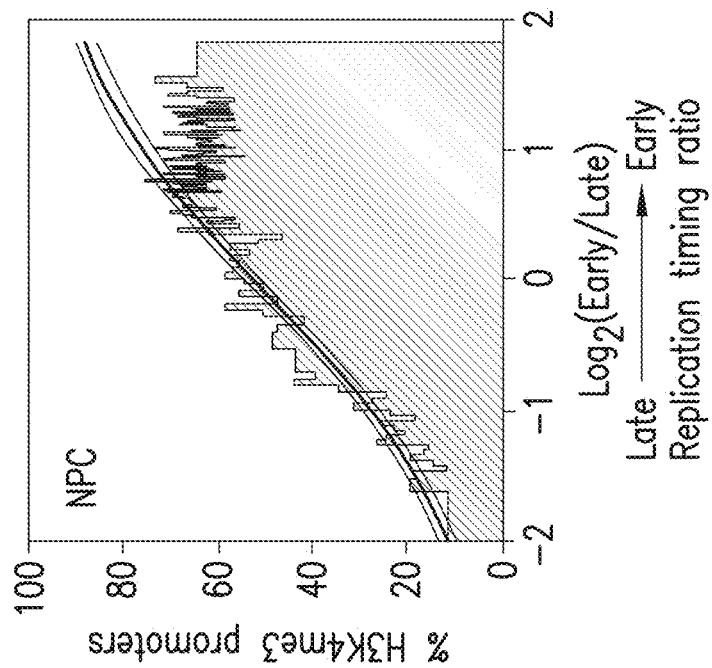
FIG. 9B is a bar graph of "bins" of 100 genes ranked according to their replication timing ratios for NPCs with the width of each bin representing the range of replication timing ratios needed to achieve 100 genes per bin and the height of each bin representing the percentage of H3K4me3-positive genes within each bin, with logistic regression (inner line) and 95% confidence intervals (outer lines) shown.
Figure 9A:
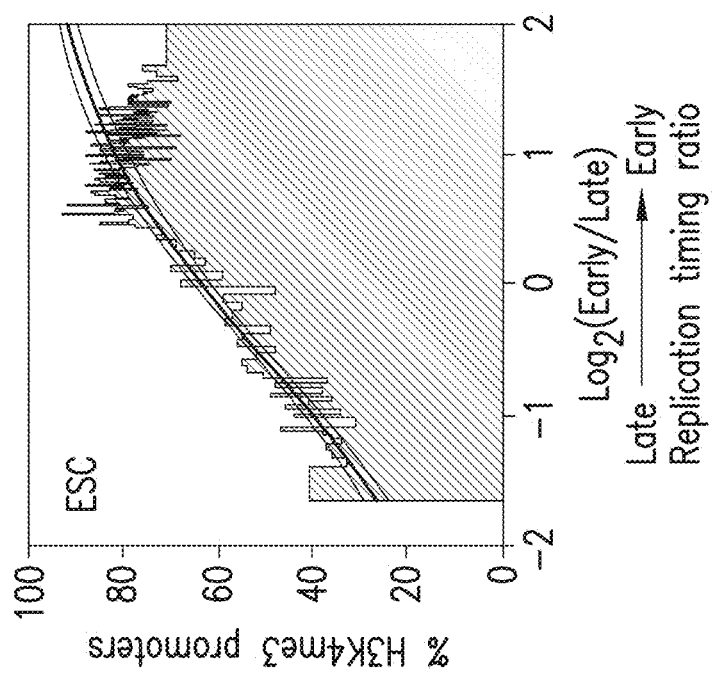
FIG. 9A is a bar graph of "bins" of 100 genes ranked according to their replication timing ratios for ESCs with the width of each bin representing the range of replication timing ratios needed to achieve 100 genes per bin and the height of each bin representing the percentage of H3K4me3-positive genes within each bin, with logistic regression (inner line) and 95% confidence intervals (outer lines) shown.
Figures 9C, 9E:
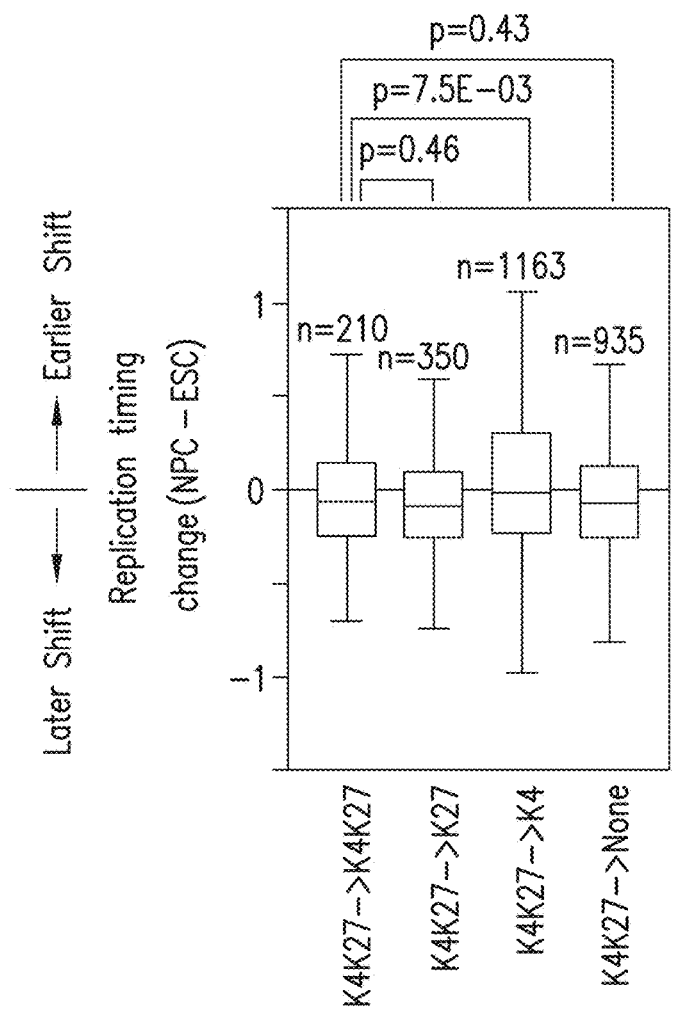
FIG. 9C is a table showing the relationship between replication timing and the density of different histone modifications (total intensity/domain size) based on a ChIP-Seq study (see, Mikkelsen et al., "Genome-wide maps of chromatin state in pluripotent and lineage-committed cells," Nature 448:553-560 (2007)) calculated for all replication domains in ESCs or NPCs and expressed in terms of Pearson's $R^2$ values.
FIG. 9E is a graphical box plot showing the distribution of replication timing changes of "bivalently" modified genes (=K4/K27) in ESCs that change to four different modification state (K4/K27, K27, K4, or none) in NPCs with horizontal bars representing the 10th, 25th, 50th (median), 75th, and 90th percentiles and P-values obtained from a two-tailed t-test for comparison of two unpaired groups shown.
Figure 9D:
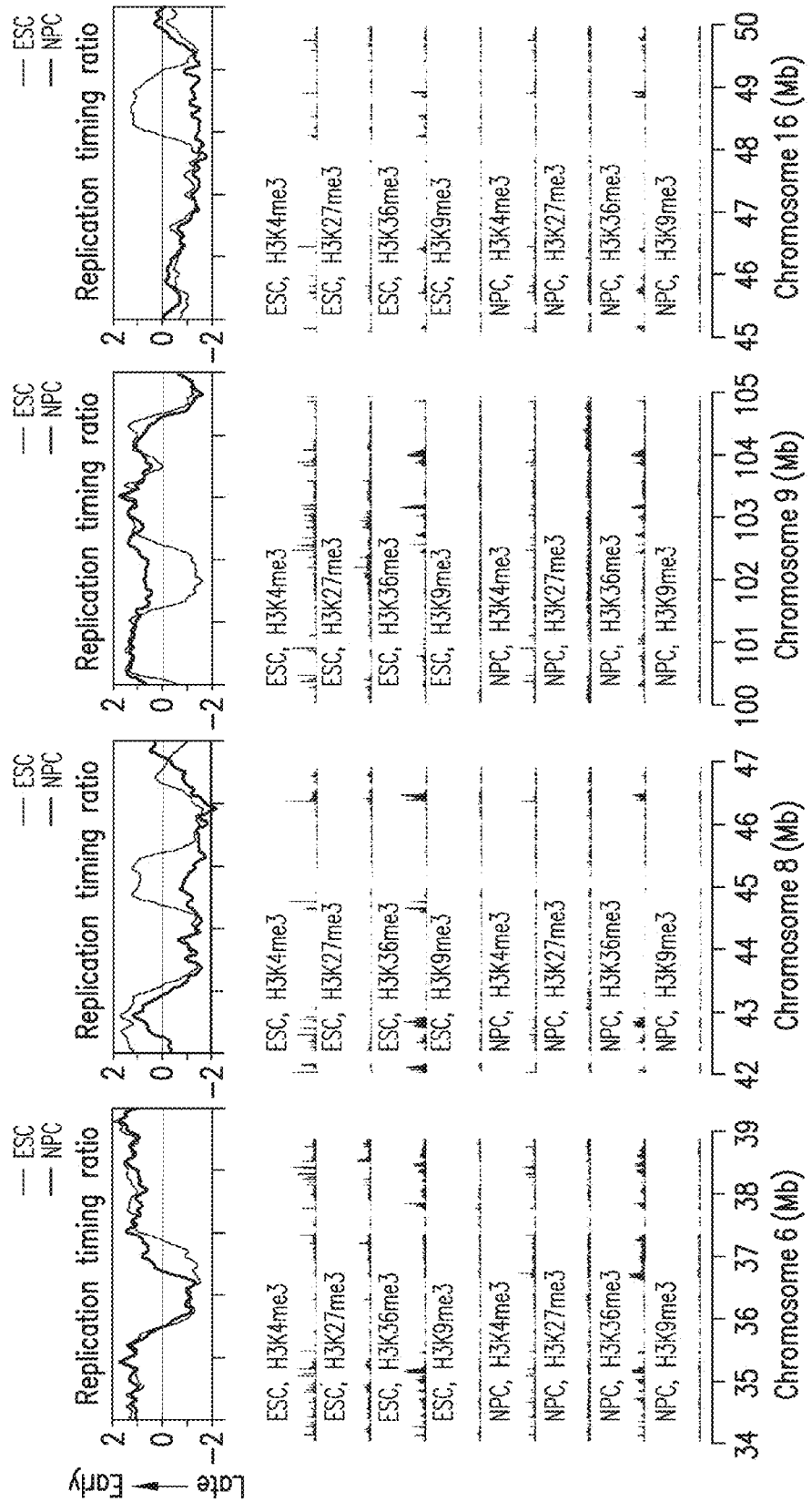
FIG. 9D is a set of graphical plots comparing replication timing ratios with different histone modifications in four exemplary 5 Mb genomic regions of ESCs and NPCs.

The relationship between replication timing and other epigenetic marks that have been analyzed in mESCs and NPCs (see, e.g., Mikkelsen et al., "Genome-wide maps of chromatin state in pluripotent and lineage-committed cells," Nature 448:553-560 (2007), the entire contents and disclosure of which are hereby incorporated by reference) is also examined. A strong positive correlation is found, resembling the correlation to transcription, between early replication and both lysine 4 tri-methylation of histone H3 (H3K4me3) near promoters and H3K36me3 throughout the bodies of genes. This correlation is observed both at the level of individual genes (see FIGS. 9A and 9B) and when the density of these marks is integrated within the boundaries of each replication domain (see FIG. 9C). Similar to transcription, a positive correlation is maintained during differentiation. Logistic regression (inner line) and 95% confidence intervals (outer lines) reveal a strong correlation in both ESCs (see FIG. 9A) and NPCs (see FIG. 9B) ($p<2\times10^{-16}$ bp the Likelihood Ratio test). This may be expected due to the association of these chromatin marks with transcription. See, e.g., Li et al., "The role of chromatin during transcription," Cell 128:707-719 (2007). However, there is a significant decrease in the positive correlation to these marks during differentiation (see FIG. 9C), as well as the overall number of H3K4me3 promoters (see FIGS. 9A and 9B), which is consistent with the finding that there is more overall coding and non-coding transcription in ESCs vs. NPCs (see, e.g., Efroni et al., (2008), supra). In contrast, there is no significant relationship between late replication and the repressive marks H3K27me3, H3K9me3 or H4K20me3 (see FIG. 9C). This finding is also evident from visual inspection of representative genomic regions (see FIG. 9D). Strikingly, a large fraction of genes that change replication timing during differentiation do not contain any of these marks at their promoters, which is also true for genes that remained late replicating in both differentiation states. It is concluded that replication timing correlates with annotated chromatin marks that reflect active transcription but not repression.

This finding contradicts a report that found a strong correlation between late replication and H3K27me3 in HeLa cells for the 1% of the genome covered by ENCODE. See, e.g., Thurman et al., "Identification of higher-order functional domains in the human ENCODE regions," Genome Res 17:917-927 (2007). However, the conclusions described herein are supported by several other observations. First, 87% of promoters marked by H3K27me3 in ESCs are early replicating. Second, disruption of the Eed gene, a subunit of the Polycomb complex PRC2, eliminates H3K27me3 in ESCs but does not affect replication timing of several tested genes. See, e.g., Jorgensen et al., "The impact of chromatin modifiers on the timing of locus replication in mouse embryonic stem cells," Genome Biol. 8:R169 (2007), the entire contents and disclosure of which are hereby incorporated by reference. Third, LINE-1 elements, which are highly enriched in late replicating DNA, are not enriched for either H3K27me3 or H3K9me3 in ESCs. See, e.g., Martens et al., "The profile of repeat-associated histone lysine methylation states in the mouse epigenome." EMBO J. 24:800-812 (2005), the entire contents and disclosure of which are hereby incorporated by reference. Differences in the findings described herein could be due to the small fraction of the genome queried by ENCODE regions, or biological differences between ESCs vs. HeLa cells.

Replication Timing Changes are Unrelated to the Resolution of "Bivalency"

Approximately 2,500 silent, developmentally regulated promoters in ESCs are characterized by a "bivalent" state co-occupied by active (H3K4me3) and repressive (H3K27me3) histone modifications. See, e.g., Mikkelsen et al., "Genome-wide maps of chromatin state in pluripotent and lineage-committed cells," Nature 448:553-560 (2007); Azuara et al., "Chromatin signatures of pluripotent cell lines," Nat. Cell Biol. 8:532-538 (2006); and Bernstein et al., "A bivalent chromatin structure marks key developmental genes in embryonic stem cells," Cell 125:315-326 (2006), the entire contents and disclosures of which are hereby incorporated by reference) Many (not all) of these promoters resolve to harbor only one of the two modifications upon differentiation, with activated genes harboring H3K4me3, while those remaining silent harbor H3K27me3. To determine whether replication-timing changes reflect the resolution of bivalency, the list of "bivalent" genes in ESCs is surveyed. The majority of "bivalent" genes replicated in the first half of S-phase in both states (not shown) and there is no obvious relationship between changes in these modifications and replication timing changes (see FIG. 9E), demonstrating that resolution of bivalency is not related to replication timing changes observed upon differentiation.

High and Low CpG Density Promoters are Differentially Influenced by Late Replication Given the presence of genes that are not affected by replication timing, specific classes of promoters are distinguished by how they are influenced by changes in replication time. Mammalian promoters may be classified based on their CpG density as high, intermediate, and low CpG-containing promoters (HCP, ICP, and LCP, respectively), which are subject to different modes of regulation. See, e.g., Mikkelson et al., (2007), supra; and Weber et al., "Distribution, silencing potential and evolutionary impact of promoter DNA methylation in the human genome," *Nat. Genet.* 39:457-466 (2007), the entire contents and disclosure of which are hereby incorporated by reference. In fact, among active genes, those with HCP, ICP, and LCPs have the highest, intermediate, and lowest transcript levels, respectively, indicating that HCPs are more strongly expressed than ICP or LCPs (see FIG. 10A). Interestingly, it is found that LCP and ICP genes are generally repressed when residing within EtoL domains, whereas HCP genes are not significantly affected (see FIG. 10B). On the other hand, gene activation occurs regardless of promoter CpG density for genes within LtoE domains (see FIG. 10C), consistent with the switch to early replication creating a generally permissive environment for transcription. Moreover, activation of genes within LtoL domains is significantly biased toward HCP genes (not shown). These results suggest that the transcription of CpG-rich, strongly expressed promoters is not significantly affected by entering a late-replicating environment.

Example 11

Temporal Re-organization Reflects Spatial Re-organization

Figure 11A:
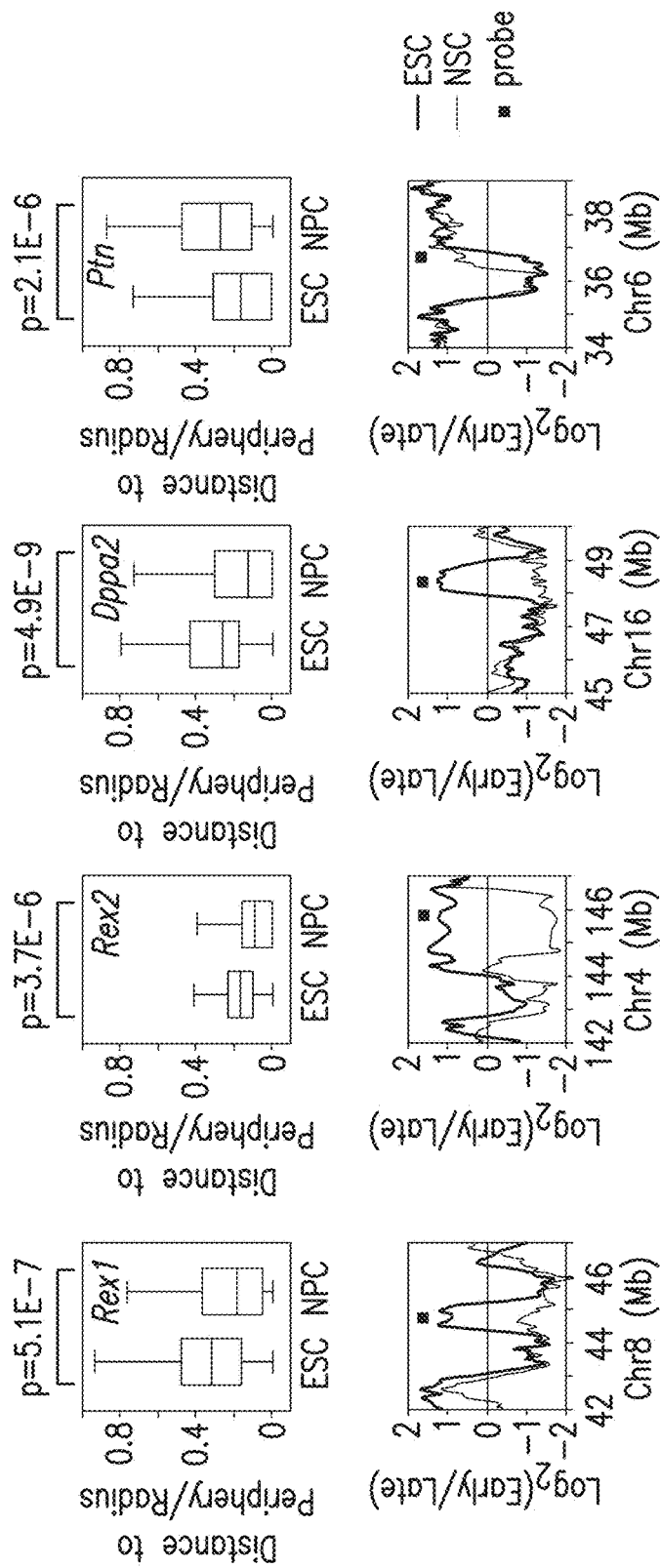
Figures 1, 11A:
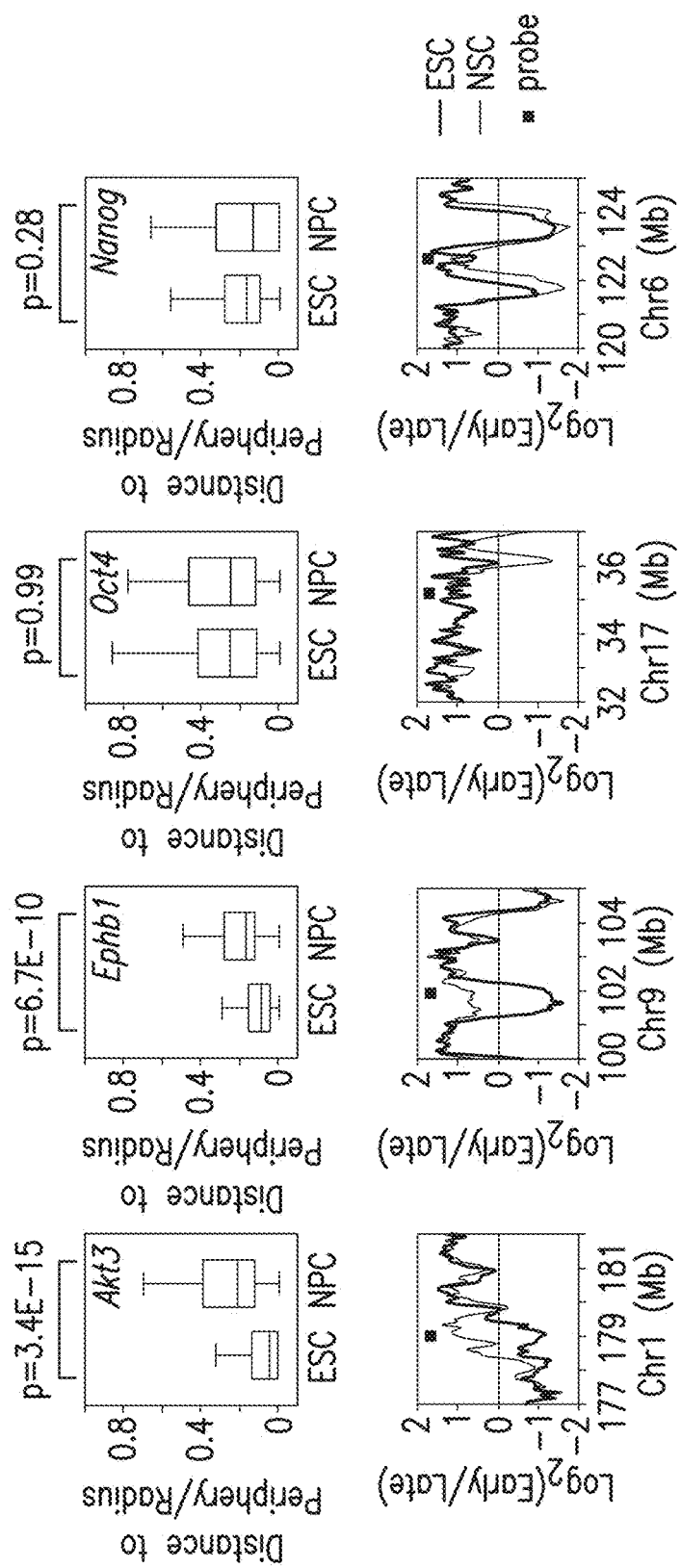
Figure 11B:
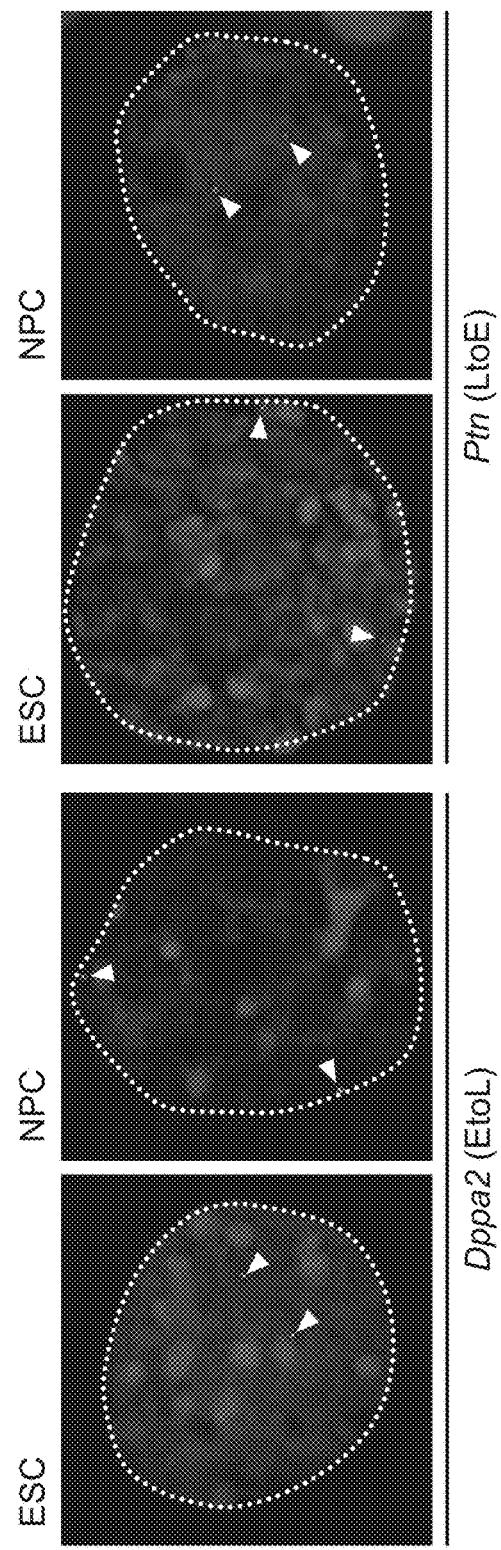
FIG. 11B is a representative set of images showing DNA-FISH signals (arrowheads) for Dppa2 and Ptn with dotted lines representing the rim of nuclear DAPI signal.

Early replication generally takes place in the interior of the nucleus, whereas the nuclear periphery is a late replicating compartment. See, e.g., Dimitrova et al., "The spatial position and replication timing of chromosomal domains are both established in early G1-phase," *Mol. Cell.* 4:983-993 (1999); and O'Keefe et al., "Dynamic organization of DNA replication in mammalian cell nuclei—spatially and temporally defined replication of Chromosome-Specific alpha-Satellite DNA sequences," *J. Cell Biol.* 116:1095-1110 (1992), the entire contents and disclosures of which are hereby incorporated by reference. This spatio-temporal organization of replication is thought to be similar in ESCs and differentiated cells. See, e.g., Panning et al., "Spatiotemporal organization of DNA replication in murine embryonic stem, primary, and immortalized cells," *J. Cell Biochem.* 95:74-82 (2005); and Wu et al., "Differential subnuclear localization and replication timing of histone H3 lysine 9 methylation states," *Mol. Biol. Cell* 16:2872-2881 (2005), the entire contents and disclosures of which are hereby incorporated by reference. Hence, the radial subnuclear position (distance to the nuclear periphery) of 8 individual genes is investigated before and after differentiation, using 3-dimensional (3D) fluorescence in situ hybridization (FISH) to preserve nuclear morphology. Results (see FIGS. 11A and 11B) reveal that genes within EtoL and LtoE domains move toward or away from the nuclear periphery, respectively, during differentiation. For example, three genes within EtoL domains (Rex1, Rex2 and Dppa2 domains) and three genes within LtoE domains (Ptn, Akt3 and Ephb1 domains) move toward and away from the nuclear periphery, respectively, upon neural differentiation, while two genes within EtoE domains (Oct4 and Nanog) do not change subnuclear positioning. Comparable results are obtained from 2-4 biological replicates and the sum of all experiments is shown, and 90-234 alleles are measured per state. Sub-nuclear position changes occur regardless of whether the replication timing changes are involved in domain 'consolidation' (Rex1, Rex2, Dppa2, Ephb1), "boundary shift" (Ptn), or "isolation" (Akt3). In contrast, two control EtoE down-regulated genes (Oct4 and Nanog) remain in the nuclear interior during differentiation.

Figure 11C:
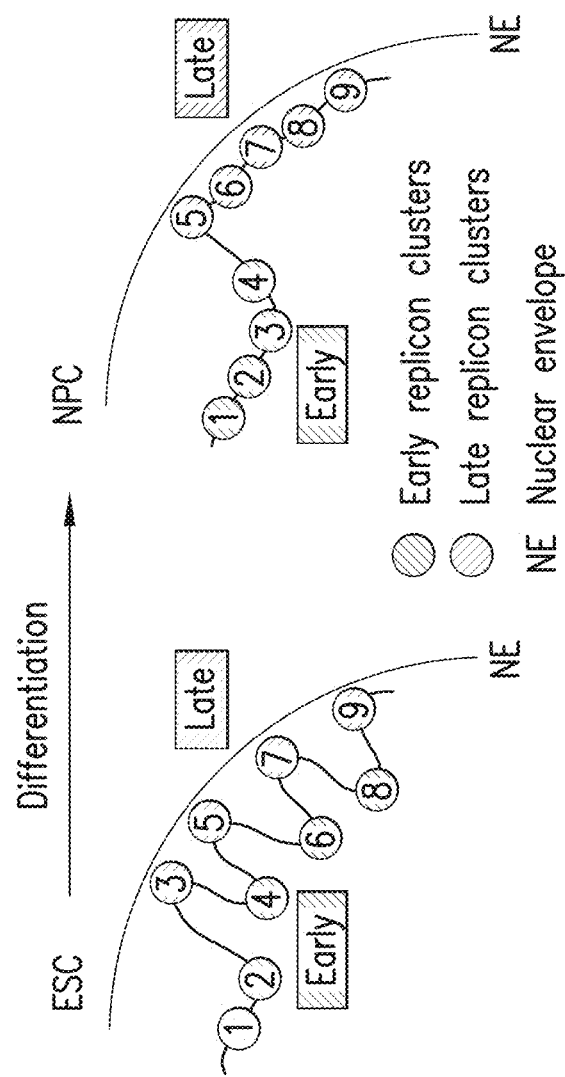
FIG. 11C is a model diagram representing a proposed higher order chromosomal organization in the nucleus during neural differentiation.

These results strongly suggest that the global temporal re-organization of replication domains reflects global 3D spatial re-organization of chromosomes in the nucleus (see FIG. 11C). According to this model, there is an increased influence of isochore sequence features on replication timing, resulting in the temporal consolidation of domains to align replication timing to isochores, possibly accompanied by spatial re-organization. Therefore, it is predicted that the generation of replication maps for various tissues may be used to create a database of chromosome segments that undergo large changes in 3D organization during differentiation.

All documents, patents, journal articles and other materials cited in the present application are hereby incorporated by reference in their entirety. Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for identifying cells comprising the following steps:
   (a) separating a population of sample cells having a particular cell type into subpopulations of sample cells based on cell cycle stages, wherein each subpopulation of sample cells consists essentially of sample cells from a specific cell cycle phase;
   (b) isolating genomic DNA from each subpopulation of sample cells;
   (c) separately sequencing genomic DNA isolated from each subpopulation of sample cells, thereby generating a replication timing test profile for the population of sample cells; and
   (d) identifying the particular cell type of the population of sample cells by comparing the replication timing test profile to a set of replication timing reference profiles for a set of known cell types.

2. The method of claim 1, wherein the population of sample cells comprises a cell line.

3. The method of claim 1, wherein the population of sample cells comprises primary cells derived from an individual.

4. The method of claim 1, wherein the population of sample cells comprises embryonic stem cells, precursor cells, iPS cells, or differentiated cells.

5. The method of claim 1, wherein the population of sample cells comprises diseased, transformed, or tumorigenic cells.

6. The method claim 1, wherein the population of sample cells comprises a population of mammalian cells.

7. The method of claim 1, wherein each replication timing reference profile of the set of replication timing reference profiles comprises a replication timing fingerprint for a particular known cell type.

8. The method of claim 7, wherein the replication timing fingerprint is defined as at least one region of a chromosome from cells of the particular known cell type that differs in replication timing ratio values by at least about 0.5 across a distance of at least about 50 kilobases (kb) compared to different cell types.

9. The method of claim 1,
wherein the population of sample cells are separated into a subpopulation of G1-phase sample cells and a subpopulation of S-phase sample cells,
wherein the replication timing test profile comprises loess-smoothed replication timing ratio values for the population of sample cells based on sequencing the genomic DNA of the subpopulation of G1-phase sample cells and the genomic DNA of the subpopulation of S-phase sample cells, and
wherein each loess-smoothed replication timing ratio value of the loess-smoothed replication timing ratio values is equal to $\log_2$(G1-phase/S-phase replication).

10. The method of claim 9, wherein the separating step comprises separating cells by fluorescent-activated cell sorting (FACS).

11. The method of claim 1,
wherein the population of sample cells are separated into a subpopulation of early S-phase sample cells and a subpopulation of late S-phase sample cells,
wherein the replication timing test profile comprises loess-smoothed replication timing ratio values for the population of sample cells based on sequencing the genomic DNA of the subpopulation of early S-phase sample cells and the genomic DNA of the subpopulation of late S-phase sample cells, and
wherein each loess-smoothed replication timing ratio value of the loess-smoothed replication timing ratio values is equal to $\log_2$(early/late S-phase replication).

12. The method of claim 1 comprising,
generating the set of replication timing reference profiles for a set of known cell types, wherein each replication timing reference profile is generated by:
separating a population of reference cells having a particular known cell type into a subpopulation of G1-phase reference cells and a subpopulation of S-phase reference cells;
isolating genomic DNA separately from the subpopulation of G1-phase reference cells and the subpopulation of S-phase reference cells; and
separately sequencing genomic DNA isolated from the subpopulation of G1-phase reference cells and genomic DNA isolated from the subpopulation of S-phase reference cells, thereby generating a replication timing reference profile for the particular known cell type of the population of reference cells.

13. The method of claim 1 comprising generating the set of replication timing reference profiles for a set of known cell types, wherein each replication timing reference profile is generated by:
separating a population of reference cells having a particular known cell type into a subpopulation of early S-phase reference cells and a subpopulation of late S-phase reference cells;
isolating genomic DNA separately from the subpopulation of early S-phase reference cells and the subpopulation of late S-phase reference cells; and
separately sequencing genomic DNA isolated from the subpopulation of early S-phase reference cells and the subpopulation of late S-phase reference cells, thereby generating a replication timing profile for the particular known cell type of the population of reference cells.

14. The method of claim 1, wherein the replication timing test profile comprises loess-smoothed replication timing ratio values for the population of sample cells,
wherein each replication timing reference profile of the set of replication timing reference profiles comprises loess-smoothed replication timing ratio values for a particular known cell type,
wherein the particular cell type of the population of sample cells is identified as one of the set of known cell types if the loess-smoothed replication timing ratio values for the population of sample cells are substantially the same as loess-smoothed replication timing ratio values for the one of the set of known cell types.

15. The method of claim 14, wherein the loess-smoothed replication timing ratio values for the population of sample cells are substantially the same as loess-smoothed replication timing ratio values for the one of the set of known cell types if at least about 95% of the loess-smoothed replication timing ratio values for the population of sample cells and the loess-smoothed replication timing ratio values for the one of the set of known cell types differ by a differential value of less than about 0.5.

16. The method of claim 14, wherein the loess-smoothed replication timing ratio values for the population of sample cells are substantially the same as loess-smoothed replication timing ratio values for the one of the set of known cell types if less than about 5% of the loess-smoothed replication timing ratio values for the population of sample cells and the loess-smoothed replication timing ratio values for the one of the set of known cell types differ by a differential value of more than about 0.5.

17. The method of claim 1, wherein step (d) is performed by a computer.

* * * * *